United States Patent [19]

Denes

[11] Patent Number: 5,631,206
[45] Date of Patent: May 20, 1997

[54] HERBICIDAL HETEROARYL SUBSTITUTED ANILIDES

[75] Inventor: Lucian R. Denes, Hockessin, Del.

[73] Assignee: E. I. Du Pont de Nemours and Company, Wilmington, Del.

[21] Appl. No.: 600,985

[22] PCT Filed: Sep. 21, 1994

[86] PCT No.: PCT/US94/10342

§ 371 Date: Apr. 1, 1996

§ 102(e) Date: Apr. 1, 1996

[87] PCT Pub. No.: WO95/09846

PCT Pub. Date: Apr. 13, 1995

[51] Int. Cl.$^6$ .................. C07D 213/16; A01N 43/40
[52] U.S. Cl. .................. 504/130; 504/133; 504/136; 504/138; 504/139; 544/211; 544/336; 544/242; 546/309; 548/136; 548/205; 548/235; 548/561; 548/335.1; 548/335.5; 548/316.4
[58] Field of Search .................. 546/309; 544/211, 544/336, 242; 548/136, 205, 235, 561, 335.3; 504/130, 133, 136, 138, 139

[56] References Cited

FOREIGN PATENT DOCUMENTS

WO93/11097 6/1993 WIPO.

Primary Examiner—Zinna Northington Davis

[57] ABSTRACT

Compounds of formula (I) having herbicidal utility are disclosed;

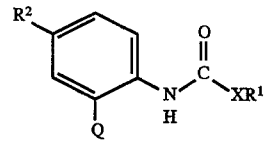

wherein Q is a variety of heteroaromatic groups; X is a single bond; O; S; or $NR^4$; $R^1$ is $C_1$-$C_5$ alkyl optionally substituted with $C_1$-$C_2$ alkoxy, OH, 1-3 halogens, or $C_1$-$C_2$ alkylthio; $CH_2(C_3$-$C_4$ cycloalkyl); $C_3$-$C_4$ cycloalkyl optionally substituted with 1-3 methyl groups; $C_2$-$C_4$ alkenyl; or $C_2$-$C_4$ haloalkenyl; $R^2$ is H; chlorine; bromine; $C_1$-$C_2$ alkyl; $C_1$-$C_2$ alkoxy; $C_1$-$C_2$ alkylthio; $C_2$-$C_3$ alkoxyalkyl; $C_1$-$C_2$ alkylthioalkyl; cyano; nitro; $NH(C_1$-$C_2$ alkyl); or $N(C_1$-$C_2$ alkyl)$_2$; $R^4$ is H; $CH_3$; or $OCH_3$; and agriculturally suitable salts thereof.

10 Claims, No Drawings

HERBICIDAL HETEROARYL SUBSTITUTED ANILIDES

This application is a 371 of PCT/US94/10342 filed Sep. 12, 1994.

This invention relates to certain heteroaryl substituted anilides which are useful as herbicides and their agriculturally suitable compositions as well as methods for their use as general or selective preemergent or postemergent herbicides or as plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. Them are many products commercially available for these purposes, but the search continues for products which are more effective, less costly and environmentally safe.

WO93/11097 discloses herbicidal anilide derivatives wherein an optionally substituted phenyl group occupies the ortho-position. In contrast, the compounds of the present invention bear a heteroaromatic group at that location and are therefore not disclosed therein.

SUMMARY OF THE INVENTION

The invention comprises compounds of Formula I:

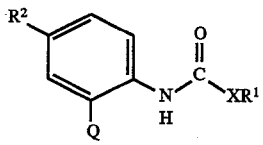

wherein Q is

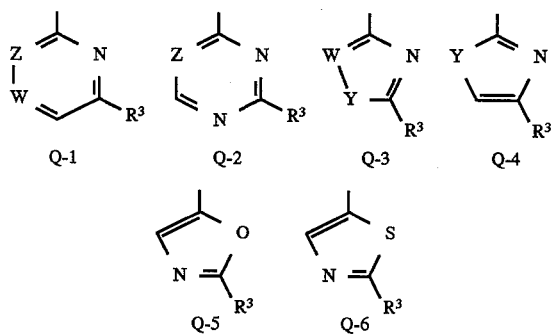

X is a single bond; O; S; or $NR^4$;
Y is O; S; or $NCH_3$;
Z is CH or N;
W is CH or N;
$R^1$ is $C_1$-$C_5$ alkyl optionally substituted with $C_1$-$C_2$ alkoxy, OH, 1–3 halogens, or $C_1$-$C_2$ alkylthio; CH2 ($C_3$-$C_4$ cycloalkyl); $C_3$-$C_4$ cycloalkyl optionally substituted with 1–3 methyl groups; $C_2$-$C_4$ alkenyl; $C_2$-$C_4$ haloalkenyl; or optionally substituted phenyl;
$R^2$ is H; chlorine; bromine; $C_1$-$C_2$ alkyl; $C_1$-$C_2$ alkoxy; $C_1$-$C_2$ alkylthio; $C_2$-$C_3$ alkoxyalkyl; $C_2$-$C_3$ alkylthioalkyl; cyano; nitro; $NH(C_1$-$C_2$ alkyl); or $N(C_1$-$C_2$ alkyl)$_2$;

$R^3$ is $C_1$-$C_4$ haloalkyl; $C_1$-$C_4$ haloalkoxy; $C_1$-$C_4$ haloalkylthio; halogen; cyano; nitro; or methylthio;
$R^4$ is H; $CH_3$ or $OCH_3$; and agriculturally suitable salts thereof.

Preferred compounds of Formula I for reasons of greatest herbicidal activity and/or ease of synthesis are:

1. Compounds of Formula I wherein:
$R^1$ is $C_1$-$C_4$ alkyl optionally substituted with methoxy or 1–3 halogens; $C_2$-$C_4$ alkenyl; or $C_2$-$C_4$ haloalkenyl;
$R^2$ is chlorine; bromine; $C_1$-$C_2$ alkyl; $C_1$-$C_2$ alkoxy; cyano; nitro; $NH(C_1$-$C_2$ alkyl); or $N(C_1$-$C_2$ alkyl)$_2$.

2. Compounds of Preferred 1 wherein:
X is a single bond;
$R^3$ is $C_1$-$C_2$ haloalkyl; $C_1$-$C_2$ haloalkoxy; $C_1$-$C_2$ haloalkylthio; chlorine or bromine.

3. Compounds of Preferred 2 wherein:
Q is Q-1 or Q-2.

Specifically preferred for greatest herbicidal activity and/or ease of synthesis are: 2-methyl-N-[4-methyl-2-[6-(trifluoromethyl)-2-pyridinyl]phenyl]-propanamide; and 2-methyl-N-[4-methyl-2-[2-(trifluoromethylthio)-4-pyrimidinyl]-phenyl]-propanamide.

Further embodiments of the invention include:

A composition for controlling growth of undesired vegetation comprising a herbicidally effective mount of a compound of Formula I as defined herein and at least one of a surfactant, solid or liquid diluent.

A method of controlling the growth of undesired vegetation comprising applying to the locus to be protected a herbicidally effective amount of the composition described above.

DETAILED DESCRIPTION OF THE INVENTION

Compounds of General Formula I can be readily prepared by one skilled in the art by using the reactions and techniques described in Schemes 1–7 of this section as well as by following the specific procedures given in Examples 1–13. The definitions of Q, X, Y, Z and $R^1$-$R^4$ are as described in the Summary of the Invention.

Scheme 1 illustrates the preparation of compounds of Formula I whereby substituted phenyl compounds of Formula IIa wherein $X^2$ is triakyltin (e.g., Me$_3$Sn), triakylsilyl (e.g., Me$_3$Si), or a boronic acid derivative (e.g., B(OH)$_2$) are coupled with heterocycles of Formula IIIa wherein $X^1$ is chlorine, bromine, iodine or trifluoromethylsulfonyloxy (OTf). The coupling is carried out by methods known in the art: for example, see Tsuji, J., Organic Synthesis with Palladium Compounds, Springer-Verlag, Berlin (1980); Negishi, E., Acc. Chem. Res. (1982), 15, 340; Stille, J. K., Angew. Chem. (1986), 98, 504; Yamamoto, A. and Yamagi, A., Chem. Pharm. Bull. (1982), 30, 1731 and 2003; Dondoni et at., Synthesis (1987), 185; Dondoni et al., Synthesis (1987), 693; Hoshino et al., Bull. Chem. Soc. Jpn. (1988), 61, 3008; Sato, M. et al., Chem. Left. (1989), 1405; Miyaura et al., Synthetic Commun. (1981), 11,513; Siddiqui and Sniekus, Tetrahedron Lat. (1988), 29, 5463; Sharp at al., Tetrahedron Lett. (1987), 28, 5093; Hatanaka et at., Chem. Lett., (1989), 1711; Bailey, T. R., Tetrahedron Lett. (1986), 27, 4407, Echavarren, A. M. and Stille, J. K., J. Am. Chem. Soc. (1987), 109, 5478, and Ali et al., Tetrahedron Lat. (1992), 48, 8117. The coupling of IIa and IIIa is carried out by heating the mixture in the presence of a transition metal catalyst such as tetrakis(triphenylphosphine) palladium(O)

or bis(triphenylphosphine)-palladium (11) dichloride in a solvent such as toluene, acetonitrile, glyme, or tetrahydrofuran optionally in the presence of an aqueous inorganic base such as sodium hydrogen carbonate or an organic base such as triethylamine. One skilled in the art will recognize that when IIIa contains more than one reactive substituent, then the stoichiometric ratios of reagents will need to be adjusted to minimize bis-coupling.

Scheme 1

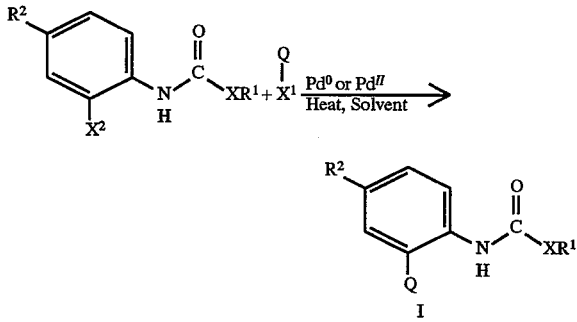

IIa: $X^2$ = trialkyltin, trialkylsilyl, or a boronic acid derivative
IIb: $X^2$ = Cl, Br, I or OTf
IIIa: $X^1$ = Cl, Br, I, or OTf
IIIb: $X^1$ = trialkyltin, trialkylsilyl, or a boronic acid derivative Conversely, the anilides of Formula I can be prepared by reversing the reactivity of the two substrates. Substituted phenyl compounds of Formula IIb wherein $X^2$ is chlorine, bromine, iodine or trifluoromethylsulfonyloxy (OTf) can be coupled with heteroaromatic compounds of Formula IIIb wherein $X^1$ is trialkyltin (e.g., $Me_3Sn$), trialkylsilyl (e.g., $Me_3Si$), or a boronic acid derivative (e.g., $B(OH)_2$). The procedure for conducting the coupling is the same as those described and referenced above.

By methods also reported in the above cited literature, compounds of Formula IIa and IIIb are prepared by treating the corresponding halide (i.e., wherein $X^1$ and $X^2$ is bromine or iodine) with a metalating agent such as n-butyllithium followed by quenching with a trialkyltin halide, trialkylsilyl halide, boron trichloride, or trialkyl borate.

Some compounds of Formula IIa can also be prepared from the corresponding ortho-unsubstituted compound (i.e., wherein $X^2$ is hydrogen) by treatment with a base such as n-butyllithium followed by quenching with a trialkyltin halide, trialkylsilyl halide, or trialkyl borate as reported in the same literature references. This preparation requires that —NHC(=O)$XR^1$ is an ortho-metalation directing group known in the art (e.g., trimethylacetylamido): see for example, Fuhrer, W., J. Org. Chem., (1979), 44, 1133.

Anilides and heteroaromatics of Formula II and III wherein $X^1$ and $X^2$ are chlorine, bromine, iodine, OTf, and hydrogen are either known or readily prepared by procedures and techniques well known in the art, for example: Houben-Weil, Methoden der Organische Chemie, IV edition, Eugen Muller, Ed., Georg Thieme Verlag; Turchi, I. J., The Chemistry of Heterocyclic Compounds, Vol. 45, pp. 36–43, J. Wiley & Sons, New York (1986); L. S. Wittenbrook, G. L. Smith, R. J. Timmons, J Org. Chem. (1973), 38, 465–471; and P. Reynaud, et al., Bull. Soc. Chim. Fr. (1962), 1735–1738.

Compounds of Formula I can also be prepared by one skilled in the art from anilines of Formula IV by treatment with an appropriate acyl chloride or acid anhydride (X=direct bond), chloroformate (X=O), chlorothiolformates (X=S), carbamoyl chloride (X=NCH$_3$), or isocyanate (X=NH) under conditions well known in the literature, for example: Sandler, R. S. and Karo, W., Organic Functional Group Preparations, 2nd Edition, Vol. I, p 274 and Vol. II, pp 152, 260, Academic Press (Scheme 2).

Scheme 2

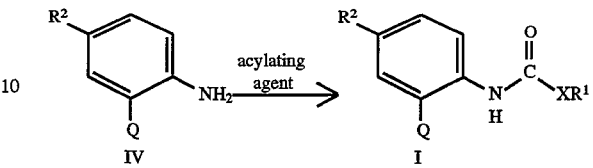

Alternatively, anilines of Formula IV can be convened into the corresponding isocyanate by treatment with phosgene or known phosgene equivalents (e.g., ClC(=O)OCCl$_3$), and then condensed with an appropriate alcohol or amine of Formula V to afford anilides of Formula I (Scheme 3). These techniques are well known in the literature. For example, see Sandlet, R. S. and Karo, W., Organic Functional Group Preparations, 2nd Edition, Vol. II, 152, 260, Academic Press; Lehman, G. and Teichman, H. in Preparative Organic Chemistry, 472, Hilgetag, G. and Martini, A., Eds., John Wiley & Sons, New York, (1972); Eckert, H. and Forster, B., Angew. Chem., Int. Ed., (1987), 26, 894; Babad, H. and Zeiler, A. G., Chem. Rev., (1973), 73, 75.

Scheme 3

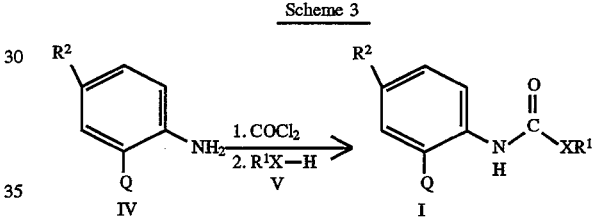

Anilines of Formula IV are readily prepared by palladium catalyzed coupling of an ortho-substituted nitrophenyl compound of Formula VIa, wherein $X^2$ is as defined above, with a heteroaromatic compound of Formula III, wherein $X^1$ is as defined above, followed by catalytic or chemical reduction of the nitro group (Scheme 4). As described for Scheme 1, the reactivity of the substrates can be reversed, i.e. the coupling is carded out using an ortho-substituted nitrophenyl compound of Formula VIb and a heteroaromatic compound of Formula IIIb.

Reduction of nitro groups to amino groups is well documented in the chemical literature. See for example, Ohme, R. and Zubek, A. R. and Zubek, A. in Preparative Organic Chemistry, 557, Hilgetag, G. and Martini, A., Eds., John Wiley & Sons, New York: (1972).

Scheme 4

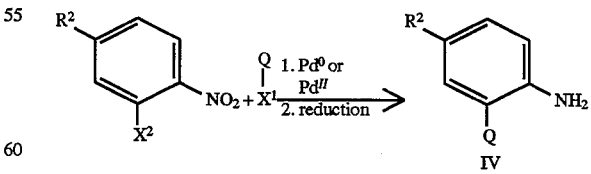

VIa: $X^2$ = trialkyltin, trialkylsilyl, or a boronic acid derivative
VIb: $X^2$ = Cl, Br, I or OTf
IIIa: $X^1$ = Cl, Br, I, or OTf
IIIb: $X^1$ = trialkyltin, trialkylsilyl, or a boronic acid derivative In some cases, it is desirable to perform the palladium coupling reaction on an N-protected form of the aniline, for example the 2,2-dimethylpropanamide. Upon completion of the coupling reaction, the N-protecting group can be removed, for example by treatment of the 2,2-dimethylpropanamide with acid, to liberate the amino group.

In other cases, it is advantageous to prepare compounds of Formula IV, not by the cross-coupling methods described above, but rather by elaboration of a substituted ortho-nitrobenzoic acid, or a derivative thereof (Formula VII), under any of a number of ring closure methodologies (Scheme 5). Subsequent reduction of the nitro compounds of Formula VIII provides compounds of Formula IV. One skilled in the art will recognize that these same ring closure methodologies can be used to elaborate a substituted ortho-aminobenzoic acid, or a derivative thereof, into compounds of Formula IV.

Scheme 5

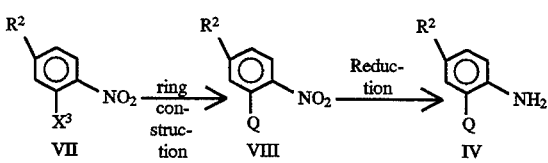

wherein $X^3$ can be any of a number of heterocycle building blocks, including, but not limited to those shown below:

$X^3$=CO2H, COCl, CO$_2$-alkyl, CONH$_2$, C(=S)NH$_2$, CHO, CN, C(=NOH)NH$_2$, COCH$_2$NH$_2$, and COCH$_2$-halogen.

Compounds of Formula VII are well known in the art or may be made by simple functional group interconversions on ortho-substituted nitrobenzenes.

Numerous methods for conversion of these $X^3$ substituents into 5-membered heterocycles are well known in the literature and can be applied by those skilled in the art for the preparation compounds of Formula VIII wherein Q is Q-3, Q-4, Q-5 or Q-6. For example, see A. R. Katritzky and C. W. Rees, Comprehensive Heterocyclic Chemistry, Vol. 6, pp. 216–222; 293–306; 386–391; 492–508, Pergamon Press, London (1984); R. Elderfield, Heterocyclic Compounds, Vol. 5, pp. 302–319; 495–505, J. Wiley & Sons, New York (1957); ibid., Vol. 7., pp. 508–518; 558–569, J. Wiley & Sons, New York (1961); I. J. Turehi, M. J. S. Dewar, Chem. Rev. (1975), 75(4), 389–436; A. M. Van Leusen, B. E. Hoogenboom, H. Siderius, Tetrahedron Lett. (1972), 2369–2372; F. Yokokawa, Y. Hamada, T. Shioiri, Synlett (1992), 153–155. This strategy is illustrated in Example 13.

In some instances, it may be necessary, or more convenient, to introduce the desired substituents after the coupling reaction was performed. This can be accomplished by electrophilic substitution (Scheme 6), or nucleophilic substitution and functional group modifications (Scheme 7) using procedures well documented in the literature. These strategies are illustrated in Examples 3–13.

Scheme 6

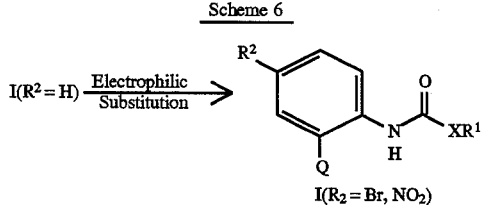

Variation of the substituent $R^3$ on the heterocycle Q of compounds of Formula I may be achieved by one of two ways. First, one skilled in the art may simply select the appropriate heteroaromatic compound of Formula III a, b for the palladium coupling in Schemes 1 and 4 to give examples with a variety of values for $R^3$. Alternatively, it may at times be convenient to vary $R^3$ by performing various functional group transformations on the previously assembled aryl-substituted heterocycle of Formula I as shown in Scheme 7. Methods to perform these transformations are well known in the literature. Some examples include conversion of chloro to bromo (L. J. Street, et al., J. Med. Chem. (1992), 35, 295–304), bromo to trifluoromethyl (J. Wrobel, et al., J. Med. Chem. (1989), 32(II), 2493–2500), cyano (G. P. Ellis, T. M. Romney-Alexander, Chem. Rev. (1987), 87, 779–794), alkoxy and alkylthio, aldehyde to difluoromethyl (W. J. Middleton, J. Org. Chem. (1975), 40, 574–578), thiol to trifluoromethylthio (V. I. Popov, V. N. Boiko, L. M. Yagupolskii, J. Fluor. Chem. (1982), 21, 365–369) and amino to a variety of substituents via the diazonium salts. Electrophilic aromatic substitution or metallation chemistry are also useful methods for incorporating certain substitutents.

Scheme 7

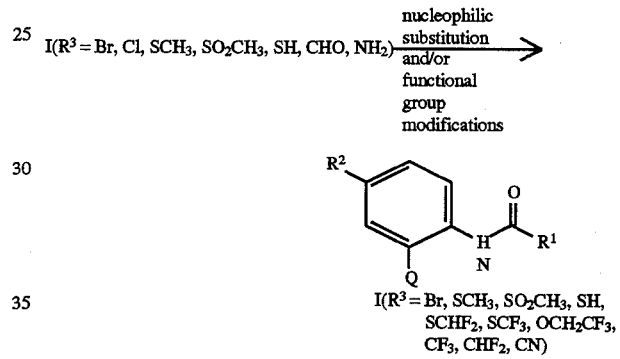

One skilled in the art will recognize that the above methods may require the use of protecting groups or subsequent functional group interconversions to avoid undesired side reactions with substituents which may be sensitive to the reaction conditions. One skilled in the an will also recognize that compounds of Formula I and the intermediates described above can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following examples are, therefore, to be construed as merely illustrative, and not limiting of the disclosure in any way whatsoever.

EXAMPLE 1

Preparation of N-(2-borono-4-methylphenyl)-2,2-dimethylpropanamide

A solution of 72.4 g N-(4-methylphenyl)-2,2-dimethylpropanamide in 1000 mL dry THF was cooled to −70° C. under nitrogen and 480 mL 2.5M nBuLi in hexanes was added dropwise over 1 h while maintaining the temperature below 60° C. Stirring was continued at −70° C. for 1 h, then the reaction was allowed to warm to room temperature with stirring overnight.

The reaction mixture was then cooled to −10° C. and 200 mL trimethyl borate was added dropwise while maintaining the temperature below 0° C. Stirring was continued at 0° C. for 2.5 h, 50 mL water was added dropwise over 0.5 h, and then concd. HCl was added to acidify the reaction. The solvents were removed in vacuo, 200 mL water added to form a slurry which was shaken (or stirred) thoroughly with ether. The white precipitate was collected by filtration, washed well with 1:1 ether/hexane mixture, then suspended in acetone and stirred for 20 min. While stirring, 600 mL water was added slowly in portions (more water may be necessary if precipitation is not complete). The white solid was collected by filtration, washed with water, then dried in a vacuum oven to yield 56.8 g of the title compound as a white powder. $^1$H NMR (CDCl$_3$): δ 1.03 (s,9H), 2.40 (s,3H), 7.20 (d, 1H), 7.80 (s,1H), 7.96 (d,1H), 9.8 (s,1H,NH).

EXAMPLE 2

Preparation of 2,2-dimethyl-N-[4-methyl-2-[2-(methylthio)-4-pyrimidinyl]phenyl]propanamide A mixture of 16 g (0.1 mol) 4-chloro-2-(methylthio) pyrimidine, 0.150 g palladium bis(triphenylphosphine) dichloride, and 30 mL dimethoxyethane was stirred under nitrogen for 20 min, 25.8 g (0.11 mol) N-(2-borono-4-methyl phenyl)-2,2-dimethylpropanamide and a solution of 26 g sodium bicarbonate in 300 mL water was added, and the resulting mixture was heated to reflux for 5 h. After cooling to 50° C., 50 mL ethyl acetate was added and the reaction mixture was stirred until it reached room temperature. The reaction mixture was diluted with 300 mL ethyl acetate and washed successively with water and brine. The organic extracts were dried over magnesium sulfate, faltered, and evaporated to dryness. The crude product was purified by chromatography on silica gel using 40:1 chlorobutane/ethyl acetate mixture as eluent to yield 25.2 g of the title compound as white crystals melting at 119°–20° C. $^1$H NMR (CDCl$_3$): δ 1.28 (s,9H), 2.38 (s,3H), 2.60 (s,3H) 7.30–8.6 (5H), 11.3(s,1H,NH).

EXAMPLE 3

Preparation of 4-methyl-2-[2-(methylthio)-4-pyrimidinyl]benzenamine 24 g 2,2-dimethyl-N-[4-methyl-2-[2-(methylthio)-4-pyrimidinyl]phenyl]propanamide was dissolved in 120 mL glacial acetic acid and the mixture warmed to reflux when 60 mL 15% hydrochloric acid solution was gradually added. After the addition was completed, the reaction mixture was heated at reflux for 4 h. After cooling, volatiles were removed in vacuo, the residue was taken up in 200 mL water and ice was added. The resulting mixture was neutralized to pH 10 with 5% sodium hydroxide solution and extracted with ether. Organic extracts were washed with brine, dried, evaporated to dryness and then dried in a vacuum oven to yield 6.2 g of the title compound as a tan solid melting at 120°–123° C. $^1$H NMR (CDCl$_3$): δ 2.30 (s,3H), 2.60 (s,3H), 5.8 (s,2H,NH$_2$), 6.60–8.6 (5H).

EXAMPLE 4

Preparation of 2-methyl-N-[4-methyl-2-[2-(methylthio)-4-pyrimidinyl]phenyl]propanamide A solution of 11.7 g (0.11 mol) isovaleryl chloride in 15 mL dry chloroform was added dropwise with stirring to a solution of 23.1 g (0.10 mol) 4-methyl-2-[2-(methylthio)-4-pyrimidinyl]benzenamine and 12 g pyridine in 60 mL dry chloroform. Stirring was continued for 1 h at room temperature, after which the reaction mixture was diluted with 200 mL ether and washed successively with water, 0.5N hydrochloric acid solution, and brine. The organic extracts were dried over magnesium sulfate, filtered, and evaporated to dryness. The crude product was purified by chromatography on silica gel using 10:1 chlorobutane/ethyl acetate mixture as eluent to yield 28.3 g of the title compound as white crystals melting at 134°–135° C. $^1$H NMR (CDCl$_3$): δ 1.23 (d,6H), 2.30 (s,3H), 2.40 (s,3H) 2.47 (m,1H), 7.40–8.6 (5H), 10.7(s,1H,NH).

EXAMPLE 5

Preparation of 2-methyl-N-[4-methyl-2-[2-(methylsulfonyl)-4-pyrimidinyl]phenyl]propanamide A total of 7.6 g 50% meta-chloroperbenzoic acid was added in small portions at room temperature during 6 h to a solution of 6 g (0.02 mol) 2-methyl-N-[4-methyl-2-[2-(methylthio)4-pyrimidinyl]phenyl]propanamide in 75 mL chloroform. Stirring was continued overnight. The reaction mixture was diluted with 100 mL methylene chloride and washed successively with water, 1N sodium thiosulfate solution, 1N sodium hydroxide solution, and brine. The organic layer was dried over magnesium sulfate, filtered, and evaporated to dryness. The crude product was purified by chromatography on silica gel using 10:1 chlorobutane/ethyl acetate mixture as eluent to yield 6.2 g of the title compound bright yellow crystals melting at 146°–149° C. $^1$H NMR (CDCl$_3$): δ 1.21 (d,6H), 2.40 (s,3H), 2.80 (m,1H) 3.40 (s,H), 7.40–8.80 (5H), 11.4 (s,1H,NH).

EXAMPLE 6

Preparation of N-[2-(2-mercapto-4-pyrimidinyl)-4-methylphenyl]-2-methylpropanamide 3.3 g (0.01 mol) 2-methyl-N-[4-methyl-2-[2-(methylsulfonyl)-4-pyrimidinyl]phenyl]propanamide was dissolved in 35 mL absolute ethanol and 3 g potassium hydrogen sulfide was added to this solution with stirring. The reaction mixture was stirred overnight at room temperature. 50 mL water was added and the volume reduced under vacuum to 40 mL. An additional 40 mL water was added and the solution thus obtained was made acidic with concentrated hydrochloric acid. The yellow precipitate was collected by filtration, washed with a little water, then dissolved in 50 mL 1N sodium hydroxide and treated with charcoal. The charcoal was filtered off and the filtrate was made acidic with concentrated hydrochloric acid. The bright yellow precipitate was collected by filtration, washed with water, then dried in a vacuum oven to yield 2.18 g of N-[2-(2-mercapto-4-pyrimidyl)-4-methylphenyl]-2-methylpropanamide. $^1$H NMR (CDCl$_3$): δ 1.21 (d,6H), 2.40 (s,3H), 2.75 (m,1H), 7.40–8.60 (5H), 11.4(s,1H,NH), 11.9 (s,1H,SH).

EXAMPLE 7

Preparation of 2-methyl-N-[4-methyl-2-[2-[(trifluoromethyl)thio]-4-pyrimidinyl]phenyl]propanamide 2 g trifluoromethyl iodide was condensed into a solution of 0.57 g (0.002 mol) N-[2-(2-mercapto-4-pyrimidinyl)-4-methylphenyl]-2-methylpropanamide and 2.5 g triethylamine in 20 mL anhydrous acetonitrile, and the reaction mixture was stirred under a dry ice condenser while exposed to a sun lamp for 4 h. The reaction mixture was diluted with 100 mL ether and washed successively with water, 1N sodium hydroxide solution, and brine. The organic layer was dried over magnesium sulfate, filtered, and evaporated to dryness. The crude product was purified by chromatography on silica gel using 40:1 chlorobutane/ethyl acetate mixture as eluent to yield 0.52 g of the title compound as yellow crystals melting at 114°–116° C. $^1$H NMR (CDCl$_3$): δ 1.21 (d,6H), 2.40 (s,3H), 2.55 (m,1H), 7.40–8.70 (5H), 10.7(s, 1H,NH).

EXAMPLE 8

Preparation of N-[2-[2-[(difluoromethyl)thiol]4-pyrimidinyl]4-methylphenyl]-2-methylpropanamide 0.290 g (0.001 mol) N-[2-(2-mercapto-4-pyrimidinyl)4-methylphenyl]-2-methylpropanamide was dissolved in 10 mL 5% sodium hydroxide solution, 5 mL dioxane and 0.030 g tetrabutylammonium hydrogen sulfate were then added, and difluorodichloromethane was bubbled through at slow rate for 5 min with slight exothermic reaction. The reaction mixture was further stirred at room temperature for 2 h after which it was diluted with 50 mL ether, washed with water and brine, dried over magnesium sulfate, filtered, and evaporated to dryness. The crude product was purified by chromatography on silica gel using 20:1 chlorobutane/ethyl acetate mixture as eluent to yield 0.20 g of the rifle compound as yellow crystals melting at 128°–130° C. $^1$H NMR (CDCl$_3$): δ 1.21 (d,6H), 2.40 (s,3H), 2.55 (m,1H), 7.40–8.00 (t,1H), 7.40–8.60 (5H), (11.0 (s,1H,NH).

EXAMPLE 9

Preparation of 2,2-dimethyl-N-[4-methyl-2-[2-(2,2, 2-trifluoroethoxy)-4-pyrimidinyl]phenyl] propanamide 0.10 g sodium metal was covered under nitrogen with 15 mL anhydrous tetrahydrofuran and 1 g trifluoroethanol was added dropwise with stirring. Stirring was continued for 1.5 h at which time the sodium was completely reacted. A solution of 0.4 g 2,2-dimethyl-N-[4-methyl-2-[2-(methylsulfonyl)-4-pyrimidinyl]phenyl]propanamide was added via syringe and stirring continued overnight under nitrogen. The reaction mixture was quenched with water and extracted with ether. The organic extracts were washed with water and brine, dried over magnesium sulfate, filtered, and evaporated to dryness. The crude product was purified by chromatography on silica gel using 40:1 chlorobutane/ethyl acetate mixture as eluent to yield 0.38 g of the title compound as white crystals melting at 126°–128° C. $^1$H NMR (CDCl$_3$): δ 1.28 (s,9H), 2.40 (s,3H), 4.85 (q,2H), 7.30–8.6 (5H), 11.9(s,1H,NH).

EXAMPLE 10

Preparation of N-[2-(6-bromo-2-pyridinyl)-4-methylphenyl]-2,2-dimethylpropanamide.

A mixture of 24 g (0.1 mol) 2,6-dibromopyridine, 0.250 g palladium bis(triphenylphosphine) dichloride, and 40 mL dimethoxyethane was stirred under nitrogen for 20 min, after which 12 g (0.05 mol) N-(2-borono4-methylphenyl)-2,2-dimethylpropanamide and a solution of 26 g sodium bicarbonate in 300 mL water was added, and the mixture heated to reflux for 5 h. After cooling to 50° C., 50 mL ethyl acetate was added and stirred until it reached room temperature. The reaction mixture was diluted with 300 mL ethyl acetate and washed successively with water and brine. The organic extracts were dried over magnesium sulfate, filtered, and evaporated to dryness. The crude product was purified by chromatography on silica using 20:1 chlorobutane/ethyl acetate mixture as eluent to yield 13.1 g of the title compound as light tan crystals melting at 120°–126° C. $^1$H NMR (CDCl$_3$): δ 1.28 (s,9H), 2.40 (s,3H), 7.30–8.4 (6H), 10.9 (s,1H,NH).

Starting 2,6-dibromopyridine was isolated as a fast running peak. A small amount of bis-coupling product, N,N'[2, 6-pyridinediylbis-(4-methyl-2,1-phenylene)]bis[2,2-dimethylpropanamide] melting at 181°–184° C. was also obtained as a slower running peak. $^1$H NMR (CDCl$_3$): δ 1.28 (s, 18H), 2.40 (s,6H), 7.30–8.4 (9H), 10.7 (s,2H,NH).

EXAMPLE 11

Preparation of N-[4-bromo-2-[2-(trifluoromethyl)-4-pyrimidinyl]phenyl]-2,2-dimethylpropanamide 3 g N-[2-[2-(trifluoromethyl)4-pyrimidinyl]phenyl]-2,2-dimethylpropanamide was dissolved in 30 mL glacial acetic acid, 5 g anhydrous sodium acetate was added, and a solution of 2.8 g bromine in 5 mL acetic acid was added dropwise with stirring over 1 h. The reaction mixture was stirred at room temperature overnight, after which it was diluted with water. The precipitate was collected by filtration, washed well with water, then with hexane, and was dried in a vacuum oven overnight to yield 3.3 g of the title compound melting at 153°–157° C. $^1$H NMR (CDCl$_3$): δ 1.28 (s,9H), 7.40–8.4 (6H), 10.6 (s,1H,NH).

EXAMPLE 12

Preparation of 2,2-dimethyl-N-[4-methyl-2-[6-(trifluoromethyl)-2-pyrazinyl)]phenyl]propanamide Step A: N-[2-(6-Chloro-2-pyrazinyl)-4-methylphenyl]-2,2-dimethylpropanamide To a stirred mixture of the title compound from Example 1 (3.9 g, 0.017 mol), 2,6-dichloropyrazine (10.0 g, 0.067 mol) and tetrakis(triphenylphospine)-palladium(0) (0.05 g) in glyme (ethylene glycol dimethyl ether, 150 mL) was added aqueous 1M sodium carbonate (67 mL), 0.067 mol). The mixture was heated to reflux and for 8 h. After cooling to room temperature, the mixture was poured into brine (300 mL). The layers were separated and the aqueous phase extracted with three 150 mL-portions of ethyl acetate. The combined organic layers were dried (MgSO$_4$) and evaporated. The residue was chromatographed on silica gel eluting with 20% ethyl acetate/hexane to furnish 4.0 g (78% of theory) of the title compound as a white solid melting at 80°–83° C. $^1$H NMR (300 MHz, CDCl$_3$) δ 10.75 (br s, 1H), 8.91 (s, 1H), 8.51–8.56 (m, 1H), 8.39–8.41 (m,1H), 7.46 (s, 1H), 7.29–7.33 (m, 1H), 2.40 (s, 3H), 1.32 (s, 9H).

Step B: N-[2-(6-Bromo-2-pyrazinyl)-4-methylphenyl]-2,2-dimethyl-propanamide

The product from Step A (2.0 g, 6.6 mmol) was dissolved in a 30% solution of hydrobromic acid/acetic acid (18.0 mL). This mixture was stirred at room temperature for four days. The mixture was poured into aqueous 1M sodium carbonate (150 mL) and then extracted with ethyl acetate (5×50 mL). The combined extracts were dried (MgSO$_4$) and then evaporated. The solid residue was recrystallized from hexane to afford 1.0 g (45%) of the title compound melting at 74°–76° C. $^1$H NMR (400 MHz, CDCl$_3$) δ 10.64 (br s, 1H), 8.92 (s, 1H), 8.66 (s, 1H), 8.38 (m, 1H), 729–7.43 (s, 1H), 7.29–7.32 (m, 1H), 2.39 (s, 3H), 1.33 (s, 9H). Mass spec (EI) m/e 349 (1XBr).

Step C: 2,2-Dimethyl-N-[4-methyl-2-[6-(trifluoromethyl)-2-pyrazinyl]phenyl]propanamide The product obtained from Step B (0.8 g, 2.3 mmol) was dissolved in N-methylpyrrolidinone (16 mL). Cuprous iodide (1.7 g, 9.2 mmol) and sodium trifluoroacetate (2.5 g, 18.4 mmol) were then added and the resultant mixture heated at 180° C. for 6 h. After cooling to room temperature, diethyl ether (200 mL) and water (100 mL) were added. The two-phase mixture was filtered through a pad of Celite and the filter cake subsequently washed with three 50 mL-portions of ether. The layers of the filtrate were separated and the ether layer dried (MgSO$_4$). The ethereal solution was evaporated and the residue chromatographed on silica gel eluting with 15% ethyl acetate/hexane. In this manner, 0.14 g (18%) of the title compound was obtained as a yellow semisolid. $^1$H NMR (300 MHz,CDCl$_3$) δ 10.25 (br s,1H), 9.18 (s,1H), 8.93 (s,1H), 8.33–8.35 (m,1H), 7.41 (s, 1H), 7.33–7.35 (m,1H), 2.41 (s,3H), 1.25 (s,9H). $^{19}$F NMR (282 MHz, CDCl$_3$) δ 67.2.

EXAMPLE 13

Preparation of
N-[4-methyl-2-[4-(trifluoromethyl)-2-thiazolyl]-phenyl]cyclopropanecarboxamide Step A: 5-Methyl-2-nitrobenzamide 5-methyl-2-nitrobenzoic acid (25.0 g, 0.14 mol) was dissolved in diethyl ether (280 mL). To this solution at room temperature was added oxalyl chloride (12.1 mL, 0.14 mol) followed by a catalytic amount of N, N-dimethylformamide (4–5 drops). The solution was stirred for 2 h at room temperature. The reaction mixture was concentrated to give a quantitative yield of the acid chloride. This material was not purified further and was stored as a one molar solution in dichloromethane.

69 mL of the stock solution above (13.8 g, 0.069 mol of acid chloride) was added dropwise to a stirred methanolic solution of ammonia (Aldrich, 2M, 69 mL, 0.138 mol) at 0° C. After the addition was complete, the mixture was allowed to warm to room temperature and then stirred overnight. The solvents were removed under vacuum and the residue taken up in ethyl acetate (500 mL). The organic solution was washed with water (2×250 mL) and dried (MgSO$_4$). Concentration of the extracts and recrystallization of the residual solid from acetonitrile afforded 9.43 g (76% yield) of the title compound as a yellow solid melting at 172°–175° C. $^1$H NMR (400 MHz, DMSO-d$_6$) δ 8.07 (br s, 1H), 7.91–7.93 (m, 1H), 7.65 (br s, 1H), 7.45–7.47 (m, 1H), 7.43 (s, 1H), 2.42 (s, 3H).

Step B: 5-Methyl-2-nitrobenzenecarbothioamide 7.0 g (0.040 mol) of the product from Step A was suspended in toluene (140 mL). Lawesson's reagent (9.4 g, 0.023 mol) was added and the resulting mixture heated at 100° for 3 h (the mixture became homogeneous at 85° C.).

After cooling to room temperature, the toluene was removed on the rotary evaporator. The residue was flash chromatographed on silica gel eluting with 20% ethyl acetate/hexane to furnish 7.2 g (95% yield) of the title compound as a yellow semisolid. $^1$H NMR (400 MHz, CDCl$_3$) δ 7.92–7.94 (d,1H), 7.93 (br s, 1H, overlap with doublet), 7.25–7.32 (m,2H), 7.17 (br s, 1H), 2.45 (s,3H).

Step C: 4,5-Dihydro-2-(5-methyl-2-nitrophenyl)-4-(trifluoromethyl)-4-thiazolol

The product from Step B (5.5 g, 0.028 mol) was dissolved in ethyl alcohol (100 mL). 3-bromo-1,1,1-trifluoroacetone (5.3 g, 0.028 mol) was added and the resulting solution refluxed for 3 h. After cooling to room temperature, the reaction mixture was evaporated to dryness. The residue was partitioned between ethyl acetate and 10% aqueous sodium carbonate (200 mL each). The organic layer was separated, dried (MgSO$_4$) and then concentrated to give an oil. Flash chromatography of this oil on silica gel eluting with 20% ethyl acetate/hexane afforded a solid which was further purified by recrystallization from chlorobutane/hexane. Yield: 4.4 g (51%) of the title compound as a white solid melting at 148°–151° C. $^1$H NMR (300 MHz, CDCl$_3$) δ 7.96–7.98 (m,1H), 7.42–7.44 (m,2H), 3.86–3.89 (m,1H), 3.34 (s,1H), 2.49 (s,3H).

Step D: 2-(5-Methyl-2-nitrophenyl)-4-(trifluoromethyl)thiazole

The tertiary alcohol (3.9 g, 0.013 mol) obtained in Step C was refluxed for 3 h in toluene (60 mL) in the presence of a catalytic amount of p-toluenesulfonic acid (0.2 g). Azeotropic removal of water was achieved by employing a Dean-Starke trap. After cooling to room temperature, the toluene was removed under vacuum. The residue was taken up in ethyl acetate (200 mL) and washed with 10% aqueous sodium carbonate and brine (100 mL each). The dried (MgSO$_4$) solution was concentrated to give 2.5 g (68% yield) of the title compound as white solid melting at 98°–104° C. $^1$H NMR (300 MHz, CDCl$_3$) δ 7.91–7.94 (m,2H), 7.53 (s,1H), 7.43–7.46 (m,1H), 2.51 (s,3H).

Step E: 4-Methyl-2-[4-(trifluoromethyl)-2-thiazolyl]benzenamine

The product from Step D (3.1 g, 0.011 mol) was suspended in a mixture of glacial acetic acid (15 mL) and water (5 mL). The mixture was heated on a steam bath to a temperature of 65° C. Iron powder (1.9 g, 0.035 mol) was then added in small portions (exothermic). Care was taken during the addition to ensure that the temperature did not exceed 75° C. Once the iron had been added, heating at 75° C. was continued for another 10 min. The reaction mixture was hot-filtered onto 30 g cracked ice. After the ice melted, the aqueous mixture was extracted with dichloromethane (3×20 mL). The combined extracts were washed with saturated sodium bicarbonate and brine (30 mL each). The dried (MgSO$_4$) solution was concentrated to furnish 1.4 g (53% yield) of the title compound as a white solid melting at 100°–103° C. $^1$H NMR (400 MHz, CDCl$_3$) δ 7.62 (s,1H), 7.39 (s,1H), 7.03–7.05 (m,1H), 6.69–6.71 (m,1H), 5.82 (br s,2H), 2.28 (s,3H).

Step F: N-[4-Methyl-2-[4-trifluoromethyl)-2-thiazolyl]phenyl]cyclopropanecarboxamide To a stirred solution of the product obtained in Step E (0.46 g, 1.8 mmol) and triethylamine (250 μL, 1.8 mmol) in anhydrous tetrahydrofuran (THF, 15 mL) cooled to 0° C.

was added dropwise a solution of cyclopropanecarbonyl chloride (160 μL, 1.8 mmol) in THF (5 mL). The mixture was stirred at 0° C. for 30 min and then at room temperature overnight. The reaction mixture was filtered and the solids were washed with ethyl acetate. The filtrate was evaporated to dryness and the residue purified by recrystallization from hexane to yield 0.41 g (71% yield) of the title compound as a white solid melting at 155°–156° C. $^1$H NMR (400 MHz, CDCl$_3$) δ 11.75 (s,1H), 8.61–8.63 (m,1H), 7.76 (s, 1H), 7.55 (s,1H), 7.26–7.27 (m,1H), 2.37 (s,3H), 1.56–1.62 (m,2H), 1.07–1.13 (m,2H).

Examples of compounds of the invention are shown in Tables 1–5.

TABLE 1

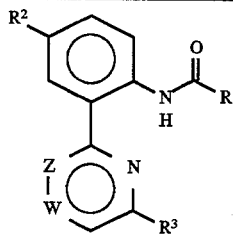

wherein R is XR$^1$ $R^2 = CH_3$, $R^3 = CF_3$, W = CH, Z = CH, R=

| | | | | |
|---|---|---|---|---|
| CH$_3$ | CH$_2$SCH$_3$ | CH$_2$CH$_2$Br | C(CH$_3$)=CH$_2$ | CH(CH$_3$)$_2$ |
| CH$_2$F | (CH$_2$)$_4$CH$_3$ | (CH$_2$)$_3$CH$_3$ | CH(CH$_3$)$_2$Br | CH=C(CH$_3$)$_2$ |
| CH$_2$CH$_3$ | cyclopropyl | CHBrCH(CH$_3$)$_2$ | C(CH$_3$)$_2$SCH$_3$ | CH(CH$_3$)CH$_2$Cl |
| CH$_2$Br | cyclobutyl | CH=C(CH$_2$Cl)$_2$ | CH$_2$C(CH$_3$)=CH$_2$ | C(CH$_3$)=CHBr |
| CHCl$_2$ | OCH$_2$CH$_3$ | CH$_2$-cyclopropyl | CH$_2$CH(CH$_3$)$_2$ | 1-Me-cyclopropyl |
| OCH$_3$ | C(CH$_3$)$_3$ | CH$_2$OCH$_3$ | CHBrCH$_3$ | OCH(CH$_3$)$_2$ |
| CF$_3$ | CH$_2$CH$_2$Cl | C(CH$_3$)$_2$OCH$_3$ | 2-Me-cyclopropyl | CH(CH$_3$)SCH$_3$ |

$R^2 = CH_2CH_3$, $R^3 = CF_3$, W = CH, Z = CH, R=

| | | | | |
|---|---|---|---|---|
| CH$_2$CHCl$_2$ | CH(CH$_3$)$_2$ | cyclopropyl | OCH(CH$_3$)$_2$ | 1-Me-cyclopropyl |
| C(CH$_3$)$_3$ | CH$_2$CH$_2$CF$_3$ | C(CH$_3$)$_2$CH$_2$Cl | CH$_2$CH(CH$_3$)$_2$ | 2-Me-cyclopropyl |

$R^2 = CH_3$, $R^3 = Br$, W = CH, Z = CH, R=

| | | | |
|---|---|---|---|
| CH(CH$_3$)$_2$ | cyclopropyl | CH$_2$CH(CH$_3$)$_2$ | CH=C(CH$_3$)$_2$ |
| C(CH$_3$)$_3$ | CHFCH$_3$ | CH(CH$_3$)CH$_2$CH$_3$ | CH=C(CH$_2$Cl)$_2$ |
| CCl$_2$CH$_3$ | CHCl$_2$ | C(CH$_3$)$_2$OCH$_3$ | CH(CH$_3$)SCH$_3$ |
| C(CH$_3$)$_2$Br | | 2-Me-cyclopropyl | OCH(CH$_3$)$_2$ |

$R^2 = CH_3$, $R^3 = Cl$, W = CH, Z = CH, R=

| | | | | |
|---|---|---|---|---|
| CH(CH$_3$)$_2$ | CH(CH$_3$)SCH$_3$ | cyclopropyl | OCH(CH$_3$)$_2$ | CH$_2$CH(CH$_3$)$_2$ |
| CHCl$_2$ | 1-Me-cyclopropyl | C(CH$_3$)$_2$OCH$_3$ | C(CH$_3$)$_3$ | CH$_2$CHCl$_2$ |
| | 2-Me-cyclopropyl | CH$_2$CH(CH$_3$)=CH$_2$ | C(CH$_3$)$_2$Br | CH=C(CH$_3$)$_2$ |

| R | R$^2$ | R | R$^2$ |
|---|---|---|---|
| \multicolumn{4}{c}{$R^3 = CF_3$, W = CH, Z = CH} |
| CHClCH$_3$ | H | cyclobutyl | Br |
| CH(CH$_3$)$_2$ | H | CH$_2$CHF$_2$ | Br |
| C(CH$_3$)$_3$ | H | CH(CH$_3$)$_2$ | NO$_2$ |
| CF$_3$ | H | CH$_2$CH(CH$_3$)$_2$ | NO$_2$ |
| CH(CH$_3$)$_2$ | Br | C(CH$_3$)$_3$ | NO$_2$ |
| C(CH$_3$)$_3$ | Br | CH$_2$OCH$_3$ | OCH$_3$ |
| cyclopropyl | Br | C(CH$_3$)$_2$OCH$_3$ | SCH$_3$ |
| 1-Me-cyclopropyl | Br | Ph | CH$_3$ |
| OCH(CH$_3$)$_2$ | Br | | |
| \multicolumn{4}{c}{$R^3 = Br$, W = CH, Z = CH} |
| CH$_2$CHCl$_2$ | H | 1-Me-cyclopropyl | CH$_2$CH$_3$ |
| C(CH$_3$)$_2$CH$_2$Cl | H | CF$_3$ | CH$_2$CH$_3$ |
| CH(CH$_3$)$_2$ | H | C(CH$_3$)$_3$ | Br |
| C(CH$_3$)$_3$ | H | CH$_2$SCH$_3$ | CH$_2$SCH$_3$ |
| cyclopropyl | SCH$_3$ | | |
| \multicolumn{4}{c}{$R^3 = Cl$, W = CH, Z = CH} |
| CH(CH$_3$)CH$_2$CH$_3$ | H | CH=C(CH$_2$Cl)$_2$ | H |
| CHFCH$_3$ | CH$_2$CH$_3$ | CH=C(CH$_3$)$_2$ | CH$_2$OCH$_3$ |
| CCl$_2$CH$_3$ | CH$_2$CH$_3$ | CH(CH$_3$)$_2$ | NO$_2$ |
| C(CH$_3$)$_2$CH$_2$Cl | H | | |

TABLE 1-continued wherein R is XR¹

| R | R² | R³ | R | R² | R³ |
|---|---|---|---|---|---|
| W = CH, Z = CH | | | | | |
| C(CH₃)₃ | CH₃ | SCH₃ | 1-Me-cyclopropyl | OCH₃ | SCF₃ |
| CH(CH₃)₂ | CH₃ | SCH₃ | 2-Me-cyclopropyl | OCH₃ | SCF³ |
| CF₃ | CH₃ | SCH₃ | CH₂CH(CH₃)₂ | NO₂ | SCHF₂ |
| cyclobutyl | CH₃ | SCH₃ | C(CH₃)₃ | OCH₂CH₃ | SCHF₂ |
| W = N, Z = CH | | | | | |
| C(CH₃)₃ | CH₃ | Cl | CF₃ | NO₂ | Br |
| CH₃ | CH₃ | Cl | OCH(CH₃)₂ | H | Br |
| CH₂CH₃ | CH₂CH₃ | Cl | C(CH₃)₃ | CH₃ | CF₃ |
| (CH₂)₃CH₃ | H | Cl | cyclopropyl | CH₃ | CF₃ |
| (CH₂)₄CH₃ | Br | Cl | CF₃ | OCH₃ | CF₃ |
| CH(CH₃)₂ | CH₃ | Cl | OCH(CH₃)₂ | CH₃ | CF₃ |
| CH₂CH(CH₃)₂ | Br | Cl | cyclobutyl | H | CF₃ |
| C(CH₃)₂OCH₃ | CH₃ | Cl | 1-Me-cyclopropyl | CH₂CH₃ | CF₃ |
| CH₂SCH₃ | CH₃ | Cl | cyclopropyl | CH₃ | SCF₃ |
| cyclopropyl | NO₂ | Cl | CH(CH₃)₂ | CH₃ | SCF₃ |
| CF₃ | SCH₃ | Cl | cyclobutyl | SCH₃ | SCF₃ |
| OCH(CH₃)₂ | CH₃ | Cl | C(CH₃)₃ | Br | SCF₃ |
| C(CH₃)₃ | CH₃ | Br | cyclopropyl | Br | SCF₃ |
| CH(CH₃)₂ | CH₃ | Br | OCH(CH₃)₂ | H | SCF₃ |
| CH₂F | CH₃ | Br | cyclopropyl | CH₃ | SCHF₂ |
| CH(CH₃)SCH₃ | CH₂CH₃ | Br | CF₃ | SCH₃ | SCHF₂ |
| 2-Me-cyclopropyl | H | Br | OCH(CH₃)₂ | CH₃ | SCHF₂ |
| cyclopropyl | NO₂ | Br | cyclobutyl | CH₂CH₃ | SCHF₂ |
| CHF₂ | SCH₃ | Br | 1-Me-cyclopropyl | H | SCHF₂ |
| OCH₂CH₃ | CH₃ | Br | cyclopropyl | OCH₃ | NO₂ |

TABLE 2 wherein R is XR¹

| R | R² | R³ | R | R² | R³ |
|---|---|---|---|---|---|
| Z = CH | | | | | |
| CH(CH₃)₂ | CH₃ | CF₃ | CH(CH₃)₂ | CH₃ | SCH₃ |
| CH₂CH(CH₃)₂ | CH₃ | CF₃ | CH₂CH(CH₃)₂ | H | SCH₃ |
| C(CH₃)₃ | CH₃ | CF₃ | C(CH₃)₃ | CH₃ | SCH₃ |
| C(CH₃)OCH₃ | H | CF₃ | C(CH₃)OCH₃ | H | SCH₃ |
| CHFCH₃ | CH₃ | CF₃ | CHFCH₃ | CH₂CH₃ | SCH₃ |
| CF₃ | CH₃ | CF₃ | CF₃ | CH₃ | SCH₃ |
| CH₂CHCl₂ | H | SCH₃ | CCl₂CH₃ | CH₃ | SCH₃ |
| C(CH₃)₂Br | CH₃ | SCH₃ | C(CH₃)₂CH₂Cl | CH₂CH₃ | SCH₃ |
| cyclopropyl | CH₃ | SCH₃ | 1-Me-cyclopropyl | CH₃ | SCH₃ |
| 2-Me-cyclopropyl | CH₃ | SCH₃ | CH=C(CH₃)₂ | CH₃ | SCH₃ |
| CH=C(CH₂Cl)₂ | CH₃ | SCH₃ | CH(CH₃)₂ | CH₃ | SCHF₂ |
| OCH(CH₃)₂ | CH₃ | SCH₃ | CH(CH₃)₂ | CH₃ | SCF₃ |

TABLE 2-continued

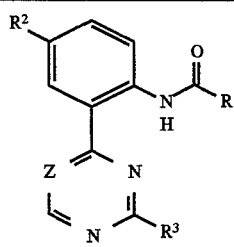

wherein R is XR¹

| R | R² | R³ | R | R² | R³ |
|---|---|---|---|---|---|
| C(CH₃)₃ | CH₃ | SCHF₂ | CF₃ | CH₃ | SCF₃ |
| C(CH₃)₃ | CH₃ | SCF₃ | CH=C(CH₃)₂ | SCH₃ | SCF₃ |
| C(CH₃)₃ | OCH₃ | SCF₃ | 2-Me-cyclopropyl | CH₂OCH₃ | NO₂ |
| cyclopropyl | CH₃ | NO₂ | CH(CH₃)₂ | Br | Cl |
| C(CH₃)₃ | CH₃ | Cl | cyclopropyl | CH₃ | Cl |
| CF₃ | CH₂CH₃ | Cl | CH₂CH(CH₃)₂ | CH₃ | Cl |
| 1-Me-cyclopropyl | Cl | Cl | CH=C(CH₃)₂ | CH₃ | Cl |
| cyclopropyl | NO₂ | Cl | cyclopropyl | CH₃ | OCH₂CF₃ |
| C(CH₃)₃ | CH₃ | OCH₂CF₃ | CH₂CH(CH₃)₂ | OCH₃ | OCF₃ |
| CH(CH₃)₃ | CH₃ | OCF₃ | CHFCH₃ | CH₃ | OCF₃ |
| C(CH₃)OCH₃ | CH₃ | OCF₃ | C(CH₃)₂Br | CH₂CH₃ | OCF₃ |
| CCl₂CH₃ | CH₃ | OCF₃ | cyclopropyl | CH₃ | OCF₃ |
| C(CH₃)₃ | Cl | OCF₃ | CH(CH₃)₂ | CH₃ | NO₂ |
| CH=C(CH₃)₂ | Br | OCF₃ | | | |
| cyclobutyl | CH₃ | NO₂ | CF₃ | CH₂CH₃ | NO₂ |
| OCH(CH₃)₂ | Br | NO₂ | cyclopropyl | Cl | NO₂ |
| C₆H₅ | CH₃ | CF₃ | | | |
| | | Z = N | | | |
| CH(CH₃)₂ | CH₃ | CF₃ | CH₂CH(CH₃)₂ | CH₃ | CF₃ |
| C(CH₃)₃ | CH₃ | CF₃ | CHFCH₃ | CH₃ | CF₃ |
| CF₃ | CH₃ | CF₃ | OCH(CH₃)₂ | Br | CF₃ |
| cyclopropyl | CH₂CH₃ | CF₃ | 2-Me-cyclopropyl | NO₂ | CF₃ |
| CH(CH₃)₂ | Cl | CF₃ | OCH(CH₃)₂ | Cl | CF₃ |
| C(CH₃)₃ | CN | CF₃ | CH(CH₃)₂ | CH₃ | SCH₃ |
| CF₃ | CH₃ | SCH₃ | CH₂CHCl₂ | Br | SCH₃ |
| CH(CH₃)₂ | CH₃ | SCHF₂ | C(CH₃)₃ | CH₃ | SCHF₂ |
| CH(CH₃)₂ | CH₃ | SCF₃ | C(CH₃)₃ | CH₃ | SCF₃ |
| CH₂CH(CH₃)₂ | CH₃ | SCF₃ | OCH(CH₃)₂ | CH₃ | SCF₃ |
| CF₃ | CH₃ | SCF₃ | cyclopropyl | Br | SCF₃ |
| 1-Me-cyclopropyl | NO₂ | SCF₃ | CH(CH₃)₂ | Cl | SCF₃ |
| C(CH₃)₃ | CH₂CH₃ | SCF₃ | C(CH₃)₃ | CH₃ | Cl |
| CH(CH₃)₂ | CH₃ | Cl | CH₂CH(CH₃)₂ | CH₃ | Cl |
| C(CH₃)₃ | CH₃ | Cl | CHFCH₃ | CH₃ | Cl |
| CF₃ | CH₃ | Cl | OCH(CH₃)₂ | Br | Cl |
| cyclopropyl | CH₂CH₃ | Cl | 2-Me-cyclopropyl | NO₂ | Cl |
| CH(CH₃)₂ | Cl | Cl | OCH(CH₃)₂ | Cl | Cl |
| C(CH₃)₃ | CN | Cl | CH(CH₃)₂ | CH₃ | Br |
| CH₂CH(CH₃)₂ | CH₃ | Br | C(CH₃)₃ | CH₃ | Br |
| CHF₂ | CH₃ | Br | CF₃ | CH₃ | Br |
| OCH₃ | Br | Br | cyclopropyl | CH₂CH₃ | Br |
| 1-Me-cyclopropyl | NO₂ | Br | CH(CH₃)₂ | Cl | Br |
| OCH(CH₃)₂ | Cl | Br | OCH₂CH₃ | CN | Br |
| CF₃ | CH₃ | OCH₂CF₃ | OCH(CH₃)₂ | Br | OCH₂CF₃ |
| cyclopropyl | CH₂CH₃ | OCH₂CF₃ | CH(CH₃)₂ | Cl | OCH₂CF₃ |
| CH(CH₃)₂ | CH₃ | NO₂ | cyclobutyl | CH₃ | NO₂ |
| C₂F₅ | CH₃ | NO₂ | OCH(CH₃)₂ | Br | NO₂ |
| cyclopropyl | CH₂CH₃ | NO₂ | 2-Me-cyclopropyl | CH₃ | OCF₃ |
| CH(CH₃)₂ | CH₃ | OCF₃ | OCH(CH₃)₂ | Cl | OCF₃ |
| C(CH₃)₃ | Br | OCF₃ | | | |

TABLE 3

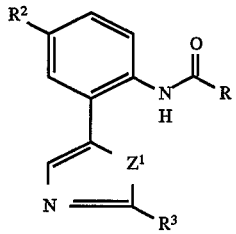

wherein R is XR¹

| R | $R^2$ | $R^3$ | R | $R^2$ | $R^3$ |
|---|---|---|---|---|---|
| $Z^1 = O$ | | | | | |
| $C(CH_3)OCH_3$ | H | $CF_3$ | $CHFCH_3$ | H | $CF_3$ |
| $CH(CH_3)_2$ | $CH_3$ | $CF_3$ | $C(CH_3)_3$ | $CH_3$ | $CF_3$ |
| cyclopropyl | $CH_3$ | $CF_3$ | $OCH(CH_3)_2$ | $CH_3$ | $CF_3$ |
| $CH_2CH(CH_3)_2$ | Br | $CF_3$ | $CF_3$ | Br | $CF_3$ |
| $C_6H_5$ | Cl | $CF_3$ | $CH_2CHCl_2$ | $NO_2$ | $CF_3$ |
| 1-Me-cyclopropyl | CN | $CF_3$ | $C(CH_3)_2Br$ | $CH_3$ | $SCH_3$ |
| 2-Me-cyclopropyl | H | $SCH_3$ | $CH(CH_3)_2$ | $CH_3$ | $SCHF_2$ |
| $C(CH_3)_3$ | H | $SCF_3$ | $CH(CH_3)_2$ | $CH_3$ | $SCF_3$ |
| $CF_3$ | Cl | $SCF_3$ | $C(CH_3)_3$ | $OCH_3$ | $SCF_3$ |
| $CH=C(CH_3)_2$ | $SCH_3$ | $SCF_3$ | cyclopropyl | $CH_3$ | $NO_2$ |
| cyclobutyl | H | $NO_2$ | $CH_2CF_3$ | $CH_3$ | $NO_2$ |
| $CH(CH_3)_2$ | Br | Cl | $CF_3$ | $CH_2CH_3$ | Cl |
| cyclopropyl | $CH_3$ | Cl | $OCH_2CH_3$ | $CH_3$ | Br |
| $CH_2CF_3$ | Br | Br | cyclopropyl | $CH_3$ | $OCH_2CF_3$ |
| $CH(CH_3)_2$ | $CH_3$ | $OCF_3$ | cyclopropyl | $CH_3$ | $OCF_3$ |
| $CH_2CH(CH_3)_2$ | $OCH_3$ | $OCF_3$ | $OCH_3$ | $CH_2CH_3$ | $CF_2Cl$ |
| $CH(CH_3)_2$ | $CH_3$ | $CF_2Cl$ | cyclobutyl | Br | $CF_2Cl$ |
| $Z^1 = S$ | | | | | |
| $C(CH_3)_3$ | H | $CF_3$ | $CH(CH_3)_2$ | $SCH_3$ | $CF_3$ |
| cyclopropyl | $CH_3$ | $CF_3$ | $CF_3$ | Br | $CF_3$ |
| $C_6H_5$ | Cl | $CF_3$ | $CH(CH_3)_2$ | $CH_3$ | $SCHF_2$ |
| cyclobutyl | H | $SCF_3$ | $CH(CH_3)_2$ | $CH_3$ | $SCF_3$ |
| $C(CH_3)_3$ | $SCH_3$ | $SCF_3$ | 2-Me-cyclopropyl | $CH_2OCH_3$ | $NO_2$ |
| $CH(CH_3)_2$ | $CH_3$ | $NO_2$ | cyclopropyl | $CH_3$ | Br |
| $OCH(CH_3)_2$ | Br | Br | $CH_2CH(CH_3)_2$ | CN | Cl |
| 1-Me-cyclopropyl | $NO_2$ | Cl | $C(CH_3)_3$ | Cl | $OCF_3$ |
| $CH=C(CH_3)_2$ | Br | $OCF_3$ | $CH(CH_3)_2$ | $CH_3$ | $OCHF_2$ |
| cyclopropyl | $CH_3$ | $CF_2Cl$ | $C_6H_5$ | H | $CF_2Cl$ |

TABLE 4

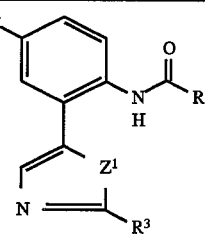

wherein R is XR¹

| R | $R^2$ | $R^3$ | R | $R^2$ | $R^3$ |
|---|---|---|---|---|---|
| $Z^1 = O$ | | | | | |
| $C(CH_3)_3$ | H | $CF_3$ | $OCH_3$ | H | $CF_3$ |
| $CH(CH_3)_2$ | $CH_3$ | $CF_3$ | $OCH(CH_3)_2$ | $CH_3$ | $CF_3$ |
| $CH_2CH(CH_3)_2$ | Cl | $CF_3$ | $CF_3$ | Cl | $CF_3$ |
| 1-Me-cyclopropyl | Cl | $CF_3$ | $C_6H_5$ | Br | $CF_3$ |
| $CH_2CHCl_2$ | $NO_2$ | $CF_3$ | 1-Me-cyclopropyl | C | $CF_3$ |
| $C(CH_3)_2Br$ | $CH_3$ | $SCH_3$ | $CH(CH_3)_2$ | $CH_3$ | $SCHF_2$ |
| $C(CH_3)_3$ | H | $SCF_3$ | $CH=C(CH_3)_2$ | $SCH_3$ | $SCF_3$ |
| $CH(CH_3)_2$ | Br | $SCF_3$ | $CF_3$ | Cl | $SCF_3$ |
| $CH(CH_3)_2$ | Br | Cl | $CF_3$ | $CH_2CH_3$ | Cl |
| cyclopropyl | $CH_3$ | Cl | $OCH_2CH_3$ | $CH_3$ | Br |

TABLE 4-continued

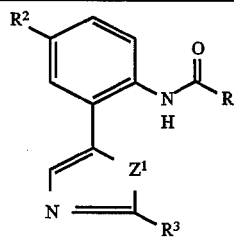

wherein R is XR¹

| R | R² | R³ | R | R² | R³ |
|---|----|----|---|----|----|
| $CH_2CF_3$ | Br | Br | $OCH(CH_3)_2$ | $CH_3$ | $OCH_2CF_3$ |
| $OCH_3$ | $CH_2CH_3$ | $OCF_3$ | $CH(CH_3)_2$ | $CH_3$ | $OCF_3$ |
| cyclobutyl | Br | $OCF_3$ | $CH(CH_3)_2$ | $CH_3$ | $CF_2Cl$ |
| cyclopropyl | $CH_3$ | $CF_2Cl$ | $CH_2CH(CH_3)_2$ | $OCH_3$ | $CF_2Cl$ |
| cyclopropyl | $CH_2CH_3$ | $NO_2$ | $CH(CH_3)_2$ | $CH_3$ | $NO_2$ |

$Z^1 = S$

| R | R² | R³ | R | R² | R³ |
|---|----|----|---|----|----|
| $C(CH_3)_3$ | H | $CF_3$ | $CH_3$ | $CH_3$ | $CF_3$ |
| cyclopropyl | $CH_3$ | $CF_3$ | $CH_2CH(CH_3)_2$ | $CH_3$ | $CF_3$ |
| $CF_3$ | Br | $CF_3$ | $C_6H_5$ | Cl | $CF_3$ |
| $CH(CH_3)_2$ | $CH_3$ | $SCHF_2$ | cyclobutyl | H | $SCF_3$ |
| $CH(CH_3)_2$ | $CH_3$ | $SCF_3$ | $C(CH_3)_3$ | $SCH_3$ | $SCF_3$ |
| cyclopropyl | $CH_3$ | $NO_2$ | cyclobutyl | H | $NO_2$ |
| $CH_2CF_3$ | $CH_3$ | $NO_2$ | $C(CH_3)_3$ | $CH_3$ | Br |
| $CH(CH_3)_2$ | H | Br | $OCH_2CH_3$ | $NO_2$ | Br |
| $CH_2CH(CH_3)_2$ | CN | Cl | 1-Me-cyclopropyl | $CH_3$ | Cl |
| cyclopropyl | $CH_3$ | $OCF_3$ | $C_6H_5$ | CN | $OCF_3$ |
| $OCH(CH_3)_2$ | $CH_3$ | $OCHF_2$ | $C(CH_3)_3$ | $NO_2$ | $CF_2Cl$ |
| $CH=(CH_3)_2$ | Br | $CF_2Cl$ | $C(CH_3)_3$ | $CH_3$ | CN |

W = S, Z = CH

| R | R² | R³ | R | R² | R³ |
|---|----|----|---|----|----|
| $C(CH_3)_3$ | H | $CF_3$ | $OCH_3$ | H | $CF_3$ |
| $C(CH_3)_3$ | $CH_3$ | $SCH_3$ | $CH(CH_3)_2$ | $CH_3$ | $CF_3$ |
| $OCH(CH_3)_2$ | $CH_3$ | $CF_3$ | $CH_2CH(CH_3)_2$ | Cl | $CF_3$ |
| $CF_3$ | Cl | $CF_3$ | 1-Me-cyclopropyl | Cl | $CF_3$ |
| $C_6H_5$ | Br | $CF_3$ | $CH_2CHCl_2$ | $NO_2$ | $CF_3$ |
| 1-Me-cyclopropyl | CN | $CF_3$ | $CH(CH_3)_2$ | $CH_3$ | $SCHF_2$ |
| $C(CH_3)_3$ | $CH_3$ | $SCH_3$ | $CH=C(CH_3)_2$ | $SCH_3$ | $SCF_3$ |
| $CH(CH_3)_2$ | Br | $SCF_3$ | $CF_3$ | Cl | $SCF_3$ |
| $CH(CH_3)_2$ | Br | Cl | $CF_3$ | $CH_2CH_3$ | Cl |
| cyclopropyl | $CH_3$ | Cl | $OCH_2CH_3$ | $CH_3$ | Br |
| $CH_2CF_3$ | Br | Br | $OCH(CH_3)_2$ | CN | $OCH_2CF_3$ |
| $C(CH_3)_3$ | $CH_3$ | $OCH_2CF_3$ | $OCH_3$ | $CH_2CH_3$ | $OCF_3$ |
| $CH(CH_3)_2$ | $CH_3$ | $OCF_3$ | cyclobutyl | Br | $OCF_3$ |
| $CH(CH_3)_2$ | $CH_3$ | $CF_2Cl$ | cyclopropyl | $CH_3$ | $CF_2Cl$ |
| $CH_2CH(CH_3)_2$ | $OCH_3$ | $CF_2Cl$ | cyclopropyl | $CH_2CH_3$ | $NO_2$ |
| $CH(CH_3)_2$ | $CH_3$ | $NO_2$ | | | |

W = S, Z = N

| R | R² | R³ | R | R² | R³ |
|---|----|----|---|----|----|
| $C(CH_3)_3$ | $CH_3$ | $SCH_3$ | $CH(CH_3)_2$ | Br | $CF_3$ |
| cyclopropyl | $SCH_3$ | $CHF_2$ | $CF_3$ | H | Br |
| $CH_2CHCl_2$ | $CH_2CH_3$ | $OCF_3$ | $C_6H_5$ | Cl | $SCF_3$ |

W = O, Z = N

| R | R² | R³ | R | R² | R³ |
|---|----|----|---|----|----|
| 1-Me-cyclopropyl | Cl | $CF_2Cl$ | $CH_2CH(CH_3)_2$ | $CH_3$ | $CF_3$ |
| cyclopropyl | $CH_2CH_3$ | $NO_2$ | $CH(CH_3)_2$ | $CH_3$ | Br |
| $OCH_3$ | $CH_2CH_3$ | $OCF_3$ | $CH(CH_3)_2$ | $NO_2$ | $SCF_3$ |
| cyclobutyl | Br | $OCF_3$ | $CHBrCH_3$ | H | Cl |

Formulation/Utility

Compounds of this invention will generally be used in a formulation or a composition comprising an agriculturally suitable carrier comprising at least one of a surfactant, a liquid or solid diluent or an organic solvent. Useful formulations include dusts, films, granules, pellets, solutions, suspensions, microencapsulations, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations or compositions will typically contain effective amounts of active ingredient, diluent and surfactant within the following approximate ranges which add up to 100 percent by weight.

|  | Weight Percent | | |
|---|---|---|---|
|  | Active Ingredient | Diluent | Surfactant |
| Wettable Powders | 5–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., Handbook of Insecticide Dust Diluents and Carriers, 2nd Ed., Dorland Books, Caldwell, N.J. Typical liquid diluents and solvents are described in Marsden, Solvents Guide, 2nd Ed., Interscience, New York, 1950. McCutcheon's Detergents and Emulsifiers Annual, Allured Publ. Corp., Ridgewood, N.J., as well as Sisely and Wood, Encyclopedia of Surface Active Agents, Chemical Publ. Co., Inc., New York, 1964, list surfactants and recommended uses. All formulations can contain minor amounts of additives to reduce foam, caking, corrosion, microbiological growth, and the like.

Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., Pesticide Formulations, Washington, D.C., 1988, pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", Chemical Engineering, Dec. 4, 1967, pp 147–48, Perry's Chemical Engineer's Handbook, 4th Ed., McGraw-Hill, New York, 1963, pp 8–57 and following, and WO 91/13546. Pellets can be prepared as described in U.S. Pat. No. 4,172,714. Water-dispersible and water-soluble granules can also be prepared as taught in DE 3,246,493.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 14; Klingman, Weed Control as a Science, John Wiley and Sons, Inc., New York, 1961, pp 81–96; and Hance et at., Weed Control Handbook, 8th Ed., Blackwell Scientific Publications, Oxford, 1989.

In the following Examples, all percentages are by weight and all formulations are prepared in conventional ways. Compound numbers refer to compounds in Index Table A.

TABLE A

Example A

High Strength Concentrate

| | |
|---|---|
| Compound 1 | 98.5% |
| silica aerogel | 0.5% |
| synthetic amorphous fine silica | 1.0%. |

TABLE A-continued

Example B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| Compound 1 | 10.0% |
| attapulgite granules (low volatile matter, 0.71/0.30 mm; U.S.S. No. 25–50 sieves) | 90.0%. |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Tests results indicate that the compounds of the present invention are highly active preemergent and/or postemergent herbicides and/or plant growth regulants. Many of them have utility for broad-spectrum pre- and/or postemergence weed control in areas where complete control of all vegetation is desired such as around fuel storage tanks, industrial storage areas, parking lots, drive-in theaters, around billboards and highway and railroad structures. Some of the compounds are useful for the control of selected grass and broadleaf weeds with tolerance to important agronomic crops which include but are not limited to barley, cotton, wheat, rape, sugarbeets, corn, soybeans and rice. Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. A mixture of one or more of the following herbicides with a compound of this invention may be particularly useful for weed control. Examples of other herbicides with which compounds of this invention can be formulated are: acetochlor, acifluorfen, acrolein, 2-propenal, alachlor, ametryn, amidosulfuron, ammonium sulfamate, amitrole, anilofos, asulam, atrazine, barban, benerin, bensulfuron methyl, bensulide, bentazon, benzofluor, benzoylprop, bifenox, bromacil, bromoxynil, bromoxynil heptanoate, bromoxynil octanoate, butachlor, buthidazole, butralin, butylate, cacodylic acid, 2-chloro-N,N-di-2-propenylacetamide, 2-chloroallyl diethyldithiocarbamate, chloramben, chlorbromuron, chloridazon, chlorimuron ethyl, chlormethoxynil, chlornitrofen, chloroxuron, chlorpropham, chlorsulfuron, chlortoluron, cinmethylin, cinosulfuron, clethodim, clomazone, cloproxydim, clopyralid, calcium salt of methylarsonic acid, cyanazine, cycloate, cycluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichiobenil, dichlorprop, diclofop, diethatyl, difenzoquat, diflufenican, dimepiperate, dinitramine, dinoseb, diphenamid, dipropetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flareprop, fluazifop, fluazifop-P, fluchloralin, flumesulam, flumipropyn, fluometuron, fluorochloridone, fluorodifen, fluoroglycofen, flupoxam, fluffdone, fluroxypyr, fluzasulfuron, fomesafen, fosamine, glyphosate, haloxyfop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)acetic acid, S,S'-dimethyl-2-(difluoromethyl)4-(2-methylpropyl)-6-(trifluoromethyl)-3,5-pyridinedicarbothioate, mecoprop, mefenacet, mefluidide, methalpropalin, methabenzthiazuron, metham, methazole, methoxuron, metolachlor, metribuzin, 1,2-dihydropyridazine-3,6-dione, molinate, monolinuron, monuron, salt of monuron and trichloroacetic acid, monosodium salt of methylarsonic acid, napropamide, naptalam, neburon, nicosulfuron, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluoromethyl)phenoxy]-2-nitroacetophenone oxime-O-acetic acid methyl ester, pretilachlor, primisulfuron, procyazine, profluralin, prometon, prometryn, pronamide, propachlor, propanil, propazine, propham, prosulfalin, prynachlor, pyrazolate, pyrazon, pyrazosulfuron ethyl, quinchlorac, quizalofop ethyl, rimsulfuron, secbumeton, sethoxydim, siduron, simazine, 1-(α, α-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, tri-allate, trialkoxydim, triasulfuron, tribenuron methyl, triclopyr, tridiphane, trifluralin, trimeturon, (2,4-dichlorophenoxy)acetic acid, 4-(2,4-dichlorophenoxy)butanoic acid, vernolate, and xylachlor.

In certain instances, combinations with other herbicides having a similar spectrum of control but a different mode of action will be particularly advantageous for management of resistant weeds.

A herbicidally effective amount of the compounds of this invention is determined by a number of factors. These factors include: formulation selected, method of application, amount and type of vegetation present, growing conditions, etc. In general, a herbicidally effective amount of a compound(s) of this invention is applied at rates from about 0.001 to 20 kg/ha with a preferred rate range of 0.004 to 1.0 kg/ha. One skilled in the art can easily determine application rates necessary for the desired level of weed control.

The following Tests demonstrate the control efficacy of the compounds of this invention against specific weeds. The weed control afforded by the compounds is not limited, however, to these species. See Index Tables A–E for compound descriptions.

INDEX TABLE A

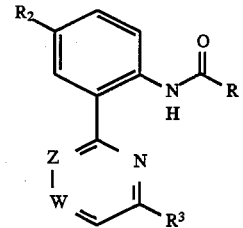

Wherein R is $XR^1$

| Cmpd. No. | R | $R^2$ | $R^3$ | W | Z | m.p. (°C.)ª |
|---|---|---|---|---|---|---|
| 1 | $CH(CH_3)_2$ | $CH_3$ | $CF_3$ | CH | CH | 114–115 |
| 2 | $CH_2CH(CH_3)_2$ | $CH_3$ | $CF_3$ | CH | CH | 74–78 |
| 3 | $C(CH_3)_3$ | $CH_3$ | $CF_3$ | CH | CH | 136–145 |
| 4 | $CF_3$ | $CH_3$ | $CF_3$ | CH | CH | 107–109 |
| 5 | cyclopropyl | $CH_3$ | $CF_3$ | CH | CH | 104–106 |
| 6 | 1-Me-cyclopropyl | $CH_3$ | $CF_3$ | CH | CH | 149–151 |
| 7 | 2-Me-cyclopropyl | $CH_3$ | $CF_3$ | CH | CH | 113–115 |
| 8 | cyclobutyl | $CH_3$ | $CF_3$ | CH | CH | 84–86 |
| 9 | $CH=C(CH_3)_2$ | $CH_3$ | $CF_3$ | CH | CH | 101–106 |
| 10 | $CH_2C(CH_3)=CH_2$ | $CH_3$ | $CF_3$ | CH | CH | 78–81 |
| 11 | $OCH_3$ | $CH_3$ | $CF_3$ | CH | CH | 111–113 |
| 12 | $OC_2H_5$ | $CH_3$ | $CF_3$ | CH | CH | 100–104 |
| 13 | $OCH(CH_3)_2$ | $CH_3$ | $CF_3$ | CH | CH | 96–98 |
| 14 | $CH(CH_3)_2$ | $CH_2CH_3$ | $CF_3$ | CH | CH | 106–108 |
| 15 | $CH_2CH(CH_3)_2$ | $CH_2CH_3$ | $CF_3$ | CH | CH | 90–91 |
| 16 | $C(CH_3)_3$ | $CH_2CH_3$ | $CF_3$ | CH | CH | 130–133 |
| 17 | cyclopropyl | $CH_2CH_3$ | $CF_3$ | CH | CH | 113–115 |
| 18 | 1-Me-cyclopropyl | $CH_2CH_3$ | $CF_3$ | CH | CH | 90–99 |
| 19 | 2-Me-cyclopropyl | $CH_2CH_3$ | $CF_3$ | CH | CH | 88–93 |
| 20 | $OCH(CH_3)_2$ | $CH_2CH_3$ | $CF_3$ | CH | CH | 79–81 |
| 21 | $CH(CH_3)_2$ | H | $CF_3$ | CH | CH | 80–81 |
| 22 | $C(CH_3)_3$ | H | $CF_3$ | CH | CH | 90–93 |
| 23 | $CH(CH_3)_2$ | Br | $CF_3$ | CH | CH | 108–117 |
| 24 | $C(CH_3)_3$ | Br | $CF_3$ | CH | CH | 153–157 |
| 25 | cyclopropyl | Br | $CF_3$ | CH | CH | 149–150 |
| 26 | 1-Me-cyclopropyl | Br | $CF_3$ | CH | CH | 123–126 |
| 27 | $OCH(CH_3)_2$ | Br | $CF_3$ | CH | CH | 108–110 |

INDEX TABLE A-continued

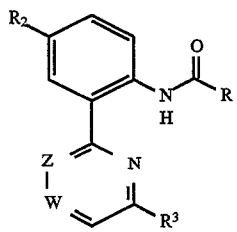

Wherein R is XR[1]

| Cmpd. No. | R | R² | R³ | W | Z | m.p. (°C.)[a] |
|---|---|---|---|---|---|---|
| 28 | CH(CH₃)₂ | CH₃ | Br | CH | CH | 57–60 |
| 29 | CH₂CH(CH₃)₂ | CH₃ | Br | CH | CH | oil |
| 30 | C(CH₃)₃ | CH₃ | Br | CH | CH | 120–126 |
| 31 | 2-Me-cyclopropyl | CH₃ | Br | CH | CH | 77–80 |
| 32 | CH=C(CH₃)₂ | CH₃ | Br | CH | CH | 163–167 |
| 33 | OCH(CH₃)₂ | CH₃ | Br | CH | CH | 73–75 |
| 34 | CH(CH₃)₂ | H | Br | CH | CH | 76–80 |
| 35 | C(CH₃)₃ | H | Br | CH | CH | oil |
| 36 | C(CH₃)₃ | Br | Br | CH | CH | 138–141 |
| 37 | CH(CH₃)₂ | CH₃ | Cl | CH | CH | oil |
| 38 | C(CH₃)₃ | CH₃ | Cl | CH | CH | 109–112 |
| 39 | cyclopropyl | CH₃ | Cl | CH | CH | 95–98 |
| 40 | 1-Me-cyclopropyl | CH₃ | Cl | CH | CH | 104–107 |
| 41 | 2-Me-cyclopropyl | CH₃ | Cl | CH | CH | 80–83 |
| 42 | CH=C(CH₃)₂ | CH₃ | Cl | CH | CH | 174–178 |
| 43 | CH₂CH(CH₃)=CH₂ | CH₃ | Cl | CH | CH | 63–67 |
| 44 | OCH(CH₃)₂ | CH₃ | Cl | CH | CH | 88–91 |
| 45 | C(CH₃)₃ | CH₃ | SCH₃ | CH | CH | 81–86 |
| 46 | CH(CH₃)₂ | CH₃ | SCH₃ | CH | CH | 60–68 |
| 47 | CF₃ | CH₃ | SCH₃ | CH | CH | 108–110 |
| 48 | Ph | CH₃ | CF₃ | CH | CH | 156–157 |
| 49 | C(CH₃)₃ | CH₃ | Cl | N | CH | 80–83 |
| 50 | C(CH₃)₃ | CH₃ | Br | N | CH | 74–76 |
| 51 | C(CH₃)₃ | CH₃ | CF₃ | N | CH | wax |

[a] ¹H NMR data for oils and waxes are given Index Table E.

INDEX TABLE B

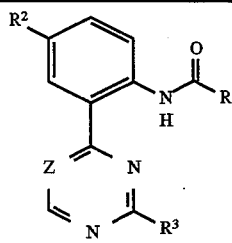

Wherein R is XR[1]

| Cmpd No. | R | R² | R³ | Z | m.p. (°C.) |
|---|---|---|---|---|---|
| 52 | CH(CH₃)₂ | CH₃ | CF₃ | CH | 112–114 |
| 53 | C(CH₃)₃ | CH₃ | CF₃ | CH | 118–120 |
| 54 | CF₃ | CH₃ | CF₃ | CH | 135–138 |
| 55 | CH(CH₃)₂ | CH₃ | SCH₃ | CH | 134–135 |
| 56 | C(CH₃)₃ | CH₃ | SCH₃ | CH | 119–120 |
| 57 | CF₃ | CH₃ | SCH₃ | CH | 181–183 |
| 58 | cyclopropyl | CH₃ | SCH₃ | CH | 120–123 |
| 59 | OCH(CH₃)₂ | CH₃ | SCH₃ | CH | 78–82 |
| 60 | CH(CH₃)₂ | CH₃ | SCHF₂ | CH | 128–130 |
| 61 | C(CH₃)₃ | CH₃ | SCHF₂ | CH | 119–125 |
| 62 | CH(CH₃)₂ | CH₃ | SCF₃ | CH | 114–116 |
| 63 | C(CH₃)₃ | CH₃ | SCF₃ | CH | 124–128 |
| 64 | C(CH₃)₃ | CH₃ | Cl | CH | 111–116 |
| 65 | C(CH₃)₃ | CH₃ | OCH₂CF₃ | CH | 126–128 |
| 66 | Ph | CH₃ | CF₃ | CH | 168–170 |

INDEX TABLE C

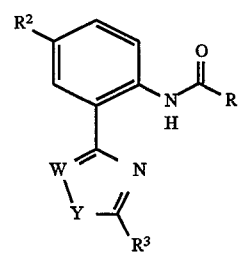

Wherein R is XR[1]

| Cmpd No. | R | R² | R³ | W | Y | m.p. (°C.) |
|---|---|---|---|---|---|---|
| 67 | C(CH₃)₃ | CH₃ | SCH₃ | N | S | 115–117 |
| 68 | C(CH₃)₃ | CH₃ | OCH₂CF₃ | CH | S | 104–107 |
| 69 | C(CH₃)₃ | CH₃ | SCH₃ | CH | S | 95–98 |

Index TABLE D

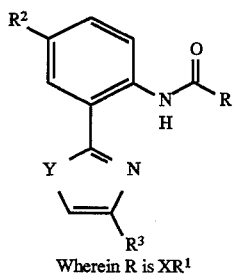

Wherein R is XR[1]

| Cmpd No | R | R² | R³ | Y | m.p. (°C.) |
|---|---|---|---|---|---|
| 70 | C(CH₃)₃ | CH₃ | Br | S | 75–78 |
| 71 | C(CH₃)₃ | CH₃ | CN | S | 204–206 |
| 72 | CH₂CH(CH₃)₂ | CH₃ | CF₃ | S | 96–100 |
| 73 | cyclopropyl | CH₃ | CF₃ | S | 155–156 |
| 74 | CH₃ | CH₃ | CF₃ | S | 130–133 |

Index TABLE E

| Cmpd. No. | ¹H NMR Data[a] |
|---|---|
| 29 | 1.00(d, 6H), 2.25(m, 3H), 2.40(s, 3H), 7.10–8.4(m 6H), 11.5(s, 1H, NH). |
| 35 | 1.38(s, 9H), 7.10–8.4(m, 7H), 11.1(s, 1H, NH). |
| 37 | 1.3(d, 6H), 2.40(s, 3H), 2.60(m, 1H), 7.10–8.4(m, 6H), 11.5(s, 1H, NH). |
| 51 | 1.25(s, 9H), 2.40(s, 3H), 7.33–9.18(m, 5H), 10.3(s, 1H, NH). |

[a] ¹H NMR data are in ppm downfield from tetramethylsilane. Couplings are designated by s-singlet, d-doublet, m-multiplet. Samples dissolved in CDCl₃ unless otherwise indicated.

TEST A

Seeds of barnyardgrass (*Echinochloa crus-galli*), cocklebur (*Xanthium pensylvanicum*), crabgrass (*Digitaria spp.*), downy brome (*Bromus tectorum*), giant foxtail (*Setaria faberii*), morningglory (*Ipomoea spp.*), sorghum (*Sorghum bicolor*), velvetleaf (*Abutilon theophrasti*), and wild oat (*Avena fatua*) were planted into a sandy loam soil and treated preemergence or by soil drench with test chemicals formulated in a non-phytotoxic solvent mixture which includes a surfactant. At the same time, these crop and weed species were also treated postemergence or sprayed to runoff, with test chemicals formulated in the same manner. Plants ranged in height from two to eighteen eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control. A dash (—) response means no test results.

TABLE A

PREEMERGENCE

| | COMPOUND | | | | | COMPOUND 51 | COMPOUND 74 |
|---|---|---|---|---|---|---|---|
| | 49 | 67 | 69 | 72 | 73 | Rate 1000 g/ha | Rate 800 g/ha |
| | Rate 2000 g/ha | | | | | | |
| Barnyardgrass | 3 | 0 | 1 | 1 | 1 | 4 | 0 |
| Cocklebur | 0 | 0 | 0 | 0 | 0 | 0 | 0 |
| Crabgrass | 8 | 0 | 2 | 2 | 2 | 7 | 0 |
| Downy brome | 0 | 0 | 0 | 0 | 0 | 0 | 0 |
| Giant Foxtail | 9 | 0 | 1 | 1 | 3 | 9 | 0 |
| Morningglory | 1 | 0 | 0 | 0 | 1 | 1 | 0 |
| Sorghum | 0 | 0 | 0 | 0 | 0 | 1 | 0 |
| Velvetleaf | 0 | 0 | 0 | 2 | 1 | 0 | 0 |
| Wild Oat | 0 | 0 | 0 | 0 | 0 | 0 | 0 |

POSTEMERGENCE

| | COMPOUND | | | | | COMPOUND 51 | COMPOUND 74 |
|---|---|---|---|---|---|---|---|
| | 49 | 67 | 69 | 72 | 73 | Rate 500 g/ha | Rate 400 g/ha |
| | Rate 1000 g/ha | | | | | | |
| Barnyardgrass | 3 | 0 | 3 | 1 | 2 | 2 | 1 |
| Cocklebur | 2 | 0 | 2 | 2 | 2 | 1 | 0 |
| Crabgrass | 3 | 0 | 2 | 3 | 3 | 2 | 1 |
| Downy brome | 1 | 0 | 1 | 1 | 1 | 0 | 0 |
| Giant Foxtail | 2 | 0 | 1 | 2 | 1 | 1 | 1 |
| Morningglory | 6 | 0 | 3 | 3 | 2 | 3 | 1 |
| Sorghum | 2 | 0 | 2 | 2 | 1 | 0 | 1 |
| Velvetleaf | 2 | 0 | 1 | 1 | 2 | 0 | 1 |
| Wild Oat | 1 | 0 | 0 | 1 | 2 | 0 | 0 |

TEST B

Seeds of barley (*Hordeum vulgare*), barnyardgrass (*Echinochloa crus-galli*), bedstraw (*Galium aparine*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria spp.*), downy brome (*Bromus tectorum*), giant foxtail (*Setaria faberii*), lambsquarter (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which includes a surfactant. At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (—) response means no test result.

TABLE B

| Rate 2000 g/ha | Compound 68 | Compound 71 |
|---|---|---|
| POSTEMERGENCE | | |
| Barley | 4 | 0 |
| Barnyardgrass | 9 | 0 |
| Bedstraw | 7 | 0 |
| Blackgrass | 4 | 0 |
| Chickweed | 6 | 0 |
| Cocklebur | 7 | 0 |
| Corn | 3 | 0 |
| Cotton | 8 | 1 |
| Crabgrass | 8 | 0 |
| Downy brome | 3 | 0 |
| Giant foxtail | 5 | 0 |
| Lambsquarter | 7 | — |
| Morningglory | 8 | 1 |
| Nutsedge | 2 | 0 |
| Rape | 9 | 0 |
| Rice | 2 | 0 |
| Sorghum | 2 | 0 |
| Soybean | 5 | 2 |
| Sugar beet | 9 | 0 |
| Velvetleaf | 3 | 0 |
| Wheat | 4 | 0 |
| Wild buckwheat | 6 | 0 |
| Wild oat | 3 | 0 |

TABLE B-continued

| Rate 2000 g/ha | Compound 68 | Compound 71 |
|---|---|---|
| PREEMERGENCE | | |
| Barley | 5 | 0 |
| Barnyardgrass | 9 | 0 |
| Bedstraw | 6 | 0 |
| Blackgrass | 8 | 0 |
| Chickweed | 8 | 0 |
| Cocklebur | 4 | 0 |
| Corn | 2 | 0 |
| Cotton | 0 | 6 |
| Crabgrass | 10 | 0 |
| Downy brome | 7 | 0 |
| Giant foxtail | 10 | 0 |
| Lambsquarter | 9 | — |
| Morningglory | 31 | |
| Nutsedge | 0 | 0 |
| Rape | 9 | 0 |
| Rice | 1 | 0 |
| Sorghum | 2 | 0 |
| Soybean | 0 | 0 |
| Sugar beet | 9 | 0 |
| Velvetleaf | 6 | 0 |
| Wheat | 3 | 0 |
| Wild buckwheat | 7 | 0 |
| Wild oat | 8 | 0 |

TABLE B

POSTEMERGENCE

| Rate 1000 g/ha | 1 | 2 | 3 | 4 | 5 | 6 | 9 | 11 | 12 | 13 | 14 | 15 | 16 | 17 | 18 | 19 | 20 | 22 | 23 | 24 | 25 | 26 | 27 | 28 | 30 | 31 | 32 | 33 | 34 |
|---|---|---|---|---|---|---|---|---|---|---|---|---|---|---|---|---|---|---|---|---|---|---|---|---|---|---|---|---|---|
| Barley | 8 | 5 | 6 | 3 | 8 | 6 | 3 | 3 | 5 | 4 | 5 | 3 | 2 | 4 | 3 | 3 | 3 | 2 | 8 | 3 | 7 | 5 | 2 | 3 | 3 | 5 | 2 | 3 | 3 |
| Barnyardgrass | 9 | 9 | 9 | 8 | 9 | 8 | 9 | 1 | 8 | 6 | 9 | 8 | 7 | 6 | 8 | 8 | 5 | 3 | 9 | 9 | 9 | 9 | 3 | 9 | 9 | 8 | 3 | 3 | 3 |
| Bedstraw | 9 | 9 | 8 | 8 | 8 | 8 | 8 | 3 | 6 | 8 | 8 | 9 | 7 | 6 | 7 | 7 | 5 | 6 | 8 | 7 | 8 | 8 | 4 | 5 | 6 | 8 | 4 | 7 | 3 |
| Blackgrass | 9 | 9 | 7 | 6 | 9 | 8 | 6 | 2 | 6 | 5 | 9 | 6 | 4 | 8 | 5 | 3 | 2 | 2 | 9 | 5 | 9 | 8 | 4 | 8 | 7 | 7 | 2 | 5 | 2 |
| Chickweed | 9 | 8 | 7 | 9 | 9 | 6 | 7 | 2 | 8 | 7 | 9 | 7 | 6 | 8 | 6 | 4 | 3 | 4 | 9 | 8 | 9 | 9 | 3 | 6 | 7 | 8 | 3 | 6 | 2 |
| Cocklebur | 7 | 7 | 8 | 8 | 9 | 8 | 6 | 6 | 8 | 6 | 7 | 8 | 6 | 8 | 7 | 8 | 5 | 3 | 8 | 8 | 9 | 6 | 5 | 7 | 6 | 5 | 3 | 6 | 3 |
| Corn | 8 | 5 | 6 | 2 | 8 | 6 | 3 | 2 | 3 | 3 | 7 | 3 | 4 | 6 | 4 | 3 | 3 | 2 | 5 | 2 | 6 | 3 | 2 | 5 | 3 | 3 | 2 | 3 | 1 |
| Cotton | 10 | 10 | 10 | 10 | 10 | 10 | 10 | 9 | 9 | 9 | 8 | 8 | 9 | 9 | 9 | 10 | 9 | 4 | 10 | 8 | 10 | 9 | 9 | 9 | 7 | 9 | 9 | 6 | 0 |
| Crabgrass | 9 | 9 | 9 | 8 | 9 | 8 | 7 | 2 | 8 | 6 | 8 | 8 | 3 | 8 | 8 | 9 | 9 | 3 | 9 | 8 | 9 | 9 | 3 | 9 | 6 | 8 | 3 | 4 | 4 |
| Downy brome | 8 | 6 | 3 | 5 | 9 | 6 | 5 | 1 | 5 | 4 | 9 | 5 | 3 | 8 | 2 | 2 | 3 | 2 | 9 | 3 | 8 | 5 | 2 | 4 | 1 | 5 | 1 | 3 | 1 |
| Giant foxtail | 9 | 9 | 9 | 7 | 9 | 8 | 3 | 1 | 6 | 3 | 9 | 7 | 3 | 8 | 7 | 5 | 4 | 2 | 9 | 2 | 9 | 7 | 3 | 8 | 6 | 5 | 2 | 2 | 3 |
| Lambsquarter | 8 | 10 | 9 | 8 | 7 | 8 | 8 | 2 | 9 | 8 | 4 | 9 | 8 | 5 | 6 | 5 | 5 | 7 | 6 | 8 | 7 | 8 | 7 | 5 | 7 | 7 | 6 | 7 | 1 |
| Morningglory | 9 | 9 | 5 | 9 | 8 | 8 | 6 | 3 | 9 | 7 | 6 | 9 | 3 | 6 | 7 | 6 | 7 | 3 | 8 | 8 | 8 | 7 | 5 | 7 | 6 | 6 | 4 | 4 | |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Nutsedge | 7 | 5 | 3 | 1 | 7 | 5 | 1 | 1 | 3 | 1 | 1 | 0 | 1 | 1 | 3 | 2 | 2 | 0 | 2 | 2 | 7 | 3 | 3 | 5 | 1 | 1 | 0 | 0 | 0 |
| Rape | 9 | 9 | 9 | 9 | 9 | 9 | 8 | 5 | 9 | 8 | 9 | 8 | 7 | 8 | 6 | 7 | 8 | 8 | 10 | 8 | 9 | 9 | 6 | 9 | 8 | 8 | 6 | 9 | 8 |
| Rice | 6 | 5 | 5 | 2 | 4 | 3 | 3 | 2 | 3 | 2 | 3 | 3 | 1 | 3 | 4 | 3 | 3 | 1 | 4 | 2 | 5 | 4 | 4 | 3 | 1 | 3 | 3 | 3 | 0 |
| Sorghum | 8 | 5 | 7 | 5 | 7 | 4 | 4 | 1 | 3 | 3 | 3 | 3 | 1 | 3 | 5 | 2 | 2 | 1 | 9 | 3 | 5 | 4 | 3 | 4 | 2 | 6 | 2 | 3 | 1 |
| Soybean | 5 | 7 | 9 | 9 | 2 | 6 | 6 | 1 | 2 | 5 | 2 | 6 | 6 | 5 | 7 | 5 | 6 | 5 | 4 | 5 | 6 | 6 | 4 | 3 | 8 | 7 | 4 | 4 | 2 |
| Sugar beet | 8 | 10 | 9 | 9 | 10 | 10 | 8 | 7 | 10 | 7 | 10 | 9 | 9 | 9 | 10 | 10 | 9 | 8 | 10 | 9 | 9 | 10 | 8 | 6 | 9 | 9 | 8 | 9 | 2 |
| Velvet leaf | 8 | 8 | 9 | 8 | 8 | 8 | 4 | 2 | 6 | 3 | 6 | 8 | 4 | 6 | 9 | 8 | 6 | 2 | 8 | 3 | 9 | 8 | 4 | 4 | 6 | 8 | 5 | 4 | 3 |
| Wheat | 8 | 4 | 4 | 4 | 7 | 4 | 2 | 2 | 2 | 4 | 5 | 4 | 3 | 4 | 2 | 2 | 2 | 2 | 7 | 3 | 7 | 5 | 1 | 4 | 4 | 5 | 1 | 3 | 2 |
| Wild buckwheat | 9 | 9 | 8 | 8 | 9 | 3 | 7 | 3 | 9 | 8 | 9 | 8 | 5 | 9 | 3 | 6 | 4 | 4 | 9 | 7 | 9 | 9 | 3 | 4 | 6 | 9 | 5 | 7 | 2 |
| Wild oat | 9 | 6 | 7 | 6 | 9 | 8 | 6 | 1 | 4 | 5 | 9 | 6 | 3 | 7 | 3 | 3 | 2 | 2 | 9 | 4 | 9 | 8 | 2 | 5 | 6 | 7 | 1 | 2 | 1 |

| Rate 1000 g/ha | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 |
|---|---|---|---|---|---|---|---|---|---|---|---|---|---|---|---|---|---|---|---|---|---|---|---|---|---|
| Barley | 2 | 4 | 5 | 4 | 5 | 3 | 4 | 1 | 3 | 1 | 2 | 9 | 8 | 4 | 3 | 3 | 1 | 4 | 2 | 6 | 3 | 7 | 2 | | |
| Barnyardgrass | 2 | 3 | 8 | 8 | 8 | 4 | 8 | 2 | 7 | 2 | 4 | 9 | 9 | 1 | 9 | 7 | 3 | 9 | 3 | 9 | 7 | 9 | 7 | 9 | 2 |
| Bedstraw | 4 | 5 | 6 | 8 | 6 | 6 | 9 | 2 | 8 | 6 | 4 | 9 | 9 | 7 | 3 | 7 | 3 | 5 | 4 | 3 | 6 | 6 | 4 | 8 | 4 |
| Blackgrass | 1 | 3 | 7 | 5 | 6 | 3 | 6 | 1 | 5 | 3 | 2 | 10 | 9 | 8 | 8 | 4 | 2 | 8 | 2 | 7 | 5 | 6 | 4 | 3 | 2 |
| Chickweed | 3 | 6 | 6 | 7 | 6 | 8 | 8 | 3 | 7 | 5 | 6 | 9 | 9 | 9 | 7 | 6 | 2 | 9 | 4 | 6 | 8 | 8 | 6 | 5 | 3 |
| Cocklebur | 2 | 6 | 4 | 5 | 4 | 6 | 3 | 2 | 5 | 5 | 3 | 8 | 7 | 4 | 6 | 6 | 2 | 7 | 8 | 7 | 6 | 8 | 6 | 3 | 5 |
| Corn | 2 | 2 | 8 | 3 | 8 | 3 | 7 | 2 | 6 | 1 | 3 | 8 | 6 | 1 | 7 | 3 | 1 | 8 | 3 | 4 | 2 | 6 | 2 | 7 | 1 |
| Cotton | 2 | 8 | 8 | 9 | 7 | 8 | 8 | 3 | 9 | 7 | 3 | 5 | 10 | 8 | 9 | 9 | 2 | 9 | 10 | 5 | 9 | 8 | 9 | 9 | 9 |
| Crabgrass | 2 | 3 | 8 | 6 | 7 | 4 | 7 | 1 | 7 | 2 | 3 | 9 | 9 | 6 | 9 | 3 | 2 | 8 | 3 | 9 | 3 | 9 | 7 | 4 | 2 |
| Downy brome | 0 | 2 | 7 | 4 | 6 | 2 | 4 | 0 | 4 | 2 | 1 | 8 | 6 | 3 | 6 | 3 | 1 | 5 | 1 | 3 | 2 | 5 | 2 | 1 | 1 |
| Giant foxtail | 1 | 2 | 8 | 7 | 7 | 3 | 7 | 1 | 6 | 2 | 3 | 9 | 9 | 4 | 9 | 4 | 1 | 8 | 3 | 9 | 4 | 9 | 7 | 6 | 2 |
| Lambsquarter | 4 | 6 | 1 | 6 | 3 | 5 | 7 | 3 | 3 | 6 | 7 | 8 | 9 | 5 | 6 | 6 | 4 | 10 | 8 | 8 | 7 | 8 | 6 | 6 | 5 |
| Morningglory | 6 | 6 | 4 | 4 | 3 | 6 | 6 | 4 | 6 | 4 | 7 | 8 | 9 | 6 | 7 | 8 | 2 | 8 | 9 | 8 | 3 | 9 | 4 | 6 | 6 |
| Nutsedge | 0 | 0 | 7 | 1 | 1 | 2 | 1 | 0 | 0 | 1 | — | — | 5 | — | 0 | 0 | 0 | 3 | 2 | 2 | 0 | 7 | 1 | 4 | 0 |
| Rape | 4 | 8 | 9 | 9 | 8 | 6 | 8 | 1 | 5 | 6 | 4 | 10 | 10 | 10 | 6 | 8 | 2 | 9 | 5 | 6 | 7 | 8 | 9 | 6 | |
| Rice | 1 | 1 | 2 | 3 | 2 | 3 | 1 | 1 | 3 | 3 | 1 | 5 | 7 | 3 | 2 | 3 | 0 | 5 | 2 | 3 | 2 | 6 | 2 | 3 | 1 |
| Sorghum | 1 | 2 | 3 | 2 | 3 | 2 | 3 | 0 | 2 | 2 | 2 | 8 | 8 | 2 | 6 | 2 | 1 | 5 | 3 | 5 | 2 | 7 | 3 | 6 | 1 |
| Soybean | 3 | 3 | 2 | 6 | 3 | 5 | 7 | 3 | 7 | 5 | 4 | 3 | 9 | 2 | 5 | 7 | 1 | 6 | 4 | 6 | 5 | 8 | 6 | 9 | 4 |
| Sugar beet | 7 | 8 | 1 | 10 | 3 | 9 | 9 | 7 | 5 | 9 | 6 | 9 | 9 | 8 | 9 | 9 | 4 | 10 | 9 | 9 | 8 | 9 | 9 | 9 | 8 |
| Velvetleaf | 1 | 2 | 3 | 4 | 2 | 4 | 7 | 3 | 5 | 2 | 6 | 8 | 8 | 2 | 4 | 5 | 1 | 8 | 3 | 7 | 2 | 7 | 2 | 2 | 2 |
| Wheat | 1 | 3 | 6 | 3 | 6 | 3 | 5 | 1 | 3 | 2 | 3 | 9 | 9 | 5 | 3 | 3 | 2 | 4 | 0 | 3 | 2 | 3 | 3 | 6 | 2 |
| Wild buckwheat | 5 | 6 | 7 | 5 | 9 | 2 | 9 | 2 | 2 | 7 | 3 | 8 | 9 | 5 | 3 | 6 | 2 | 10 | 9 | 6 | 5 | 8 | 3 | 6 | 5 |
| Wild oat | 1 | 2 | 7 | 4 | 6 | 2 | 5 | 0 | 2 | 2 | 4 | 10 | 10 | 7 | 8 | 4 | 1 | 7 | 1 | 6 | 3 | 8 | 5 | 8 | 3 |

PRE-EMERGENCE

| Rate 1000 g/ha | 1 | 2 | 3 | 4 | 5 | 6 | 9 | 11 | 12 | 13 | 14 | 15 | 16 | 17 | 18 | 19 | 20 | 22 | 23 | 24 | 25 | 26 | 27 | 28 | 30 | 31 | 32 | 33 | 34 |
|---|---|---|---|---|---|---|---|---|---|---|---|---|---|---|---|---|---|---|---|---|---|---|---|---|---|---|---|---|---|
| Barley | 10 | 5 | 8 | 8 | 7 | 4 | 5 | 0 | 5 | 5 | 9 | 6 | 8 | 6 | 3 | 5 | 2 | 1 | 9 | 7 | 9 | 8 | 0 | 3 | 6 | 3 | 1 | 0 | 0 |
| Barnyardgrass | 10 | 10 | 10 | 10 | 9 | 9 | 9 | 1 | 9 | 9 | 9 | 9 | 9 | 9 | 8 | 9 | 9 | 7 | 6 | 10 | 9 | 9 | 9 | 3 | 7 | 9 | 10 | 4 | 9 | 4 |
| Bedstraw | 7 | 8 | 8 | 9 | 8 | 9 | 5 | 3 | 7 | 6 | 9 | 8 | 9 | 9 | 9 | 10 | 6 | 1 | 7 | 6 | 8 | 6 | 2 | 2 | 7 | 5 | 2 | — | 0 |
| Blackgrass | 9 | 10 | 10 | 10 | 9 | 9 | 9 | 0 | 10 | 9 | 9 | 9 | 9 | 8 | 10 | 9 | 6 | 8 | 10 | 10 | 10 | 10 | 4 | 7 | 8 | 7 | 2 | 7 | 2 |
| Chickweed | 9 | 9 | 9 | 9 | 10 | 9 | 9 | 0 | 10 | 9 | 10 | 9 | 9 | 9 | 9 | 10 | 5 | 5 | 9 | 9 | 10 | 9 | 4 | 8 | 9 | 9 | 7 | — | 7 |
| Cocklebur | 4 | 3 | 4 | 1 | 3 | 2 | 1 | 1 | 1 | 1 | 0 | 0 | 0 | 0 | 2 | 1 | 1 | 0 | 4 | 2 | 3 | 4 | 3 | 0 | 0 | 3 | 0 | 0 | 0 |
| Corn | 9 | 6 | 7 | 2 | 5 | 4 | 5 | 0 | 3 | 4 | 5 | 2 | 3 | 3 | 4 | 2 | 0 | 0 | 8 | 3 | 7 | 4 | 0 | 6 | 6 | 3 | 1 | 2 | 1 |
| Cotton | 7 | 2 | 1 | 9 | 6 | 1 | 2 | 2 | 1 | 2 | 3 | 0 | 3 | 1 | 2 | 2 | 0 | 3 | 2 | 4 | 1 | 0 | 0 | 0 | 2 | 0 | 0 | 0 | 0 |
| Crabgrass | 10 | 10 | 10 | 10 | 10 | 10 | 10 | 1 | 10 | 10 | 10 | 10 | 10 | 10 | 10 | 10 | 9 | 10 | 10 | 10 | 10 | 7 | 10 | 10 | 9 | 7 | 9 | 8 | | |
| Downy brome | 10 | 10 | 10 | 10 | 10 | 10 | 9 | 0 | 10 | 9 | 10 | 9 | 8 | 10 | 8 | 10 | 3 | 3 | 10 | 9 | 10 | 9 | 2 | 4 | 8 | 7 | 2 | — | 0 |
| Giant foxtail | 10 | 10 | 10 | 10 | 10 | 10 | 10 | 2 | 10 | 10 | 10 | 10 | 10 | 10 | 10 | 10 | 9 | 9 | 10 | 10 | 10 | 10 | 5 | 9 | 10 | 10 | 3 | 6 | 9 |
| Lambsquarter | 10 | 10 | 9 | 10 | 9 | 10 | 9 | 0 | 9 | 9 | 10 | 10 | 10 | 9 | 9 | 9 | 7 | 4 | 9 | 8 | 10 | 9 | 4 | 5 | 10 | 9 | 7 | — | 6 |
| Morningglory | 9 | 9 | 9 | 8 | 9 | 9 | 7 | 0 | 7 | 4 | 9 | 7 | 3 | 3 | 3 | 2 | 2 | 2 | 9 | 8 | 9 | 9 | 2 | 2 | 5 | 5 | 5 | 6 | 0 |
| Nutsedge | 5 | 3 | 5 | 0 | — | — | 0 | — | — | 1 | 2 | 1 | 0 | 0 | 0 | 0 | 0 | — | 3 | 0 | 0 | 0 | 0 | 0 | 0 | 0 | 0 | 0 | 0 |
| Rape | 10 | 9 | 10 | 10 | 6 | 8 | 8 | 0 | 8 | 8 | 9 | 9 | 10 | 9 | 8 | 9 | 2 | 4 | 10 | 8 | 10 | 7 | 5 | 9 | 8 | 8 | 3 | 3 | 6 |
| Rice | 2 | 1 | 2 | 1 | 0 | 1 | 1 | 0 | 0 | 1 | 0 | 0 | 1 | 0 | 0 | 0 | 0 | 5 | 3 | 1 | 1 | 4 | 2 | 0 | 2 | 1 | 2 | 2 | 0 |
| Sorghum | 9 | 7 | 8 | 2 | 2 | 3 | 6 | 1 | 3 | 4 | 4 | 3 | 3 | 3 | 2 | 3 | 2 | 0 | 8 | 6 | 6 | 4 | 0 | 3 | 3 | 7 | 1 | 2 | 0 |
| Soybean | 0 | 6 | 4 | 6 | 1 | 2 | 1 | 0 | 1 | 0 | 0 | 0 | 2 | 0 | 1 | 3 | 1 | 0 | 2 | 2 | 1 | 3 | 0 | 1 | 4 | 1 | 2 | 1 | 0 |
| Sugar | 10 | 10 | 9 | 9 | 10 | 9 | 9 | 1 | 9 | 9 | 9 | 9 | 10 | 10 | 10 | 10 | 10 | 9 | 6 | 10 | 9 | 10 | 9 | 5 | 4 | 9 | 9 | 8 | — | 3 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| beet | | | | | | | | | | | | | | | | | | | | | | | | | | | | | | |
| Velvet leaf | 10 | 9 | 10 | 10 | 10 | 7 | 7 | 0 | 9 | 6 | 10 | 10 | 7 | 7 | 7 | 7 | 7 | 5 | 10 | 6 | 10 | 6 | 3 | 8 | 9 | 7 | 3 | 9 | 0 |
| Wheat | 9 | 6 | 9 | 5 | 8 | 6 | 3 | 0 | 3 | 6 | 9 | 6 | 8 | 6 | 1 | 5 | 1 | 2 | 9 | 3 | 9 | 6 | 0 | 5 | 8 | 3 | 1 | 1 | 0 |
| Wild buckwheat | 9 | 6 | 8 | 10 | 10 | 2 | 7 | 2 | 8 | 7 | 9 | 7 | 5 | 9 | 3 | 3 | 2 | 1 | 9 | 5 | 7 | 7 | 1 | 9 | 6 | 4 | 1 | — | 2 |
| Wild oat | 10 | 10 | 10 | 10 | 10 | 9 | 9 | 2 | 10 | 9 | 10 | 9 | 9 | 9 | 8 | 9 | 7 | 3 | 10 | 9 | 10 | 9 | 3 | 8 | 9 | 8 | 1 | 5 | 2 |

| Rate 1000 g/ha | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 |
|---|---|---|---|---|---|---|---|---|---|---|---|---|---|---|---|---|---|---|---|---|---|---|---|---|---|
| Barley | 0 | 4 | 4 | 3 | 2 | 3 | 2 | 0 | 1 | 1 | 0 | 8 | 7 | 2 | 1 | 2 | 0 | 3 | 1 | 7 | 4 | 9 | 3 | 1 | 1 |
| Barnyardgrass | 3 | 8 | 9 | 9 | 7 | 9 | 9 | 2 | 8 | 2 | 8 | 10 | 10 | 3 | 10 | 9 | 7 | 10 | 6 | 10 | 9 | 10 | 9 | 10 | 5 |
| Bedstraw | 0 | 6 | 1 | 5 | 6 | 2 | 3 | 1 | 7 | 1 | 2 | 9 | 10 | 3 | 4 | 4 | 3 | 8 | 0 | 1 | 9 | 8 | 8 | 9 | 5 |
| Blackgrass | 2 | 6 | 7 | 9 | 6 | 5 | 4 | 0 | 4 | 3 | 1 | 10 | 10 | 9 | 10 | 9 | 4 | 10 | 3 | 9 | 9 | 10 | 9 | 10 | 3 |
| Chickweed | 3 | 9 | 9 | 10 | 10 | 9 | 10 | 5 | 6 | 4 | 1 | 10 | 9 | 9 | 10 | 9 | 7 | 10 | 6 | 9 | 9 | 9 | 8 | 9 | 8 |
| Cocklebur | 0 | 0 | 0 | 1 | 0 | 1 | 0 | 0 | 0 | 0 | 0 | 5 | 6 | 0 | 2 | 1 | 0 | 5 | 0 | 1 | 2 | 3 | 1 | 1 | 1 |
| Corn | 0 | 0 | 7 | 4 | 7 | 3 | 2 | 0 | 2 | 3 | 1 | 5 | 8 | 0 | 6 | 3 | 2 | 8 | 1 | 4 | 3 | 5 | 2 | 6 | 1 |
| Cotton | 0 | 1 | 0 | 0 | 1 | 1 | 3 | 2 | 0 | 2 | 1 | 6 | 3 | 6 | 0 | 0 | 1 | 2 | 0 | 0 | 4 | 8 | 2 | 0 | 0 |
| Crabgrass | 9 | 9 | 10 | 10 | 9 | 10 | 10 | 9 | 10 | 10 | 10 | 10 | 10 | 7 | 10 | 10 | 8 | 10 | 7 | 10 | 10 | 10 | 10 | 10 | 9 |
| Downy brome | 1 | 4 | 10 | 10 | 7 | 6 | 4 | 0 | 3 | 2 | 0 | 10 | 10 | 7 | 9 | 5 | 1 | 10 | 1 | 10 | 10 | 10 | 10 | 4 | 3 |
| Giant foxtail | 9 | 7 | 10 | 10 | 9 | 9 | 10 | 7 | 10 | 6 | 10 | 10 | 10 | 7 | 10 | 10 | 9 | 10 | 5 | 10 | 9 | 10 | 10 | 10 | 3 |
| Lambsquarter | 4 | 9 | 1 | 9 | 10 | 9 | 9 | 9 | 5 | 5 | 7 | 10 | 10 | 10 | 10 | 9 | 1 | 10 | 10 | 10 | 9 | 10 | 9 | 9 | 8 |
| Morningglory | 1 | 3 | 1 | 4 | 3 | 6 | 7 | 2 | 2 | 1 | 1 | 10 | 10 | 4 | 8 | 6 | 1 | 10 | 0 | 10 | 6 | 9 | 6 | 8 | 4 |
| Nutsedge | 0 | 0 | 1 | 9 | 2 | 1 | 1 | 0 | 0 | 0 | 0 | — | — | — | 0 | 0 | 0 | 1 | 0 | — | 0 | — | 0 | 1 | 0 |
| Rape | 2 | 5 | 9 | 9 | 7 | 3 | 7 | 1 | 7 | 0 | 1 | 10 | 10 | 10 | 9 | 9 | 2 | 10 | 2 | 9 | 10 | 10 | 10 | 9 | 5 |
| Rice | 0 | 0 | 2 | 0 | 2 | 0 | 1 | 0 | 0 | 1 | 0 | 5 | 5 | 0 | 4 | 1 | 0 | 3 | 2 | 4 | 1 | 2 | 0 | 2 | 0 |
| Sorghum | 0 | 0 | 5 | 1 | 3 | 2 | 3 | 0 | 0 | 1 | 0 | 8 | 9 | 0 | 5 | 4 | 0 | 5 | 0 | 8 | 2 | 8 | 1 | 5 | 1 |
| Soybean | 0 | 1 | 1 | 0 | 1 | 1 | 0 | 0 | 0 | 0 | 4 | 5 | 9 | 1 | 3 | 0 | 1 | 2 | 1 | 4 | 4 | 4 | 2 | 6 | 1 |
| Sugar beet | 3 | 8 | 0 | 10 | 7 | 9 | 8 | 7 | 8 | 8 | 2 | 10 | 10 | 9 | 9 | 7 | 3 | 10 | 4 | 10 | 9 | 10 | 9 | 10 | 9 |
| Velvetleaf | 0 | 3 | 4 | 6 | 1 | 6 | 8 | 2 | 10 | 3 | 1 | 10 | 7 | 1 | 9 | 3 | 1 | 10 | 0 | 8 | 9 | 9 | 6 | 5 | 4 |
| Wheat | 0 | 4 | 6 | 5 | 5 | 5 | 5 | 0 | 2 | 3 | 0 | 9 | 8 | 3 | 8 | 1 | 0 | 4 | 0 | 5 | 6 | 9 | 5 | 2 | 2 |
| Wild buckwheat | 0 | 5 | 3 | 5 | 9 | 2 | 3 | 0 | 0 | 2 | 1 | 10 | 10 | 4 | 9 | 3 | 2 | 6 | 2 | 5 | 8 | 10 | 9 | 7 | 6 |
| Wild oat | 1 | 8 | 9 | 9 | 9 | 9 | 9 | 0 | 8 | 6 | 0 | 10 | 10 | 5 | 10 | 9 | 4 | 10 | 4 | 10 | 9 | 10 | 8 | 9 | 6 |

TABLE B

| | COMPOUND | | | | | | |
|---|---|---|---|---|---|---|---|
| Rate 400 g/ha | 7 | 10 | 21 | 51 | 68 | 70 | 71 |
| POSTEMERGENCE | | | | | | | |
| Barley | 3 | 4 | 1 | 0 | 3 | 0 | — |
| Barnyardgrass | 4 | 9 | 6 | 1 | 3 | 0 | 0 |
| Bedstraw | 6 | 8 | 3 | 3 | 6 | 0 | 0 |
| Blackgrass | 4 | 7 | 3 | 2 | 4 | 1 | 0 |
| Chickweed | 5 | 6 | 4 | 1 | 5 | 0 | 0 |
| Cocklebur | 7 | 4 | 2 | 2 | 5 | 0 | 0 |
| Corn | 2 | 7 | 2 | 2 | 2 | 0 | 0 |
| Cotton | 9 | 10 | 1 | 2 | 7 | 0 | 0 |
| Crabgrass | 7 | 8 | 6 | 1 | 3 | 0 | 0 |
| Downy brome | 2 | 5 | 1 | 0 | 2 | 0 | 0 |
| Cocklebur | 7 | 4 | 2 | 2 | 5 | 0 | 0 |
| Corn | 2 | 7 | 2 | 2 | 2 | 0 | 0 |
| Cotton | 9 | 10 | 1 | 2 | 7 | 0 | 0 |
| Crabgrass | 7 | 8 | 6 | 1 | 3 | 0 | 0 |
| Downy brome | 2 | 5 | 1 | 0 | 2 | 0 | 0 |
| Giant foxtail | 7 | 8 | 2 | 1 | 2 | 0 | 0 |
| Lambsquarter | 9 | 9 | 7 | 2 | 6 | 1 | 0 |
| Morningglory | 8 | 8 | 7 | 2 | 4 | 0 | 1 |
| Nutsedge | 1 | 8 | 0 | 0 | 0 | 0 | 0 |
| Rape | 6 | 8 | 6 | 0 | 8 | 0 | — |
| Rice | 2 | 3 | 1 | 1 | 2 | 0 | 0 |
| Sorghum | 1 | 4 | 1 | 1 | 1 | 0 | 0 |
| Soybean | 4 | 5 | 1 | 3 | 4 | 1 | 2 |
| Sugar beet | 8 | 9 | 7 | 3 | 8 | 3 | — |
| Velvetleaf | 6 | 9 | 6 | 2 | — | 0 | 0 |
| Wheat | 3 | 4 | 2 | 0 | 3 | 0 | — |
| Wild buckwheat | 4 | 5 | 4 | 1 | 5 | 1 | 0 |
| Wild oat | 5 | 8 | 1 | 0 | 2 | 0 | — |

TABLE B-continued

| | COMPOUND | | | | | | |
|---|---|---|---|---|---|---|---|
| Rate 400 g/ha | 7 | 10 | 21 | 51 | 68 | 70 | 71 |
| PREEMERGENCE | | | | | | | |
| Barley | 4 | 5 | 1 | 0 | 2 | 0 | 0 |
| Barnyardgrass | 9 | 10 | 8 | 3 | 4 | 0 | 0 |
| Bedstraw | 7 | 10 | 2 | 0 | 3 | 3 | 0 |
| Blackgrass | 9 | 10 | 8 | 1 | 4 | 0 | 0 |
| Chickweed | 9 | 9 | 9 | 0 | 6 | 0 | 0 |
| Cocklebur | 0 | 1 | 0 | 0 | 0 | 0 | 0 |
| Corn | 2 | 6 | 1 | 1 | 1 | 0 | 0 |
| Cotton | 1 | 1 | 0 | 0 | 0 | 0 | 0 |
| Crabgrass | 9 | 10 | 10 | 9 | 9 | 0 | 0 |
| Downy brome | 8 | 10 | 3 | 0 | 3 | 0 | 0 |
| Giant foxtail | 10 | 10 | 10 | 8 | 8 | 0 | 0 |
| Lambsquarter | 9 | 9 | 9 | 4 | 8 | 0 | 0 |
| Morningglory | 7 | 10 | 4 | 0 | 4 | 0 | 0 |
| Nutsedge | 2 | 10 | 0 | 0 | 0 | 0 | 0 |
| Rape | 6 | 9 | 7 | 0 | 5 | 0 | 0 |
| Rice | 1 | 1 | 1 | 0 | 0 | 0 | 0 |
| Sorghum | 4 | 7 | 3 | 0 | 1 | 0 | 0 |
| Soybean | 0 | 1 | 0 | 0 | 0 | 0 | 0 |
| Sugar beet | 10 | 10 | 10 | 2 | 8 | 0 | 0 |
| Velvetleaf | 7 | 9 | 4 | 0 | 2 | 0 | 0 |
| Wheat | 4 | 4 | 0 | 0 | 0 | 0 | 0 |
| Wild buckwheat | 4 | 8 | 7 | 0 | 1 | 1 | 0 |
| Wild oat | 9 | 9 | 5 | 0 | 6 | 0 | 0 |

TABLE B

POSTEMERGENCE

| Rate 200 g/ha | \ | \ | \ | \ | \ | \ | \ | \ | \ | \ | \ | \ | COMPOUND | \ | \ | \ | \ | \ | \ | \ | \ | \ | \ | \ | \ | \ | \ | \ | \ |
|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 9 | 11 | 12 | 13 | 14 | 15 | 16 | 17 | 18 | 19 | 20 | 22 | 23 | 24 | 25 | 26 | 27 | 28 | 30 | 31 | 32 | 33 | 34 |
| Barley | 7 | 3 | 3 | 2 | 5 | 3 | 3 | 1 | 2 | 3 | 3 | 3 | 2 | 3 | 2 | 3 | 2 | 0 | 6 | 3 | 5 | 3 | 1 | 1 | 3 | 4 | 2 | 1 | 1 |
| Barnyardgrass | 9 | 9 | 9 | 3 | 8 | 4 | 6 | 0 | 3 | 3 | 5 | 3 | 2 | 3 | 3 | 3 | 2 | 0 | 8 | 7 | 9 | 6 | 2 | 6 | 3 | 4 | 2 | 3 | 1 |
| Bedstraw | 7 | 8 | 8 | 4 | 6 | 6 | 7 | 2 | 2 | 6 | 6 | 6 | 7 | 5 | 6 | 7 | 6 | 4 | 7 | 7 | 8 | 7 | 3 | 2 | 5 | 7 | 3 | 4 | 1 |
| Blackgrass | 9 | 4 | 4 | 2 | 6 | 2 | 4 | 0 | 3 | 3 | 6 | 4 | 3 | 5 | 2 | 3 | 2 | 2 | 7 | 4 | 8 | 4 | 2 | 5 | 3 | 5 | 1 | 3 | 1 |
| Chickweed | 9 | 7 | 4 | 7 | 7 | 6 | 4 | 2 | 4 | 5 | 7 | 5 | 5 | 6 | 3 | 3 | 3 | 3 | 8 | 6 | 8 | 7 | 2 | 3 | 3 | 7 | 2 | 3 | 1 |
| Cocklebur | 4 | 6 | 6 | 5 | 7 | 6 | 5 | 2 | 3 | 4 | 4 | 6 | 6 | 6 | 6 | 5 | 5 | 2 | 5 | 7 | 8 | 6 | 4 | 5 | 6 | 5 | 3 | 4 | 1 |
| Corn | 6 | 4 | 4 | 2 | 6 | 4 | 2 | 0 | 3 | 2 | 3 | 2 | 2 | 1 | 2 | 2 | 1 | 2 | 3 | 2 | 4 | 3 | 2 | 3 | 2 | 2 | 2 | 3 | 0 |
| Cotton | 9 | 9 | 9 | 9 | 9 | 9 | 9 | 4 | 6 | 8 | 6 | 5 | 8 | 7 | 9 | 9 | 9 | 1 | 9 | 9 | 10 | 9 | 9 | 4 | 6 | 8 | 9 | 7 | 0 |
| Crabgrass | 8 | 9 | 9 | 6 | 6 | 4 | 4 | 1 | 5 | 3 | 7 | 3 | 2 | 5 | 5 | 8 | 3 | — | 9 | 6 | 9 | 6 | 3 | 6 | 3 | 4 | 3 | 3 | 1 |
| Downy brome | 7 | 3 | 2 | 2 | 3 | 1 | 3 | 1 | 2 | 3 | 6 | 3 | 2 | 4 | 1 | 2 | 2 | 0 | 6 | 3 | 7 | 3 | 0 | 1 | 1 | 5 | 1 | 2 | 0 |
| Giant foxtail | 8 | 7 | 8 | 3 | 6 | 3 | 2 | 1 | 3 | 2 | 6 | 2 | 1 | 3 | 3 | 5 | 1 | 0 | 7 | 3 | 9 | 3 | 2 | 4 | 4 | 3 | 1 | 1 | 0 |
| Lambsquarter | 6 | 10 | 9 | 8 | 2 | 7 | 5 | 0 | 8 | 5 | 3 | 7 | 7 | 4 | 4 | 3 | 3 | 5 | 4 | 8 | 6 | 7 | 4 | 1 | 6 | 6 | 3 | 4 | 0 |
| Morningglory | 7 | 8 | 3 | 8 | 7 | 8 | — | 1 | 5 | 2 | 6 | 8 | 4 | 4 | 6 | 6 | 7 | 2 | 8 | 4 | 8 | 8 | 3 | 3 | 7 | 5 | 5 | 4 | 2 |
| Nutsedge | 4 | 1 | 1 | 0 | 3 | 0 | 0 | 0 | 2 | 0 | 0 | 0 | 0 | 0 | 0 | 0 | 0 | 0 | 2 | 0 | 5 | 0 | 0 | 2 | 0 | 0 | 0 | 0 | 0 |
| Rape | 9 | 9 | 9 | 9 | 6 | 6 | 8 | 2 | 5 | 4 | 7 | 8 | 7 | 8 | 3 | 7 | 2 | 4 | 9 | 8 | 8 | 9 | 4 | 8 | 7 | 7 | 4 | 5 | 4 |
| Rice | 3 | 3 | 3 | 1 | 2 | 3 | 2 | 0 | 2 | 2 | 1 | 3 | 1 | 1 | 1 | 0 | 1 | 0 | 3 | 2 | 3 | 4 | 3 | 1 | 1 | 2 | 2 | 3 | 0 |
| Sorghum | 6 | 5 | 3 | 1 | 2 | 1 | 2 | 0 | 1 | 2 | 2 | 2 | 1 | 1 | 3 | 1 | 1 | 0 | 6 | 1 | 5 | 3 | 3 | 1 | — | 4 | 1 | 3 | 0 |
| Soybean | 3 | 7 | 8 | 7 | 3 | 3 | 6 | 1 | 2 | 4 | 2 | 5 | 5 | 2 | 5 | 3 | 4 | 4 | 3 | 6 | 5 | 5 | 4 | 2 | 7 | 3 | 5 | 5 | 0 |
| Sugar beet | 8 | 10 | 9 | 8 | 10 | 10 | 8 | 3 | 10 | 6 | 7 | 9 | 9 | 8 | 8 | 8 | 8 | 7 | 9 | 8 | 9 | 9 | 7 | 2 | 8 | 5 | 5 | 4 | 0 |
| Velvetleaf | 6 | 8 | 3 | 6 | 7 | 3 | 3 | 2 | 3 | 2 | 4 | 5 | 2 | 2 | 7 | 4 | 3 | 2 | 8 | — | 8 | 7 | 3 | 2 | 4 | 4 | 5 | 3 | 3 |
| Wheat | 7 | 2 | 2 | 3 | 5 | 2 | 2 | 1 | 1 | 2 | 3 | 3 | 2 | 3 | 1 | 2 | 2 | 1 | 5 | 3 | 6 | 2 | 0 | 1 | 2 | 2 | 0 | 2 | 1 |
| Wild buckwheat | 9 | 7 | 5 | 7 | 6 | 1 | 8 | 3 | 2 | 7 | 7 | 6 | 4 | 8 | 3 | 4 | 3 | 3 | 9 | 5 | 8 | 7 | 3 | 2 | 6 | 8 | 4 | 5 | 2 |
| Wild oat | 8 | 2 | 3 | 3 | 4 | 2 | 5 | 1 | 3 | 2 | 5 | 3 | 3 | 4 | 1 | 2 | 1 | 1 | 7 | 4 | 6 | 3 | 1 | 3 | 4 | 3 | 0 | 1 | 1 |

| Rate 200 g/ha | \ | \ | \ | \ | \ | \ | \ | \ | COMPOUND | \ | \ | \ | \ | \ | \ | \ | \ | \ | \ | \ | \ | \ | \ | \ |
|---|---|---|---|---|---|---|---|---|---|---|---|---|---|---|---|---|---|---|---|---|---|---|---|---|
| | 35 | 36 | 37 | 38 | 39 | 40 | 41 | 42 | 43 | 44 | 45 | 52 | 53 | 54 | 55 | 56 | 57 | 58 | 59 | 60 | 61 | 62 | 63 | 64 | 65 |
| Barley | 1 | 3 | 1 | 3 | 2 | 2 | 1 | 1 | 2 | 2 | 0 | 6 | 6 | 2 | 1 | 3 | 0 | 2 | 0 | 2 | 2 | 3 | 3 | 3 | 1 |
| Barnyardgrass | 0 | 2 | 4 | 2 | 4 | 2 | 5 | 2 | 3 | 2 | 1 | 7 | 9 | 1 | 6 | 3 | 2 | 7 | 3 | 9 | 3 | 8 | 3 | 2 | 2 |
| Bedstraw | 1 | 4 | 3 | 6 | 5 | 6 | 6 | 3 | 6 | 5 | 4 | 7 | 9 | 3 | 2 | 7 | 2 | 3 | 3 | 2 | 7 | 3 | 4 | 6 | 3 |
| Blackgrass | 0 | 2 | 2 | 2 | 3 | 2 | 3 | 1 | 2 | 3 | 1 | 7 | 9 | 2 | 6 | 2 | 1 | 7 | 1 | 6 | 2 | 2 | 2 | 1 | 2 |
| Chickweed | 2 | 3 | 3 | 5 | 5 | 5 | 6 | 2 | 4 | 3 | 2 | 9 | 9 | 4 | 5 | 3 | 2 | 6 | 3 | 3 | 7 | 5 | 5 | 3 | 3 |
| Cocklebur | 2 | 4 | 2 | 5 | 2 | 3 | 3 | 1 | 2 | 3 | 2 | 6 | 6 | 2 | 5 | 3 | 2 | 4 | 6 | 7 | 6 | 7 | 4 | 4 | 3 |
| Corn | 1 | 2 | 6 | 2 | 4 | 1 | 3 | 1 | 2 | 1 | 1 | 7 | 5 | 1 | 3 | 2 | 1 | 4 | 3 | 3 | 1 | 4 | 2 | 1 | 1 |
| Cotton | 1 | 9 | 3 | 5 | 7 | 8 | 7 | 3 | 4 | 7 | 2 | 2 | 4 | 6 | 4 | 5 | 1 | 9 | 4 | 6 | 9 | 4 | 10 | 2 | 9 |
| Crabgrass | 1 | 2 | 6 | 1 | 2 | 2 | 3 | 1 | 2 | 2 | 2 | 5 | 7 | 2 | 5 | 1 | 2 | 5 | 3 | 6 | 2 | 9 | 3 | 4 | 2 |
| Downy brome | 0 | 1 | 1 | 2 | 4 | 2 | 2 | 0 | 0 | 1 | 0 | 3 | 3 | 1 | 2 | 1 | 1 | 2 | 2 | 2 | 2 | 2 | 0 | 1 | 0 |
| Giant foxtail | 1 | 1 | 4 | 2 | 2 | 2 | 2 | 1 | 2 | 2 | 1 | 8 | 9 | 2 | 5 | 1 | 1 | 5 | 2 | 6 | 3 | 9 | 2 | 3 | 2 |
| Lambsquarter | 2 | 4 | 1 | 4 | 0 | 4 | 5 | 2 | 1 | 5 | 4 | 4 | 7 | 1 | 4 | 6 | 3 | 8 | 3 | 6 | 6 | 8 | 6 | 5 | 5 |
| Morningglory | 2 | 2 | 2 | 2 | 2 | 2 | 6 | 2 | 2 | 4 | 1 | 7 | 8 | 3 | 5 | 5 | 1 | 7 | 6 | 7 | — | 8 | — | 2 | 3 |
| Nutsedge | 0 | 0 | 2 | 0 | 0 | 0 | 0 | 0 | 0 | 0 | — | 3 | 1 | 0 | 0 | 0 | 0 | 0 | 0 | 1 | 0 | 2 | 0 | 0 | 0 |
| Rape | 4 | 6 | 7 | 5 | 4 | 3 | 1 | 2 | 6 | 1 | 7 | 8 | 3 | 4 | 5 | 2 | 3 | 6 | 3 | 7 | 4 | 7 | 7 | 6 | |
| Rice | 1 | 2 | 0 | 2 | 0 | 2 | 2 | 0 | 0 | 2 | 0 | 1 | 1 | 0 | 1 | 2 | 0 | 2 | 2 | 1 | 1 | 2 | 1 | 2 | 1 |
| Sorghum | 0 | 1 | 1 | 1 | 0 | 2 | 1 | 0 | 1 | 1 | 1 | 3 | 3 | 0 | 1 | 1 | 0 | 3 | 3 | 3 | 1 | 3 | 1 | 1 | 1 |
| Soybean | 2 | 2 | 0 | 6 | 2 | 4 | 7 | 3 | 5 | 3 | 2 | 1 | 9 | 1 | 3 | 5 | 2 | 6 | 3 | 5 | 5 | 8 | 4 | 5 | 3 |
| Sugar beet | 5 | 8 | 1 | 9 | 0 | 9 | 6 | 2 | 2 | 6 | 2 | 6 | 8 | 3 | 7 | 3 | 4 | 9 | 2 | 9 | 9 | 9 | 8 | 7 | 8 |
| Velvet- | 1 | 1 | 2 | 3 | 1 | 2 | 2 | 2 | 3 | 1 | 2 | 8 | 7 | 3 | 3 | 3 | 0 | 4 | 3 | 7 | 1 | 2 | 2 | 1 | 1 |

TABLE B-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| leaf | | | | | | | | | | | | | | | | | | | | | | | | | | | |
| Wheat | 0 | 2 | 2 | 3 | 3 | 3 | 2 | 1 | 2 | 2 | 1 | 6 | 5 | 1 | 1 | 2 | 1 | 1 | 0 | 2 | 2 | 2 | 1 | 2 | | | |
| Wild buckwheat | 2 | 1 | 3 | 3 | 7 | 2 | 7 | 1 | 0 | 4 | 2 | 6 | 6 | 3 | 1 | 3 | 2 | 8 | 6 | 6 | 5 | 8 | 1 | 6 | 3 | | |
| Wild oat | 0 | 1 | 0 | 1 | 2 | 2 | 1 | 0 | 1 | 2 | 0 | 10 | 6 | 6 | 3 | 1 | 1 | 2 | 0 | 3 | 3 | 7 | 3 | 2 | 1 | | |

PREEMERGENCE

Rate 200 COMPOUND

| g/ha | 1 | 2 | 3 | 4 | 5 | 6 | 9 | 11 | 12 | 13 | 14 | 15 | 16 | 17 | 18 | 19 | 20 | 22 | 23 | 24 | 25 | 26 | 27 | 28 | 30 | 31 | 32 | 33 | 34 |
|---|---|---|---|---|---|---|---|---|---|---|---|---|---|---|---|---|---|---|---|---|---|---|---|---|---|---|---|---|---|
| Barley | 7 | 3 | 3 | 2 | 5 | 3 | 3 | 1 | 2 | 3 | 3 | 3 | 2 | 3 | 2 | 3 | 2 | 0 | 6 | 3 | 5 | 3 | 1 | 1 | 3 | 4 | 2 | 1 | 1 |
| Barnyardgrass | 9 | 9 | 9 | 3 | 8 | 4 | 6 | 0 | 3 | 3 | 5 | 3 | 2 | 3 | 3 | 3 | 2 | 0 | 8 | 7 | 9 | 6 | 2 | 6 | 3 | 4 | 2 | 3 | 1 |
| Bedstraw | 7 | 8 | 8 | 4 | 6 | 6 | 7 | 2 | 2 | 6 | 6 | 6 | 7 | 5 | 6 | 7 | 6 | 4 | 7 | 7 | 8 | 7 | 3 | 2 | 5 | 7 | 3 | 4 | 1 |
| Blackgrass | 9 | 4 | 4 | 2 | 6 | 2 | 4 | 0 | 3 | 3 | 6 | 4 | 3 | 5 | 2 | 3 | 2 | 2 | 7 | 4 | 8 | 4 | 2 | 5 | 3 | 5 | 1 | 3 | 1 |
| Chickweed | 9 | 7 | 4 | 7 | 7 | 6 | 4 | 2 | 4 | 5 | 7 | 5 | 5 | 6 | 3 | 3 | 3 | 3 | 8 | 6 | 8 | 7 | 2 | 3 | 3 | 7 | 2 | 3 | 1 |
| Cocklebur | 4 | 6 | 6 | 5 | 7 | 6 | 5 | 2 | 3 | 4 | 4 | 6 | 6 | 6 | 6 | 5 | 5 | 2 | 5 | 7 | 8 | 6 | 4 | 5 | 6 | 5 | 3 | 4 | 1 |
| Corn | 6 | 4 | 4 | 2 | 6 | 4 | 2 | 0 | 3 | 2 | 3 | 2 | 2 | 1 | 2 | 2 | 1 | 2 | 3 | 2 | 4 | 3 | 2 | 3 | 2 | 2 | 2 | 3 | 0 |
| Cotton | 9 | 9 | 9 | 9 | 9 | 9 | 9 | 4 | 6 | 8 | 6 | 5 | 8 | 7 | 9 | 9 | 9 | 1 | 9 | 9 | 10 | 9 | 9 | 4 | 6 | 8 | 9 | 7 | 0 |
| Crabgrass | 8 | 9 | 9 | 6 | 6 | 4 | 4 | 1 | 5 | 3 | 7 | 3 | 2 | 5 | 5 | 8 | 3 | — | 9 | 6 | 9 | 6 | 3 | 6 | 3 | 4 | 3 | 3 | 1 |
| Downy brome | 7 | 3 | 2 | 2 | 3 | 1 | 3 | 1 | 2 | 3 | 6 | 3 | 2 | 4 | 1 | 2 | 2 | 0 | 6 | 3 | 7 | 3 | 0 | 1 | 1 | 5 | 1 | 2 | 0 |
| Giant foxtail | 8 | 7 | 8 | 3 | 6 | 3 | 2 | 1 | 3 | 2 | 6 | 2 | 1 | 3 | 3 | 5 | 1 | 0 | 7 | 3 | 9 | 3 | 2 | 4 | 4 | 3 | 1 | 1 | 0 |
| Lambsquarter | 6 | 10 | 9 | 8 | 2 | 7 | 5 | 0 | 8 | 5 | 3 | 7 | 7 | 4 | 4 | 3 | 3 | 5 | 4 | 8 | 6 | 7 | 4 | 1 | 6 | 6 | 3 | 4 | 0 |
| Morningglory | 7 | 8 | 3 | 8 | 7 | 8 | — | 1 | 5 | 2 | 6 | 8 | 4 | 4 | 6 | 6 | 7 | 2 | 8 | 4 | 8 | 8 | 3 | 3 | 7 | 5 | 5 | 4 | 2 |
| Nutsedge | 4 | 1 | 1 | 0 | 3 | 0 | 0 | 0 | 2 | 0 | 0 | 0 | 0 | 0 | 0 | 0 | 0 | 0 | 2 | 0 | 5 | 0 | 0 | 2 | 0 | 0 | 0 | 0 | 0 |
| Rape | 9 | 9 | 9 | 9 | 6 | 6 | 8 | 2 | 5 | 4 | 7 | 8 | 7 | 8 | 3 | 7 | 2 | 4 | 9 | 8 | 8 | 9 | 4 | 8 | 7 | 7 | 4 | 5 | 4 |
| Rice | 3 | 3 | 3 | 1 | 2 | 3 | 2 | 0 | 2 | 2 | 1 | 3 | 1 | 1 | 1 | 0 | 1 | 0 | 3 | 2 | 3 | 4 | 3 | 1 | 1 | 2 | 2 | 3 | 0 |
| Sorghum | 6 | 5 | 3 | 1 | 2 | 1 | 2 | 0 | 1 | 2 | 2 | 2 | 1 | 1 | 3 | 1 | 1 | 0 | 6 | 1 | 5 | 3 | 3 | 1 | — | 4 | 1 | 3 | 0 |
| Soybean | 3 | 7 | 8 | 7 | 3 | 3 | 6 | 1 | 2 | 4 | 2 | 5 | 5 | 2 | 5 | 3 | 4 | 4 | 3 | 6 | 5 | 5 | 4 | 2 | 7 | 3 | 5 | 5 | 0 |
| Sugar beet | 8 | 10 | 9 | 8 | 10 | 10 | 8 | 3 | 10 | 6 | 7 | 9 | 9 | 8 | 8 | 8 | 8 | 7 | 9 | 8 | 9 | 9 | 7 | 2 | 8 | 5 | 5 | 4 | 0 |
| Velvetleaf | 6 | 8 | 3 | 6 | 7 | 3 | 3 | 2 | 3 | 2 | 4 | 5 | 2 | 2 | 7 | 4 | 3 | 2 | 8 | — | 8 | 7 | 3 | 2 | 4 | 4 | 5 | 3 | 3 |
| Wheat | 7 | 2 | 2 | 3 | 5 | 2 | 2 | 1 | 1 | 2 | 3 | 3 | 2 | 3 | 1 | 2 | 2 | 1 | 5 | 3 | 6 | 2 | 0 | 1 | 2 | 2 | 0 | 2 | 1 |
| Wild buckwheat | 9 | 7 | 5 | 9 | 6 | 1 | 8 | 3 | 2 | 7 | 7 | 6 | 4 | 8 | 3 | 4 | 3 | 3 | 9 | 5 | 8 | 7 | 3 | 2 | 6 | 8 | 4 | 5 | 2 |
| Wild oat | 8 | 2 | 3 | 3 | 4 | 2 | 5 | 1 | 3 | 2 | 5 | 3 | 3 | 4 | 1 | 2 | 1 | 1 | 7 | 4 | 6 | 3 | 1 | 3 | 4 | 3 | 0 | 1 | 1 |

| Rate 200 | | | | | | | | | | | COMPOUND | | | | | | | | | | | | | | |
|---|---|---|---|---|---|---|---|---|---|---|---|---|---|---|---|---|---|---|---|---|---|---|---|---|---|
| g/ha | 35 | 36 | 37 | 38 | 39 | 40 | 41 | 42 | 43 | 44 | 45 | 52 | 53 | 54 | 55 | 56 | 57 | 58 | 59 | 60 | 61 | 62 | 63 | 64 | 65 |
| Barley | 0 | 2 | 1 | 1 | 0 | 0 | 0 | 0 | 2 | 0 | 0 | 5 | 3 | 0 | 0 | 0 | 0 | 1 | 0 | 2 | 1 | 4 | 0 | 2 | 0 |
| Barnyardgrass | 0 | 2 | 5 | 3 | 4 | 2 | 4 | 0 | 2 | 0 | 1 | 9 | 10 | 1 | 10 | 3 | 3 | 9 | 1 | 9 | 3 | 9 | 3 | 8 | 2 |
| Bedstraw | 0 | 1 | 1 | 0 | 1 | 0 | 2 | 0 | 0 | 0 | 1 | 3 | 10 | 1 | 1 | 0 | 1 | 4 | 0 | 0 | 7 | — | 3 | 2 | 3 |
| Blackgrass | 0 | 3 | 4 | 1 | 3 | 0 | 0 | 0 | 0 | 0 | 0 | 10 | 10 | 2 | 9 | 2 | 3 | 9 | 0 | 9 | 6 | 9 | 5 | 6 | 1 |
| Chickweed | 0 | 5 | 3 | 7 | 3 | 4 | 6 | 0 | 0 | 1 | 1 | 9 | 9 | 6 | 9 | 4 | 3 | 10 | 1 | 9 | 7 | 9 | 7 | 8 | 5 |
| Cocklebur | 0 | 0 | 0 | 0 | 0 | 0 | 0 | 0 | 0 | 0 | 0 | 2 | 0 | 2 | 0 | 0 | 2 | 0 | 1 | 0 | 1 | 0 | 0 | 0 | 0 |
| Corn | 0 | 0 | 4 | 0 | 2 | 0 | 1 | 0 | 1 | 0 | 0 | 4 | 5 | 0 | 6 | 0 | 0 | 3 | 0 | 2 | 1 | 1 | 2 | 0 | |
| Cotton | 0 | 0 | 0 | 0 | 0 | 0 | 0 | 0 | 0 | 0 | 0 | 1 | 1 | 0 | 0 | 0 | 0 | 0 | 0 | 2 | 5 | 0 | 0 | 0 | |
| Crabgrass | 0 | 5 | 10 | 9 | 2 | 5 | 9 | 3 | 8 | 1 | 6 | 10 | 10 | 1 | 9 | 6 | 7 | 10 | 3 | 10 | 9 | 10 | 9 | 9 | 5 |
| Downy brome | 0 | 2 | 4 | 1 | 2 | 0 | 2 | 0 | 0 | 0 | 0 | 9 | 8 | 1 | 3 | 1 | 1 | 4 | 1 | 7 | 4 | 7 | 4 | 3 | 1 |
| Giant foxtail | 0 | 2 | 8 | 8 | 3 | 6 | 9 | 2 | 8 | 2 | 3 | 10 | 10 | 2 | 9 | 4 | 7 | 9 | 2 | 10 | 9 | 10 | 9 | 10 | 1 |
| Lambsquarter | 0 | 5 | 1 | 7 | 1 | 3 | 5 | 0 | 0 | 0 | 1 | 10 | 10 | 8 | 10 | 4 | 2 | 10 | 2 | 10 | 9 | 10 | 8 | 9 | 6 |
| Morningglory | 0 | 1 | 0 | 1 | 0 | 2 | 4 | 0 | 2 | 1 | 1 | 8 | 9 | 1 | 6 | 2 | 0 | 6 | 0 | 8 | 4 | 8 | 2 | 1 | 3 |
| Nutsedge | 0 | 0 | 0 | 0 | 0 | 0 | 0 | 0 | 0 | 0 | 0 | — | — | — | 0 | 0 | 0 | 0 | 0 | — | 0 | — | 0 | 0 | 0 |

TABLE B-continued

| | | | | | | | | | | | | | | | | | | | | | | | | | |
|---|---|---|---|---|---|---|---|---|---|---|---|---|---|---|---|---|---|---|---|---|---|---|---|---|---|
| Rape | 0 | 0 | 3 | 2 | 1 | 0 | 0 | 0 | 1 | 0 | 1 | 10 | 10 | 1 | 8 | 5 | 1 | 7 | 0 | 6 | 7 | 8 | 7 | 6 | 3 |
| Rice | 0 | 0 | 0 | 0 | 0 | 0 | 0 | 0 | 0 | 0 | 0 | 1 | 2 | 0 | 1 | 0 | 0 | 0 | 1 | 1 | 0 | 1 | 0 | 1 | 0 |
| Sorghum | 0 | 0 | 0 | 0 | 0 | 0 | 0 | 1 | 0 | 0 | 0 | 5 | 6 | 0 | 3 | 1 | 0 | 2 | 0 | 3 | 1 | 4 | 1 | 1 | 0 |
| Soybean | 0 | 0 | 0 | 0 | 0 | 0 | 0 | 0 | 0 | 0 | 1 | 0 | 5 | 1 | 0 | 0 | 0 | 0 | 1 | 9 | 1 | 2 | 1 | 0 | 0 |
| Sugar beet | 0 | 6 | 1 | 2 | 3 | 2 | 1 | 2 | 2 | 0 | 2 | 9 | 10 | 2 | 10 | 2 | 2 | 10 | 0 | 9 | 9 | 10 | 7 | 9 | 7 |
| Velvetleaf | 0 | 0 | 0 | 2 | 0 | 1 | 5 | 0 | 4 | 0 | 0 | 10 | 6 | 0 | 3 | 1 | 0 | 7 | 0 | 4 | 4 | 4 | 5 | 1 | 2 |
| Wheat | 0 | 1 | 2 | 1 | 1 | 1 | 2 | 0 | 1 | 0 | 0 | 5 | 5 | 1 | 0 | 0 | 0 | 2 | 0 | 1 | 1 | 3 | 1 | 0 | 0 |
| Wild buckwheat | 0 | 1 | 1 | 1 | 3 | 1 | 1 | 0 | 0 | 1 | 1 | 8 | 8 | 1 | 3 | 0 | 1 | 4 | 0 | 1 | 4 | 3 | 4 | 1 | 2 |
| Wild oat | 0 | 3 | 5 | 4 | 4 | 3 | 3 | 0 | 3 | 0 | 0 | 10 | 10 | 1 | 7 | 3 | 1 | 9 | 0 | 9 | 4 | 10 | 5 | 3 | 2 |

TABLE B

POSTEMERGENCE

| | COMPOUND | | | | |
|---|---|---|---|---|---|
| Rate 100 g/ha | 7 | 10 | 21 | 51 | 70 |
| Barley | 2 | 3 | 1 | 0 | 0 |
| Barnyardgrass | 2 | 8 | 2 | 0 | 0 |
| Bedstraw | 5 | 8 | 2 | 0 | 0 |
| Blackgrass | 2 | 3 | 1 | 0 | 0 |
| Chickweed | 3 | 4 | 2 | 0 | 0 |
| Cocklebur | 3 | 2 | 0 | 1 | 0 |
| Corn | 1 | 3 | 1 | 0 | 0 |
| Cotton | 8 | 10 | 0 | 0 | 0 |
| Crabgrass | 3 | 8 | 2 | 1 | 0 |
| Downy brome | 2 | 2 | 1 | 0 | 0 |
| Giant foxtail | 2 | 6 | 1 | 0 | 0 |
| Lambsquarter | 7 | 9 | 5 | 2 | 1 |
| Morningglory | 8 | 6 | 4 | 2 | 0 |
| Nutsedge | 0 | 1 | 0 | 0 | 0 |
| Rape | 6 | 6 | 5 | 0 | 0 |
| Rice | 1 | 1 | 0 | 0 | 0 |
| Sorghum | 1 | 3 | 1 | 0 | 0 |
| Soybean | 2 | 5 | 1 | 1 | 1 |
| Sugar beet | 7 | 9 | 5 | 0 | 1 |
| Velvetleaf | 3 | 8 | 2 | 0 | 0 |
| Wheat | 2 | 1 | 1 | 0 | 0 |
| Wild buckwheat | 3 | 2 | 2 | 0 | 0 |
| Wild oat | 1 | 3 | 0 | 0 | 0 |

PREEMERGENCE

| | COMPOUND | | | | |
|---|---|---|---|---|---|
| Rate 100 g/ha | 7 | 10 | 21 | 51 | 70 |
| Barley | 2 | 2 | 0 | 0 | 0 |
| Barnyardgrass | 9 | 10 | 4 | 0 | 0 |
| Bedstraw | 2 | 9 | 1 | 0 | — |
| Blackgrass | 8 | 9 | 3 | 0 | 0 |
| Chickweed | 9 | 9 | 8 | 0 | 0 |
| Cocklebur | 0 | 0 | 0 | 0 | 0 |
| Corn | 1 | 3 | 0 | 0 | 0 |
| Cotton | 1 | 0 | 0 | 0 | 0 |
| Crabgrass | 8 | 9 | 9 | 1 | 0 |
| Downy brome | 4 | 9 | 1 | 0 | 0 |
| Giant foxtail | 10 | 10 | 10 | 2 | 0 |
| Lambsquarter | 9 | 9 | 8 | 0 | 0 |
| Morningglory | 6 | 4 | 1 | 0 | 0 |
| Nutsedge | — | 7 | 0 | 0 | 0 |
| Rape | 3 | 5 | 1 | 0 | 0 |
| Rice | 0 | 0 | 0 | 0 | 0 |
| Sorghum | 3 | 6 | 1 | 0 | 0 |
| Soybean | 0 | 0 | 0 | 0 | 0 |
| Sugar beet | 7 | 9 | 5 | 0 | 0 |

TABLE B-continued

| Velvetleaf | 1 | 7 | 0 | 0 | 0 |
|---|---|---|---|---|---|
| Wheat | 1 | 1 | 0 | 0 | 0 |
| Wild buckwheat | 4 | 3 | 2 | 0 | 0 |
| Wild oat | 7 | 9 | 2 | 0 | 0 |

TEST C

The compounds evaluated in this test were formulated in a non-phytoxic solvent mixture which includes a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgare*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (*Digitaria sanguinalis*), downy brome (*Bromus tectorum*), galium (*Galium aparine*), giant foxtail (*Setaria faberii*), johnsongrass (*Sorghum halpense*), lambsquarters (*Chenopodium album*), morningglory (*Ipomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza saliva*), umbrella sedge (*Cyperus difformis*), duck salad (*Heteranthera limosa*), barnyardgrass (*Echinochloa crus-galli*) and Late watergrass (*Echinocloa oryzicola*) grown to the 1 and 2 leaf stage for testing.

All plant species were grown using normal greenhouse practices. Visual evaluations of injury expressed on treated plants, when compared to untreated controls, were recorded approximately fourteen to twenty one days after application of the test compound. Plant response ratings, summarized in Table C, were recorded on a 0 to 100 scale where 0 is no effect and 100 is complete control. A dash (—) response means no test result.

TABLE C

POSTEMERGENCE

| Rate 1000 g/ha | COMPOUND 64 |
|---|---|
| Barley Igri | — |
| Barnyardgrass | — |
| Blackgrass | — |
| Chickweed | — |
| Cocklebur | — |
| Corn | — |
| Cotton | — |
| Crabgrass | — |
| Downy brome | — |
| Duck salad | 90 |
| Galium | — |
| Giant foxtail | — |
| It. rygrass | — |
| Johnsongrass | — |
| Lambsquarter | — |

TABLE C-continued

POSTEMERGENCE

| Rate 1000 g/ha | COMPOUND 64 |
|---|---|
| Morningglory | — |
| Rape | — |
| Redroot pigweed | — |
| Rice japonica | 50 |
| Soybean | — |
| Speedwell | — |
| Sugar beet | — |
| Umbrella sedge | 90 |
| Velvetleaf | — |
| Watergrass 2 | 95 |
| Wheat | — |
| Wild buckwheat | — |
| Wild oat | — |
| Barnyardgrass 2 | 95 |

TABLE C

POSTEMERGENCE

| | COMPOUND | | | | | | | COMPOUND | | | | | | | | |
|---|---|---|---|---|---|---|---|---|---|---|---|---|---|---|---|---|
| | 4 | 5 | 6 | 12 | 13 | 24 | 64 | 1 | 2 | 3 | 4 | 5 | 6 | 12 | 13 | 14 | 16 | 23 |
| | | | Rate 500 g/ha | | | | | | | | | Rate 250 g/ha | | | | | | |
| Barley Igri | 35 | 25 | 35 | 30 | — | 45 | — | 40 | 30 | — | 30 | 25 | 35 | 30 | — | 14 | 17 | 23 |
| Barnyardgrass | 30 | 90 | 90 | 80 | — | 70 | — | 90 | 80 | — | 30 | 90 | 45 | 35 | — | 45 | 30 | 80 |
| Blackgrass | 30 | 85 | 80 | 55 | — | 50 | — | 70 | 65 | — | 30 | 80 | 70 | 55 | — | 35 | 25 | 65 |
| Chickweed | 75 | 100 | 95 | 100 | — | 80 | — | 100 | 100 | — | 75 | 95 | 70 | 95 | — | 60 | 65 | 90 |
| Cocklebur | 35 | 80 | 85 | 50 | — | 65 | — | 55 | 50 | — | 25 | 60 | 70 | 50 | — | 60 | 60 | 90 |
| Corn | 20 | 50 | 35 | 35 | — | 45 | — | 95 | 30 | — | 15 | 45 | 20 | 25 | — | 25 | 20 | 80 |
| Cotton | 40 | 100 | — | 90 | — | 100 | — | 100 | 70 | — | 30 | 95 | 100 | 80 | — | 85 | 50 | 100 |
| Crabgrass | 35 | 95 | 90 | 95 | — | 100 | — | 95 | 60 | — | 30 | 90 | 30 | 70 | — | 70 | 60 | 95 |
| Downy brome | 10 | 65 | 20 | 20 | — | 25 | — | 80 | 0 | — | 10 | 35 | 0 | 20 | — | 30 | 35 | 60 |
| Duck salad | 10 | 95 | 25 | 80 | 0 | 35 | 80 | 45 | 55 | 40 | 10 | 10 | 10 | 35 | 0 | 25 | 20 | 30 |
| Galium | 35 | 95 | 95 | 0 | — | 70 | — | 20 | 90 | — | 30 | 95 | 90 | 0 | — | 35 | 55 | 30 |
| Giant foxtail | 25 | 90 | 90 | 70 | — | 40 | — | 100 | 50 | — | 25 | 90 | 35 | 35 | — | 90 | 60 | 95 |
| It. rygrass | 20 | 80 | 70 | 40 | — | 25 | — | 90 | 20 | — | 0 | 80 | 30 | 20 | — | 35 | 15 | 70 |
| Johnsongrass | 30 | 85 | 65 | 60 | — | 95 | — | 100 | 75 | — | 20 | 85 | 30 | 35 | — | 60 | 35 | 95 |
| Lambsquarter | 70 | 65 | 80 | 80 | — | 85 | — | 35 | 95 | — | 65 | 40 | 80 | 80 | — | 20 | 30 | 15 |
| Morningglory | 60 | 90 | 95 | 95 | — | 100 | — | 85 | 95 | — | 50 | 90 | 90 | 85 | — | 40 | 35 | 90 |
| Rape | 90 | 100 | 90 | 100 | — | 80 | — | 100 | 95 | — | 40 | 80 | 80 | 80 | — | 55 | 50 | 100 |
| Redroot pigweed | 50 | 100 | 90 | 95 | — | 100 | — | 100 | 90 | — | 50 | 90 | 90 | 90 | — | 85 | 60 | 90 |
| Rice japonica | 0 | 25 | 35 | 45 | 25 | 55 | 25 | 70 | 45 | 30 | 0 | 15 | 20 | 35 | 20 | 30 | 25 | 50 |
| Soybean | 90 | 35 | 70 | 50 | — | 65 | — | 50 | 100 | — | 60 | 35 | 30 | 40 | — | 20 | 30 | 65 |
| Speedwell | 95 | 100 | 100 | 100 | — | 100 | — | 100 | 100 | — | 95 | 100 | 95 | 100 | — | 95 | 90 | 100 |
| Sugar beet | 75 | 100 | 95 | 100 | — | 100 | — | 100 | 100 | — | 65 | 100 | 90 | 100 | — | 45 | 60 | 100 |
| Umbrella sedge | 35 | 80 | 90 | 60 | 0 | 65 | 60 | 75 | 95 | 80 | 30 | 80 | 80 | 50 | 0 | 30 | 45 | 85 |
| Velvetleaf | 50 | 90 | 80 | 90 | — | 65 | — | 90 | 90 | — | 50 | 90 | 70 | 80 | — | 75 | 60 | 100 |
| Watergrass 2 | 35 | 70 | 80 | 65 | 40 | 70 | 85 | 90 | 65 | 70 | 30 | 60 | 65 | 55 | 40 | 55 | 30 | 90 |
| Wheat | 40 | 40 | 25 | 15 | — | 25 | — | 65 | 30 | — | 35 | 30 | 25 | 10 | — | 10 | 15 | 45 |
| Wild buckwheat | 70 | 90 | 50 | 55 | — | 55 | — | 80 | 75 | — | 20 | 90 | 50 | 50 | — | 70 | 85 | 100 |
| Wild oat | 35 | 40 | 45 | 35 | — | 40 | — | 85 | 55 | — | 30 | 35 | 40 | 20 | — | 35 | 30 | 60 |
| Barnyardgrass 2 | 25 | 75 | 85 | 75 | 20 | 70 | 90 | 85 | 95 | 85 | 25 | 75 | 70 | 65 | 15 | 60 | 40 | 85 |

TABLE C-continued

| | COMPOUND | | | | | | | | COMPOUND | | | | | | | | | |
|---|---|---|---|---|---|---|---|---|---|---|---|---|---|---|---|---|---|---|
| | 24 | 25 | 26 | 37 | 55 | 58 | 62 | 64 | 1 | 2 | 3 | 4 | 5 | 6 | 7 | 12 | 13 | 14 |
| | Rate 250 g/ha | | | | | | | | Rate 125 g/ha | | | | | | | | | |
| Barley Igri | 40 | 45 | 35 | 35 | 20 | 25 | 25 | — | 35 | 20 | — | 20 | 25 | 30 | 25 | 20 | — | 20 |
| Barnyardgrass | 50 | 85 | 55 | 60 | 90 | 50 | 70 | — | 85 | 35 | — | 20 | 65 | 20 | 30 | 20 | — | 30 |
| Blackgrass | 35 | 75 | 35 | 40 | 70 | 65 | 65 | — | 70 | 50 | — | 25 | 30 | 30 | 35 | 35 | — | 30 |
| Chickweed | 40 | 70 | 70 | 10 | 100 | 100 | 90 | — | 100 | 100 | — | 75 | — | — | 90 | 55 | — | 40 |
| Cocklebur | 50 | 90 | 80 | 20 | 35 | 50 | 40 | — | 35 | 45 | — | 15 | 60 | 50 | 55 | 35 | — | 55 |
| Corn | 35 | 70 | 40 | 40 | 45 | 30 | 20 | — | 60 | 25 | — | 10 | 35 | 15 | 25 | 15 | — | 15 |
| Cotton | 70 | 95 | 95 | 10 | 20 | 70 | 25 | — | 95 | 70 | — | 25 | 95 | 90 | 65 | 80 | — | 80 |
| Crabgrass | 95 | 95 | 95 | 25 | 60 | 20 | 40 | — | 95 | 40 | — | 25 | 35 | 15 | 50 | 50 | — | 35 |
| Downy brome | 10 | 65 | 30 | 0 | 0 | 0 | 20 | — | 65 | 0 | — | 0 | 10 | 0 | 20 | 0 | — | 20 |
| Duck salad | 10 | 35 | 35 | 0 | 70 | 90 | 70 | 70 | 15 | 30 | 30 | 0 | 0 | 0 | 10 | 15 | 0 | 0 |
| Galium | 70 | 55 | 45 | 0 | 65 | 20 | 0 | — | 20 | 65 | — | 20 | 20 | 70 | 65 | 0 | — | 20 |
| Giant foxtail | 35 | 95 | 85 | 65 | 65 | 35 | 60 | — | 100 | 30 | — | 20 | 85 | 25 | 30 | 25 | — | 35 |
| It. rygrass | 25 | 65 | 65 | 35 | 15 | 70 | 20 | — | 80 | 20 | — | 0 | 50 | 30 | 15 | 10 | — | 20 |
| Johnsongrass | 55 | 95 | 90 | 15 | 35 | 60 | 60 | — | 95 | 60 | 13 | 10 | 30 | 20 | 35 | 25 | — | 35 |
| Lambsquarter | 85 | 70 | 75 | 0 | 95 | 65 | 50 | — | 15 | 90 | — | 55 | 0 | 50 | 35 | 30 | — | 15 |
| Morningglory | 65 | 90 | 90 | 20 | 40 | 80 | 75 | — | 75 | 80 | — | 40 | 80 | 90 | 65 | 70 | — | 40 |
| Rape | 75 | 100 | 100 | 20 | 30 | 60 | 30 | — | 95 | 80 | — | 40 | 45 | 40 | 25 | 60 | — | 40 |
| Redroot pigweed | 95 | 90 | 95 | 30 | 50 | 85 | 90 | — | 70 | 75 | — | 35 | 85 | 85 | 80 | 85 | — | 30 |
| Rice japonica | 40 | 60 | 65 | 10 | 40 | 55 | 70 | 15 | 60 | 25 | 15 | 0 | 0 | 0 | 35 | 15 | 15 | 25 |
| Soybean | 65 | 65 | 65 | 0 | 20 | 50 | 85 | — | 30 | 100 | — | 40 | 35 | 20 | 50 | — | — | 10 |
| Speedwell | 100 | 100 | 100 | 100 | 100 | 100 | — | — | 100 | 100 | — | 95 | 100 | 90 | 35 | 95 | — | — |
| Sugar beet | 100 | 95 | 95 | 0 | 100 | 100 | 90 | — | 100 | 100 | — | 25 | 95 | 70 | 100 | 85 | — | 35 |
| Umbrella sedge | 55 | 90 | 80 | 35 | 95 | 95 | 90 | 50 | 70 | 90 | 75 | 20 | 80 | 55 | 80 | 35 | 0 | 20 |
| Velvetleaf | 65 | 95 | 90 | 0 | 30 | 50 | 30 | — | 75 | 90 | — | 30 | 90 | 70 | 65 | 65 | — | 45 |
| Watergrass 2 | 70 | 85 | 80 | 30 | 90 | 90 | 85 | 50 | 85 | 40 | 60 | 30 | 55 | 55 | 70 | 30 | 20 | 45 |
| Wheat | 25 | 45 | 30 | 10 | 20 | 10 | 50 | — | 45 | 25 | — | 25 | 20 | 20 | 15 | 0 | — | 10 |
| Wild buckwheat | 55 | 100 | 30 | 0 | 80 | 65 | 80 | — | 80 | 35 | — | 0 | 70 | 50 | 100 | 45 | — | 60 |
| Wild oat | 35 | 85 | 65 | 35 | 50 | 70 | 50 | — | 80 | 35 | — | 10 | 30 | 40 | 25 | 20 | — | 30 |
| Barnyardgrass 2 | 70 | 85 | 70 | 35 | 95 | 95 | 85 | 50 | 80 | 75 | 70 | 25 | 65 | 60 | 50 | 50 | 0 | 45 |

| | COMPOUND | | | | | | | | | | COMPOUND | | | | | | | |
|---|---|---|---|---|---|---|---|---|---|---|---|---|---|---|---|---|---|---|
| | 17 | 23 | 24 | 25 | 26 | 37 | 55 | 58 | 62 | 64 | 1 | 2 | 3 | 4 | 5 | 6 | 7 | 12 |
| | Rate 125 g/ha | | | | | | | | | | Rate 62 g/ha | | | | | | | |
| Barley Igri | 30 | 35 | 35 | 40 | 35 | 0 | 10 | 10 | 25 | — | 25 | 20 | — | 20 | 20 | 25 | 15 | 15 |
| Barnyardgrass | 20 | 70 | 45 | 80 | 45 | 50 | 40 | 40 | 50 | — | 70 | 20 | — | 10 | 60 | 15 | 30 | 15 |
| Blackgrass | 15 | 55 | 25 | 60 | 20 | 30 | 50 | 50 | 50 | — | 55 | 30 | — | 25 | 30 | 30 | 30 | 20 |
| Chickweed | 30 | 90 | 30 | 70 | 50 | 0 | 100 | 100 | 80 | — | 65 | 95 | — | 35 | 95 | 70 | 25 | 50 |
| Cocklebur | 60 | — | 50 | 85 | 75 | 20 | 30 | 40 | 30 | — | 30 | 45 | — | 15 | 55 | 50 | 45 | 20 |
| Corn | 15 | 65 | 30 | 65 | 40 | 10 | 20 | 30 | 10 | — | 60 | 20 | — | 0 | 25 | 15 | 20 | 10 |
| Cotton | 50 | 90 | 65 | 90 | 90 | 0 | 20 | 70 | 20 | — | 70 | 70 | — | — | 85 | 25 | — | 70 |
| Crabgrass | 35 | 90 | 85 | 95 | 85 | 25 | 20 | 15 | 30 | — | 90 | 25 | — | 15 | 35 | 10 | 50 | 45 |
| Downy brome | 25 | 20 | 0 | 40 | 10 | 0 | 0 | 0 | 20 | — | 35 | 0 | — | 0 | 0 | 0 | 20 | 0 |
| Duck salad | 0 | 15 | 10 | 30 | 25 | 0 | 0 | 40 | 50 | 70 | 0 | 10 | 25 | 0 | 0 | 0 | 10 | 0 |
| Galium | 40 | 30 | 25 | 55 | 40 | 0 | 10 | 0 | — | 10 | 50 | — | 20 | 20 | 60 | 30 | 0 | |
| Giant foxtail | 30 | 90 | 25 | 95 | 40 | 65 | 20 | 20 | 40 | — | 95 | 20 | — | 15 | 80 | 15 | 30 | 20 |
| It. rygrass | 10 | 60 | 0 | 60 | 35 | 25 | 15 | 50 | 20 | 50 | 0 | — | 0 | 35 | 20 | 0 | 0 | |
| Johnsongrass | 20 | 95 | 50 | 95 | 85 | 0 | 30 | 50 | 30 | — | 95 | 45 | — | 0 | 25 | 10 | 35 | 20 |
| Lambsquarter | 10 | — | 80 | 50 | 75 | 0 | 35 | 35 | 50 | — | 15 | 80 | — | 55 | 0 | 50 | 0 | 30 |
| Morningglory | 30 | 90 | 65 | 90 | 85 | 20 | 35 | 50 | 50 | — | 70 | 70 | — | 40 | 80 | 20 | 55 | 65 |
| Rape | 40 | 100 | 70 | 95 | 0 | 25 | 60 | 30 | — | 90 | 70 | — | 40 | 45 | 40 | 10 | 40 | |
| Redroot pigweed | 35 | 90 | 90 | 90 | 0 | — | 80 | 90 | 90 | — | 70 | 60 | — | 25 | 80 | 80 | 70 | 75 |
| Rice japonica | 10 | 40 | 40 | 50 | 65 | 10 | 15 | 25 | 65 | 10 | 40 | 10 | 10 | 0 | 0 | 0 | 20 | 10 |
| Soybean | 20 | 50 | 65 | 65 | 60 | 0 | 20 | 35 | 50 | — | 0 | 70 | — | 30 | 35 | — | — | — |
| Speedwell | 90 | 100 | 100 | 100 | 100 | 90 | 100 | 100 | — | — | 100 | 100 | — | 90 | 100 | 0 | 35 | 85 |
| Sugar beet | 45 | 100 | 100 | 90 | 95 | 0 | 80 | 100 | 30 | — | 90 | 100 | — | 0 | 95 | — | 95 | 85 |
| Umbrella sedge | 35 | 45 | 40 | 85 | 70 | 30 | 90 | 95 | 90 | 20 | 70 | 85 | 65 | 10 | 70 | 35 | 70 | 15 |
| Velvetleaf | 40 | 95 | 65 | 95 | 85 | 0 | 20 | 50 | 20 | — | 70 | 80 | — | 15 | 80 | 35 | 65 | 60 |
| Watergrass 2 | 25 | 85 | 70 | 65 | 70 | 20 | 70 | 55 | 80 | 30 | 85 | 30 | 45 | 10 | 55 | 20 | 55 | 25 |
| Wheat | 15 | 40 | 0 | 25 | 25 | 0 | 0 | 0 | 50 | — | 25 | 25 | — | 20 | 10 | 10 | 10 | 0 |
| Wild buckwheat | 60 | 95 | 30 | 100 | 30 | 0 | 45 | 45 | 30 | — | 30 | 35 | — | 0 | 70 | 0 | 55 | 10 |
| Wild oat | 25 | 50 | 30 | 75 | 55 | 20 | 35 | 50 | 50 | — | 60 | 35 | — | 0 | 30 | 40 | 25 | 20 |
| Barnyardgrass 2 | 20 | 80 | 65 | 70 | 55 | 25 | 85 | 85 | 85 | 25 | 75 | 35 | 50 | 25 | 50 | 35 | 40 | |

| | COMPOUND | | | | | | | | | |
|---|---|---|---|---|---|---|---|---|---|---|
| | 13 | 14 | 17 | 23 | 24 | 25 | 26 | 37 | 55 | 58 | 62 |
| | | | | | Rate 62 g/ha | | | | | | |
| Barley Igri | — | 10 | 20 | 30 | 30 | 35 | 25 | 0 | 0 | 10 | 25 |
| Barnyardgrass | — | 20 | 15 | 70 | 25 | 70 | 40 | 10 | 20 | 15 | 25 |

TABLE C-continued

| | | | | | | | | | | |
|---|---|---|---|---|---|---|---|---|---|---|
| Blackgrass | — | 20 | 10 | 35 | 0 | 50 | 10 | 20 | 25 | 20 | 30 |
| Chickweed | — | 30 | 20 | 80 | 10 | 70 | 45 | 0 | 95 | 100 | 60 |
| Cocklebur | — | 30 | 50 | 80 | 45 | — | 70 | 10 | 25 | 40 | 10 |
| Corn | — | 15 | 15 | 45 | 25 | 55 | 35 | 0 | 10 | 15 | 10 |
| Cotton | — | 75 | 45 | 90 | 50 | 90 | 90 | 0 | 0 | 35 | 20 |
| Crabgrass | — | 25 | 25 | 90 | 85 | 95 | 80 | 10 | 10 | 10 | 20 |
| Downy brome | — | 15 | 10 | 15 | 0 | 20 | 0 | 0 | 0 | 0 | 0 |
| Duck salad | 0 | 0 | 0 | 0 | 0 | 0 | 0 | 25 | 0 | 0 | 30 | 50 |
| Galium | — | 10 | 20 | 25 | 25 | 55 | 25 | 0 | 10 | 10 | 0 |
| Giant foxtail | — | 30 | 20 | 75 | 15 | 90 | 90 | 10 | 10 | 10 | 20 |
| It. rygrass | — | 10 | 10 | 40 | 0 | 25 | 20 | 10 | 10 | 20 | 0 |
| Johnsongrass | — | 20 | 10 | 90 | 40 | 90 | 80 | 0 | 20 | 15 | — |
| Lambsquarter | — | 10 | 0 | 0 | 50 | 40 | 70 | 0 | 35 | 35 | 50 |
| Morningglory | — | 30 | 30 | 85 | 0 | 85 | 85 | 0 | 30 | 35 | 35 |
| Rape | — | 20 | 30 | 90 | 15 | 95 | 85 | 0 | 20 | 60 | 30 |
| Redroot pigweed | — | 20 | 30 | 90 | 90 | 90 | 90 | 0 | 40 | 50 | 90 |
| Rice japonica | 20 | 0 | 25 | 30 | 40 | 10 | 0 | 10 | 15 | 55 | |
| Soybean | — | 0 | 10 | 50 | 50 | 65 | 60 | 0 | 10 | 20 | 35 |
| Speedwell | — | 75 | 75 | 100 | 90 | — | 100 | 85 | 100 | 100 | — |
| Sugar beet | — | 15 | 25 | 100 | 95 | — | 95 | 0 | 80 | 100 | 30 |
| Umbrella sedge | 0 | 20 | 25 | 40 | 0 | 85 | 60 | 20 | 80 | 95 | 85 |
| Velvetleaf | — | 45 | 40 | 90 | 20 | 90 | 75 | 0 | 10 | 30 | 0 |
| Watergrass 2 | 0 | 40 | 0 | 0 | 40 | 65 | 45 | 15 | 35 | 35 | 70 |
| Wheat | — | 0 | 10 | 25 | 0 | 20 | 20 | 0 | 0 | 0 | 50 |
| Wild buckwheat | — | −30 | 70 | 15 | 90 | 30 | 0 | 45 | 10 | 20 | |
| Wild oat | — | 20 | 25 | 45 | 25 | 60 | 40 | 10 | 30 | 40 | 40 |
| Barnyardgrass 2 | 0 | 35 | 0 | 70 | 45 | 60 | 50 | 10 | 35 | 55 | 75 |

PREEMERGENCE

| | COMPOUND | | | | | | COMPOUND | | | | | | | |
|---|---|---|---|---|---|---|---|---|---|---|---|---|---|---|
| | 4 | 5 | 6 | 12 | 13 | 24 | 1 | 2 | 3 | 4 | 5 | 6 | 12 | 13 | 14 | 17 | 23 |
| | Rate 500 g/ha | | | | | | Rate 250 g/ha | | | | | | | |
| Barley Igri | 0 | 55 | 20 | 25 | 0 | 45 | 70 | 30 | 35 | 0 | 35 | 10 | 0 | 0 | 10 | 10 | 30 |
| Barnyardgrass | 40 | 80 | 50 | 55 | 40 | 90 | 95 | 75 | 100 | 20 | 70 | 20 | 30 | 20 | 80 | 30 | 100 |
| Blackgrass | 60 | 95 | 90 | 90 | 75 | 100 | 90 | 65 | 95 | 20 | 90 | 90 | 80 | 30 | 75 | 55 | 100 |
| Chickweed | 90 | 95 | 85 | 70 | 80 | 65 | 100 | 70 | 100 | 70 | 95 | 75 | — | 80 | 85 | 100 | 100 |
| Cocklebur | 0 | 0 | 10 | 0 | 0 | 0 | 0 | 0 | 0 | 0 | 0 | 0 | 0 | 0 | 0 | 20 | 0 |
| Corn | 0 | 35 | 20 | 0 | 10 | 35 | 90 | 20 | 25 | 0 | 35 | 10 | 0 | 0 | 15 | 0 | 35 |
| Cotton | 25 | 30 | 10 | 30 | 40 | 0 | 0 | 0 | 50 | 20 | 20 | 0 | 10 | 10 | 0 | 0 | — |
| Crabgrass | 100 | 100 | 65 | 90 | 90 | 100 | 95 | 100 | 100 | 100 | 100 | 50 | 85 | — | 100 | 65 | 100 |
| Downy brome | 10 | 10 | 10 | 0 | 10 | 30 | 95 | 20 | 35 | 0 | 10 | 10 | 0 | 0 | 35 | 35 | 95 |
| Galium | 10 | 90 | 10 | 0 | 30 | 50 | 25 | 70 | 100 | 0 | 0 | 0 | 0 | 0 | 25 | 75 | 90 |
| Giant foxtail | 100 | 100 | 100 | 100 | 100 | 100 | 100 | 100 | 100 | 100 | 100 | 100 | 100 | 100 | 100 | 100 | 100 |
| It. rygrass | 30 | 80 | 35 | 25 | 25 | 95 | 100 | 30 | 70 | 15 | 60 | 0 | 10 | 25 | 30 | 35 | 100 |
| Johnsongrass | 20 | 70 | 10 | 20 | 35 | 55 | 80 | 70 | 100 | 15 | 70 | 10 | 10 | 30 | 60 | 45 | 95 |
| Lambsquarter | 95 | 100 | 95 | 100 | 95 | 95 | 100 | 60 | 95 | 95 | 60 | 80 | 95 | 25 | 90 | 95 | 100 |
| Morningglory | 30 | 70 | 35 | 35 | 20 | 65 | 90 | 95 | 60 | 20 | — | 25 | 30 | 15 | 40 | 50 | 95 |
| Rape | 80 | 20 | 10 | 0 | 0 | 35 | 95 | 30 | 70 | 35 | 20 | 10 | 0 | 0 | 20 | 60 | 100 |
| Redroot pigweed | 100 | 100 | 100 | 100 | 100 | 100 | 100 | 100 | 100 | 100 | 100 | 95 | 95 | 90 | 95 | 30 | 100 |
| Soybean | 0 | 0 | 0 | 0 | 10 | 20 | 10 | 10 | 20 | 0 | 0 | 0 | 0 | 0 | 20 | — | 0 |
| Speedwell | — | 100 | 95 | 95 | 100 | 100 | 100 | 100 | 100 | — | 100 | 95 | 95 | 100 | — | — | — |
| Sugar beet | 100 | 95 | 90 | 40 | 90 | 100 | 100 | 100 | 100 | 100 | 95 | — | 40 | 80 | 95 | 90 | 100 |
| Velvetleaf | 40 | 75 | 45 | 60 | 25 | 70 | 100 | 100 | 90 | 40 | 60 | 30 | 40 | 20 | 30 | 20 | 85 |
| Wheat | 10 | 55 | 20 | 20 | 10 | 20 | 65 | 20 | 65 | 0 | 30 | 10 | 10 | 10 | 20 | 30 | 45 |
| Wild buckwheat | 35 | 95 | 0 | 75 | 40 | 40 | 90 | 35 | 25 | 20 | 95 | 0 | 60 | 40 | 70 | 80 | 100 |
| Wild oat | 20 | 95 | 85 | 95 | 35 | 75 | 100 | 50 | 60 | 10 | 85 | 65 | 85 | 20 | 75 | 35 | 100 |

| | COMPOUND | | | | | | COMPOUND | | | | | | | |
|---|---|---|---|---|---|---|---|---|---|---|---|---|---|---|
| | 24 | 25 | 26 | 37 | 55 | 58 | 62 | 1 | 2 | 3 | 4 | 5 | 6 | 7 | 12 | 13 | 14 |
| | Rate 250 g/ha | | | | | | | Rate 125 g/ha | | | | | | |
| Barley Igri | 25 | 45 | 20 | 10 | 0 | 0 | 0 | 5 | 20 | 25 | 0 | 20 | 0 | 0 | 0 | 0 | 10 |
| Barnyardgrass | 70 | 95 | 20 | 50 | 90 | 90 | 95 | 80 | 50 | 85 | 15 | 40 | 10 | 35 | 10 | 10 | 60 |
| Blackgrass | 90 | 100 | 100 | 75 | 55 | 30 | 100 | 80 | 40 | 75 | 20 | 40 | 70 | 35 | 80 | 20 | 65 |
| Chickweed | 60 | 100 | 100 | 100 | 95 | 95 | 65 | 85 | 60 | 90 | 50 | 45 | — | 35 | 60 | 65 | |
| Cocklebur | 0 | 10 | 10 | 0 | 0 | 0 | 0 | 0 | 0 | 0 | 0 | 0 | 0 | 0 | 0 | 0 | 0 |
| Corn | 0 | 60 | 10 | 35 | 10 | 0 | 0 | 75 | 20 | 10 | 0 | 15 | 0 | 30 | 0 | 0 | 0 |
| Cotton | 0 | 20 | 0 | 0 | 0 | 0 | 25 | 0 | 0 | 10 | 10 | 0 | 0 | 0 | 10 | 0 | 0 |
| Crabgrass | 95 | 100 | 100 | 100 | 95 | 50 | 100 | 95 | 90 | 100 | 95 | 85 | 35 | 95 | 35 | 65 | 80 |
| Downy brome | 10 | 100 | 95 | 35 | 10 | 20 | 10 | 55 | 10 | 35 | 0 | 0 | 0 | 35 | 0 | 0 | 30 |
| Galium | 30 | 100 | 0 | 65 | 10 | 10 | 10 | 25 | 45 | 80 | 0 | 0 | 0 | 10 | 0 | 0 | 20 |
| Giant foxtail | 100 | 100 | 100 | 100 | 100 | 100 | 95 | 100 | 100 | 100 | 100 | 95 | 90 | 70 | 100 | 95 | 95 | 100 |
| It. rygrass | 90 | 100 | 90 | 65 | 30 | 30 | 90 | 100 | 10 | 70 | 15 | 10 | 0 | 65 | 0 | 25 | 25 |
| Johnsongrass | 25 | 90 | 50 | 30 | 20 | 20 | 50 | 45 | 30 | 60 | 0 | 30 | 0 | 55 | 0 | 10 | 40 |
| Lambsquarter | 95 | 100 | 65 | 65 | 95 | 90 | 95 | 95 | 60 | — | 95 | 0 | 20 | 90 | 0 | — | 50 |

TABLE C-continued

| | | | | | | | | | | | | | | | | | |
|---|---|---|---|---|---|---|---|---|---|---|---|---|---|---|---|---|---|
| Morningglory | 70 | 65 | 30 | 60 | 60 | 90 | 75 | 80 | 50 | 10 | 65 | 20 | 60 | 25 | 10 | 30 | |
| Rape | 35 | 100 | 35 | 10 | 65 | 55 | 35 | 65 | 20 | 45 | 20 | 10 | 0 | 10 | 0 | 0 | 20 |
| Redroot pigweed | 95 | 100 | 100 | 50 | 100 | 100 | 100 | 100 | 90 | 100 | 95 | 60 | 95 | 45 | 85 | 50 | 0 |
| Soybean | 0 | 20 | 10 | 30 | 95 | 10 | 0 | 0 | 0 | 15 | 0 | — | — | 10 | 0 | — | 20 |
| Speedwell | 100 | — | — | 100 | 100 | 95 | 100 | 100 | 95 | 100 | — | 90 | 0 | 100 | 95 | 100 | |
| Sugar beet | 95 | 100 | 100 | 0 | 95 | 100 | 95 | 100 | 100 | 100 | 35 | — | 30 | 95 | 20 | 30 | 95 |
| Velvetleaf | 70 | 100 | 20 | 30 | 70 | 75 | 65 | 100 | 80 | 70 | 30 | 20 | 20 | 30 | 30 | 10 | 30 |
| Wheat | 0 | 50 | 10 | 10 | 10 | 0 | 0 | 40 | 10 | 20 | 0 | 25 | 0 | 0 | 10 | 0 | |
| Wild buckwheat | 40 | 95 | 0 | 85 | 20 | 60 | 35 | 60 | 25 | 10 | 10 | 70 | 0 | 35 | 25 | 10 | — |
| Wild oat | 45 | 100 | 65 | 45 | 30 | 20 | 90 | 100 | 25 | 40 | 0 | 35 | 30 | 35 | 65 | 10 | 60 |

| | COMPOUND | | | | | | | | | COMPOUND | | | | | | | | |
|---|---|---|---|---|---|---|---|---|---|---|---|---|---|---|---|---|---|---|
| | 17 | 23 | 24 | 25 | 26 | 37 | 55 | 58 | 62 | 1 | 2 | 3 | 4 | 5 | 6 | 7 | 12 | 13 |
| | Rate 125 g/ha | | | | | | | | | 62 g/ha | | | | | | | | |
| Barley Igri | 0 | 25 | 0 | 0 | 0 | 10 | 10 | 0 | 35 | 10 | 25 | 0 | 10 | 0 | 0 | 0 | 0 | 0 |
| Barnyardgrass | 25 | 65 | 35 | 70 | 10 | 35 | 40 | 40 | 90 | 80 | 30 | 50 | 10 | 40 | 10 | 10 | 0 | 10 |
| Blackgrass | 45 | — | 65 | 95 | 55 | 70 | 30 | 30 | 50 | 80 | 30 | 20 | — | 40 | 20 | 30 | 80 | 20 |
| Chickweed | 80 | 100 | 55 | 100 | 100 | 20 | 90 | 95 | 65 | 55 | 30 | 90 | 50 | 45 | 30 | 0 | 60 | 40 |
| Cocklebur | 0 | 0 | 0 | 0 | 0 | 0 | 0 | 0 | 0 | 0 | 0 | 0 | 0 | 0 | 0 | 0 | 0 | 0 |
| Corn | 0 | 35 | 0 | 45 | 0 | 15 | 10 | 0 | 0 | 65 | 10 | 0 | 0 | — | 0 | 0 | 0 | 0 |
| Cotton | 0 | 0 | 0 | 20 | 0 | 0 | 0 | 0 | 20 | 0 | 0 | 0 | 0 | 0 | 0 | 0 | 0 | 0 |
| Crabgrass | — | 100 | 95 | 100 | — | 60 | 90 | — | 100 | 95 | 70 | 100 | 70 | 45 | 35 | — | 25 | 60 |
| Downy brome | 20 | 25 | 0 | 85 | 25 | 0 | 10 | 20 | 0 | 30 | 0 | 35 | 0 | 0 | 0 | 10 | 0 | 0 |
| Galium | 30 | 0 | 10 | 100 | 0 | 0 | 0 | 10 | 0 | 25 | 35 | 10 | 0 | 0 | 0 | 0 | 0 | 0 |
| Giant foxtail | 100 | 100 | 100 | 100 | 100 | 85 | 95 | 95 | 100 | 100 | 95 | 100 | 90 | 90 | 20 | 95 | 55 | 50 |
| It. rygrass | 30 | 0 | 60 | 85 | 20 | 30 | 20 | 30 | 40 | 95 | 0 | 65 | 0 | 0 | 0 | 20 | 0 | 25 |
| Johnsongrass | 40 | 70 | 10 | 75 | 20 | 20 | 10 | 20 | 30 | 35 | 10 | 60 | 0 | 25 | 0 | 35 | 0 | 10 |
| Lambsquarter | 90 | 100 | 90 | 100 | 65 | 35 | 70 | 90 | 80 | 95 | 60 | 80 | 0 | 0 | 0 | 85 | 0 | 20 |
| Morningglory | 35 | — | 35 | 70 | 35 | 10 | 30 | 60 | 65 | 65 | 50 | 50 | 10 | 35 | 10 | 50 | 15 | 10 |
| Rape | 35 | 30 | 0 | 80 | 20 | 0 | 30 | 55 | 20 | 65 | 10 | 0 | 0 | 0 | 0 | 0 | 0 | 0 |
| Redroot pigwee 30 | 100 | 85 | 100 | 100 | 0 | 100 | 100 | 100 | 100 | 90 | 100 | 50 | — | 85 | 40 | 70 | 25 | |
| Soybean | 20 | 0 | 0 | 20 | 0 | 30 | 20 | 0 | 0 | 0 | 0 | 0 | 0 | 0 | 0 | 10 | 0 | 0 |
| Speedwell | — | — | 100 | — | — | 100 | 100 | 95 | 90 | 100 | 90 | 100 | — | 90 | 0 | 20 | 30 | 100 |
| Sugar beet | 85 | 100 | 95 | 95 | 100 | 0 | 95 | 100 | 85 | 100 | 70 | 65 | 15 | 95 | 10 | 90 | 20 | 0 |
| Velvetleaf | 20 | 75 | 35 | 85 | 0 | 0 | 30 | 70 | 35 | 70 | 60 | 50 | 20 | 20 | 0 | 30 | 15 | — |
| Wheat | 20 | 25 | 0 | 25 | 0 | 10 | 0 | 0 | 0 | 35 | 0 | — | 0 | 20 | 0 | 0 | 10 | 0 |
| Wild buckwheat | 70 | 85 | 10 | 90 | 0 | 20 | 20 | 60 | 15 | 60 | 20 | 0 | 0 | 70 | 0 | 0 | 0 | 0 |
| Wild oat | 30 | 65 | 35 | 85 | 35 | 35 | 20 | 10 | 30 | 95 | 0 | 30 | 0 | 30 | 30 | 25 | 40 | 10 |

| | COMPOUND | | | | | | | | | |
|---|---|---|---|---|---|---|---|---|---|---|
| | 14 | 17 | 23 | 24 | 25 | 26 | 37 | 55 | 58 | 62 |
| Barley Igri | 0 | 0 | 15 | 0 | 0 | 0 | 0 | 0 | 0 | 0 |
| Barnyardgrass | 25 | 25 | 30 | 25 | 55 | 10 | 10 | 25 | 30 | 40 |
| Blackgrass | 30 | 35 | 100 | 45 | 95 | 55 | 35 | 20 | 25 | 30 |
| Chickweed | 70 | 80 | 100 | 20 | 100 | 95 | 0 | 20 | — | 40 |
| Cocklebur | 0 | 0 | 0 | 0 | 0 | 0 | 0 | 0 | 0 | 0 |
| Corn | 0 | 0 | 10 | 0 | 30 | 0 | 0 | 0 | 0 | 0 |
| Cotton | 0 | 0 | 0 | 0 | 20 | 0 | 0 | 0 | 0 | 0 |
| Crabgrass | 30 | 40 | 100 | 50 | 95 | 100 | 40 | 40 | 50 | 90 |
| Downy brome | 10 | 0 | 10 | 0 | 60 | 0 | 0 | 0 | 10 | 0 |
| Galium | 10 | 25 | 0 | 0 | 40 | 0 | 0 | 0 | 0 | 0 |
| Giant foxtail | 100 | 100 | 100 | 90 | 100 | 100 | 85 | 85 | 35 | 100 |
| It. rygrass | 15 | 20 | 0 | 20 | 20 | 0 | 20 | 85 | 35 | 100 |
| Johnsongrass | 40 | 20 | 35 | 0 | 25 | 20 | 10 | 0 | 10 | 20 |
| Lambsquarter | 20 | 20 | 85 | 45 | 100 | 65 | 30 | 70 | 60 | 70 |
| Morningglory | 30 | 20 | 60 | 35 | 45 | 20 | 10 | 30 | 30 | 40 |
| Rape | 10 | 20 | 20 | 0 | 40 | 0 | 0 | 20 | 20 | 0 |
| Redroot pigweed | 0 | 30 | 100 | — | 100 | 100 | 0 | 90 | 95 | 90 |
| Soybean | 0 | 0 | 0 | 0 | 20 | 0 | 0 | 10 | 0 | 0 |
| Speedwell | — | — | — | 100 | — | — | 100 | 70 | — | 75 |
| Sugar beet | 70 | 65 | 100 | 80 | 95 | 100 | 0 | 65 | 70 | — |
| Velvetleaf | 0 | 0 | 15 | 30 | 65 | 0 | 0 | 10 | 10 | 25 |
| Wheat | 0 | 0 | 0 | 0 | 10 | 0 | 0 | 0 | 0 | 0 |
| Wild buckwheat | 0 | 70 | 80 | 0 | 90 | 0 | 0 | 10 | 25 | 10 |
| Wild oat | 35 | 25 | 45 | 10 | 65 | 0 | 0 | 10 | 10 | 20 |

TABLE C

POSTEMERGENCE

| Rate 31 g/ha | COMPOUND | | | | | | | | | | | | |
|---|---|---|---|---|---|---|---|---|---|---|---|---|---|
| | 1 | 2 | 3 | 7 | 14 | 17 | 23 | 25 | 26 | 37 | 55 | 58 | 62 |
| Barley Igri | 20 | 20 | — | 10 | 0 | 20 | 30 | 25 | 20 | 0 | 0 | 10 | 20 |
| Barnyardgrass | 50 | 10 | — | 30 | 10 | 10 | 45 | 50 | 40 | 10 | 10 | 10 | 20 |
| Blackgrass | 30 | 10 | — | 20 | 10 | 10 | 25 | 20 | 10 | 0 | 25 | 20 | 30 |
| Chickweed | 50 | 80 | — | 20 | 30 | 20 | 75 | 55 | 30 | 0 | 95 | 100 | 40 |
| Cocklebur | 20 | 40 | — | 40 | 10 | 40 | 70 | 85 | 70 | 0 | 15 | 40 | 10 |
| Corn | 30 | 20 | — | 15 | 10 | 10 | 35 | 50 | 35 | 0 | 0 | 10 | 0 |
| Cotton | 40 | 55 | — | 45 | 30 | 30 | 90 | 90 | 90 | 0 | 0 | 25 | 10 |
| Crabgrass | 35 | 20 | — | 50 | 20 | 20 | 90 | 85 | 80 | 10 | 10 | 10 | 10 |
| Downy brome | 10 | 0 | — | 0 | 10 | 0 | 10 | 15 | 0 | 0 | 0 | 0 | 0 |
| Duck salad | 0 | 0 | 10 | 0 | 0 | 0 | 0 | 0 | 0 | 0 | 0 | 0 | 35 |
| Galium | 0 | 45 | — | 25 | 10 | — | 20 | 50 | 25 | 0 | 10 | 10 | 0 |
| Giant foxtail | 60 | 10 | — | 30 | 25 | 10 | 70 | 85 | 30 | 0 | 10 | 10 | 20 |
| It. rygrass | 40 | 0 | — | 0 | 0 | 0 | 30 | 20 | 0 | 0 | 0 | 10 | 0 |
| Johnsongrass | 80 | 30 | — | 20 | 10 | 0 | 85 | 85 | 65 | 0 | 10 | 0 | — |
| Lambsquarter | 0 | 80 | — | 0 | 0 | 0 | 0 | 35 | 70 | 0 | 30 | 30 | 20 |
| Morningglory | 70 | — | — | — | 10 | 20 | 80 | 80 | 80 | 0 | 20 | 30 | 30 |
| Rape | 85 | 30 | — | 10 | 20 | 15 | 70 | 90 | 75 | 0 | 20 | 60 | 0 |
| Redroot pigweed | 65 | 60 | — | 70 | 10 | 30 | 90 | 90 | 90 | 0 | 40 | 50 | 80 |
| Rice japonica | 20 | 10 | 10 | 20 | 0 | 0 | 0 | 25 | 0 | 0 | 0 | 0 | 35 |
| Soybean | 0 | 60 | — | 40 | 0 | 10 | 25 | 65 | 60 | 0 | 0 | — | 20 |
| Speedwell | 100 | 95 | — | 20 | 60 | 20 | 95 | 100 | 100 | 85 | 95 | 100 | — |
| Sugar beet | 90 | 80 | — | 70 | 10 | 20 | 45 | 90 | 90 | 0 | 55 | 100 | 25 |
| Umbrella sedge | 65 | 55 | 35 | 60 | 20 | 0 | 30 | 75 | 60 | 0 | 70 | 75 | 75 |
| Velvetleaf | 60 | 80 | — | 50 | 30 | 30 | 85 | 90 | 70 | 0 | 10 | 20 | 0 |
| Watergrass 2 | 70 | 20 | 10 | 30 | 30 | 0 | 65 | 50 | 45 | 0 | 10 | 25 | 60 |
| Wheat | 25 | 10 | — | 0 | 0 | 10 | 25 | 10 | 10 | 0 | 0 | 0 | 20 |
| Wild buckwheat | 20 | 30 | — | 30 | 40 | 20 | 60 | 80 | 30 | 0 | 0 | 10 | 0 |
| Wild oat | 40 | 25 | — | 25 | 15 | 20 | 40 | 45 | 20 | 10 | 30 | 30 | 30 |
| Barnyardgrass 2 | 65 | 30 | 30 | 20 | 25 | 0 | 45 | 55 | 40 | 0 | 10 | 30 | 70 |

PREEMERGENCE

| Rate 31 g/ha | COMPOUND | | | | | | | | | | | | |
|---|---|---|---|---|---|---|---|---|---|---|---|---|---|
| | 1 | 2 | 3 | 7 | 14 | 17 | 23 | 25 | 26 | 37 | 55 | 58 | 62 |
| Barley Igri | 10 | 0 | 20 | 0 | 0 | 0 | 0 | 0 | 0 | 0 | 0 | 0 | 0 |
| Barnyardgrass | 70 | 10 | 40 | 10 | 0 | 0 | 15 | 25 | 0 | 0 | 10 | 20 | 10 |
| Blackgrass | 45 | 25 | 20 | 10 | 20 | 35 | 55 | 55 | 20 | 10 | 10 | 25 | 20 |
| Chickweed | 30 | 10 | 70 | 0 | 35 | 70 | 100 | 100 | 90 | 0 | 10 | 90 | 40 |
| Cocklebur | 0 | 0 | 0 | 0 | 0 | 0 | 0 | 0 | 0 | 0 | 0 | 0 | 0 |
| Corn | 50 | 10 | 0 | 0 | 0 | 0 | 10 | 0 | 0 | 0 | 0 | 0 | 0 |
| Cotton | 0 | 0 | 0 | 0 | 0 | 0 | 0 | 0 | 0 | 0 | 0 | 0 | 0 |
| Crabgrass | 95 | 30 | 70 | 85 | 25 | 40 | 100 | 90 | 45 | 30 | 30 | 30 | 35 |
| Downy brome | 20 | 0 | 25 | 0 | 0 | 0 | 0 | 40 | 0 | 0 | 0 | 0 | 0 |
| Galium | 10 | 10 | 10 | 0 | 10 | 0 | 0 | 25 | 0 | 0 | 0 | 0 | 0 |
| Giant foxtail | 100 | 90 | 95 | 90 | 80 | 80 | 100 | 100 | 55 | 40 | 60 | — | 100 |
| It. rygrass | 90 | 0 | 0 | 20 | 10 | 0 | 0 | 0 | 0 | 0 | 0 | 10 | 10 |
| Johnsongrass | 30 | 0 | 10 | 35 | 0 | 0 | 10 | 10 | 0 | 0 | 0 | 10 | 0 |
| Lambsquarter | 90 | 30 | 80 | 35 | 10 | 0 | 0 | 90 | 0 | 20 | 10 | 45 | 60 |
| Morningglory | 60 | — | 20 | 30 | 0 | 20 | — | 10 | 0 | 0 | 30 | 30 | 20 |
| Rape | 20 | 0 | 0 | 0 | 10 | 0 | 10 | 40 | 0 | 0 | 20 | 20 | 0 |
| Redroot pigweed | 100 | 75 | 100 | 35 | 0 | 30 | 100 | 100 | 70 | 0 | 70 | 95 | 90 |
| Soybean | 0 | 0 | 0 | 0 | 0 | 0 | 0 | 20 | 0 | 0 | 0 | 0 | 0 |
| Speedwell | 100 | 35 | 95 | 20 | — | — | — | — | — | 95 | 10 | 95 | — |
| Sugar beet | 100 | 40 | 65 | 75 | 25 | 20 | 90 | 95 | 90 | 0 | 30 | 70 | 30 |
| Velvetleaf | 60 | 25 | 0 | 20 | 0 | 0 | 0 | 25 | 0 | 0 | 10 | 10 | 20 |
| Wheat | 30 | 0 | 0 | 0 | 0 | 0 | 0 | 0 | 0 | 0 | 0 | 0 | 0 |
| Wild buckwheat | 35 | 10 | 0 | 0 | 0 | 0 | 65 | 85 | 0 | 0 | 0 | 25 | 0 |
| Wild oat | 85 | 0 | 20 | 0 | 15 | 10 | 25 | 40 | 0 | 0 | 0 | 0 | 20 |
| Wheat | 30 | 0 | 0 | 0 | 0 | 0 | 0 | 0 | 0 | 0 | 0 | 0 | 0 |
| Wild buckwheat | 35 | 10 | 0 | 0 | 0 | 0 | 65 | 85 | 0 | 0 | 0 | 25 | 0 |
| Wild oat | 85 | 0 | 20 | 0 | 15 | 10 | 25 | 40 | 0 | 0 | 0 | 0 | 20 |

TABLE C

POSTEMERGENCE

| Rate 16 g/ha | COMPOUND 7 | 25 |
|---|---|---|
| Barley Igri | 10 | 20 |
| Barnyardgrass | 20 | 50 |
| Blackgrass | 15 | 20 |
| Chickweed | 10 | 40 |
| Cocklebur | 35 | 85 |
| Corn | 15 | 50 |
| Cotton | 40 | 90 |
| Crabgrass | 15 | 85 |
| Downy brome | 0 | 10 |
| Duck salad | 0 | 0 |
| Galium | 0 | 40 |
| Giant foxtail | 20 | 85 |
| It. rygrass | 0 | 10 |
| Johnsongrass | 0 | 85 |
| Lambsquarter | 0 | 30 |
| Morningglory | 25 | 75 |
| Rape | 10 | 75 |
| Redroot pigweed | 35 | 90 |
| Rice japonica | 10 | 20 |
| Soybean | 30 | 65 |
| Speedwell | 20 | 100 |
| Sugar beet | 70 | 80 |
| Umbrella sedge | 20 | 60 |
| Velvetleaf | 25 | 90 |
| Watergrass 2 | 0 | 45 |
| Wheat | 0 | 0 |
| Wild buckwheat | 15 | 65 |
| Wild oat | 20 | 40 |
| Barnyardgrass 2 | 0 | 50 |

PREEMERGENCE

| Rate 16 g/ha | COMPOUND 7 | 25 |
|---|---|---|
| Barley Igri | 0 | 0 |
| Barnyardgrass | 0 | 0 |
| Blackgrass | 10 | 30 |
| Chickweed | 0 | 100 |
| Cocklebur | 0 | 0 |
| Corn | 0 | 0 |
| Cotton | 0 | 0 |
| Crabgrass | 10 | 90 |
| Downy brome | 0 | 0 |
| Galium | 0 | 15 |
| Giant foxtail | 80 | 95 |
| It. rygrass | 0 | 0 |
| Johnsongrass | 20 | 0 |
| Lambsquarter | 10 | 85 |

TABLE C-continued

| | | |
|---|---|---|
| Morningglory | 20 | 10 |
| Rape | 0 | 10 |
| Redroot pigweed | 20 | 100 |
| Soybean | 0 | 20 |
| Speedwell | 20 | — |
| Sugar beet | 70 | 80 |
| Velvetleaf | 10 | 10 |
| Wheat | 0 | 0 |
| Wild buckwheat | 0 | 40 |
| Wild oat | 0 | 20 |

TEST D

Seeds of barnyardgrass (*Echinochloa crus-galli*), bindweed (*Concolculus arvensis*), black nightshade (*Solanum ptycanthum dunal*), cassia (*Cassia obtusifolia*), cocklebur (*Xanthium pensylvanicum*), common ragweed (*Ambrosia artemisiifolia*), corn (*Zea mays*), cotton (*Gossypium hirsutam*), crabgrass (*Digitaria spp.*), fall panicum (*Panicum dichotomiflorum*), giant foxtail (*Setaria faberii*), green foxtail (*Setaria viridis*), jimsonweed (*Datura stramonium*), johnsongrass (*Sorghum halepense*), lambsquarter (*Chenopodium album*), morningglory (*Ipomoea spp.*), pigweed (*Amaranthus retroflexus*), prickly sida (*Sida spinosa*), shattercane (*Sorghum vulgare*), signalgrass (*Brachiaria platyphylla*), smartweed (*Polygonum pensylvanicum*), soybean (*Glycine max*), sunflower (*Helianthus annuus*), velvetleaf (*Abutilon theophrasti*), wild proso (*Pancium miliaceum*), woolly cupgrass (*Eriochloa villosa*), yellow foxtail (*Setaria lutescens*) and purple nutsedge (*Cyperus rotundus*) tubers were planted into a matapeake sandy loam soil. These crops and weeds were grown in the greenhouse until the plants ranged in height from two to eighteen cm (one to four leaf stage), then treated postemergence with the test chemicals formulated in a non-phytotoxic solvent mixture which includes a surfactant. Pots receiving preemergence treatments were planted immediately prior to test chemical application. Pots treated in this fashion were placed in the greenhouse and maintained according to routine greenhouse procedures.

Treated plants and untreated controls were maintained in the greenhouse approximately 14–21 days after application of the test compound. Visual evaluations of plant injury responses were then recorded. Plant response ratings, summarized in Table D, are reported on a 0 to 100 scale where 0 is no effect and 100 is complete control.

TABLE D

PREEMERGENCE

| | COMPOUND 1 Rate 560 g/ha | COMPOUND 1 Rate 280 g/ha | COMPOUND 1 Rate 140 g/ha | COMPOUND 1 Rate 70 g/ha | COMPOUND 1 Rate 35 g/ha | COMPOUND 1 Rate 17 g/ha |
|---|---|---|---|---|---|---|
| Barnyardgrass | 100 | 100 | 75 | 60 | 25 | 10 |
| Bindweed | 100 | 100 | 95 | 15 | 0 | 0 |
| Blk Nightshade | 100 | 95 | 60 | 35 | 0 | 0 |
| Cassia | 0 | 0 | 0 | 0 | 0 | 0 |
| Cocklebur | — | 0 | 0 | 0 | 0 | 0 |
| Corn | 95 | 85 | 75 | 50 | 15 | 10 |
| Cotton | 0 | 10 | 0 | 0 | 0 | 0 |
| Crabgrass | 100 | 100 | 100 | 100 | 55 | 15 |
| Fall panicum | 100 | 100 | 95 | 80 | 25 | 15 |
| Giant foxtail | 100 | 100 | 100 | 100 | 100 | 30 |
| Green foxtail | 100 | 100 | 100 | 100 | 100 | 25 |
| Jimsonweed | 60 | 0 | 0 | 0 | 0 | 0 |

TABLE D-continued

| | | | | | | |
|---|---|---|---|---|---|---|
| Johnsongrass | 100 | 100 | 65 | 45 | 15 | 10 |
| Lambsquarter | 100 | 95 | 55 | 15 | 0 | 0 |
| Morningglory | 60 | 35 | 15 | 15 | 10 | 10 |
| Nutsedge | 70 | 35 | 10 | 0 | 0 | 0 |
| Pigweed | 100 | 100 | 100 | 100 | 85 | 0 |
| Prickly sida | 50 | 40 | 10 | 0 | 0 | 0 |
| Ragweed | 100 | 80 | 50 | 10 | 0 | 0 |
| Shattercane | 80 | 65 | 45 | 15 | 0 | 0 |
| Signalgrass | 100 | 100 | 100 | 95 | 70 | 25 |
| Smartweed | 100 | 100 | 65 | 30 | 0 | 0 |
| Soybean | 10 | 10 | 0 | 0 | 0 | 0 |
| Sunflower | 15 | 10 | 0 | 0 | 0 | 0 |
| Velvetleaf | 100 | 65 | 25 | 10 | 0 | 0 |
| Wild proso | 100 | 80 | 40 | 30 | 0 | 0 |
| Woolly cupgrass | 95 | 75 | 25 | 20 | 0 | 0 |
| Yellow foxtail | 100 | 100 | 100 | 100 | 65 | 20 |

| POSTEMERGENCE | | | | | |
|---|---|---|---|---|---|
| | COMPOUND 1<br>Rate 280 g/ha | COMPOUND 1<br>Rate 140 g/ha | COMPOUND 1<br>Rate 70 g/ha | COMPOUND 1<br>Rate 35 g/ha | COMPOUND 1<br>Rate 17 g/ha |
| Barnyardgrass | 65 | 55 | 50 | 20 | 0 |
| Bindweed | 0 | 0 | 0 | 0 | 0 |
| Blk Nightshade | 20 | 0 | 0 | 0 | 0 |
| Cassia | 0 | 0 | 0 | 0 | 0 |
| Cocklebur | 35 | 30 | 25 | 20 | 0 |
| Corn | 50 | 40 | 35 | 20 | 15 |
| Cotton | 85 | 85 | 80 | 65 | 60 |
| Crabgrass | 60 | 55 | 45 | 0 | 0 |
| Fall panicum | 75 | 70 | 65 | 0 | 0 |
| Giant foxtail | 65 | 60 | 50 | 0 | 0 |
| Green foxtail | 65 | 60 | 55 | 0 | 0 |
| Jimsonweed | 55 | 50 | 50 | 40 | 40 |
| Johnsongrass | 40 | 35 | 20 | 0 | 0 |
| Lambsquarter | 45 | 40 | 25 | 35 | 25 |
| Morningglory | 25 | 15 | 10 | 0 | 0 |
| Nutsedge | 0 | 0 | 0 | 0 | 0 |
| Pigweed | 60 | 55 | 45 | 40 | 35 |
| Prickly sida | 0 | 0 | 0 | 0 | 0 |
| Ragweed | 40 | 35 | 35 | 30 | 35 |
| Shattercane | 20 | 15 | 15 | 5 | 0 |
| Signalgrass | 25 | 20 | 15 | 0 | 0 |
| Soybean | 50 | 35 | 25 | 0 | 0 |
| Sunflower | 55 | 55 | 45 | 35 | 25 |
| Velvetleaf | 75 | 65 | 60 | 50 | 35 |
| Wild proso | 15 | 10 | 0 | 0 | 0 |
| Woolly cupgrass | 20 | 20 | 15 | 0 | 0 |
| Yellow foxtail | 60 | 60 | 55 | 0 | 0 |

TEST E

Compounds evaluated in this test were formulated in a non-phytoxic solvent mixture which includes a surfactant and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include winter barley (*Hordeum vulgare* cv. 'Igri'), blackgrass (*Alopecurus myosuroides*), chickweed (*Stellaria media*), downy brome (*Bromus tectorum*), galium (*Galium aparine*), green foxtail (*Setaria viridis*), kochia (*Kochia scoparia*), lambsquarters (*Chenopodium album*), speedwell (*Veronica persica*), ryegrass (*Lolium multiflorum*), spring wheat (*Triticum aestivum* cv. 'ERA'), windgrass (*Apera spica-venti*), winter wheat (*Triticum aestivum* cv. 'Talent'), wild buckwheat (*Polygonum convolvulus*), wild mustard (*Sinapis arvensis*) and wild oat (*Avena fatua*).

Blackgrass, galium and wild oat were treated at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table E, are based upon a 0 to 100 scale where 0 is no effect and 100 is complete control. A dash response (—) means no test result.

TABLE E

POSTEMERGENCE

| | COMPOUND | | | COMPOUND | | | COMPOUND | | | COMPOUND | | | COMPOUND 1 | COMPOUND 1 | COMPOUND 1 |
|---|---|---|---|---|---|---|---|---|---|---|---|---|---|---|---|
| | 1 | 23 | 25 | 1 | 23 | 25 | 1 | 23 | 25 | 1 | 23 | 25 | Rate 31 g/ha | Rate 16 g/ha | Rate 8 g/ha |
| | Rate 500 g/ha | | | Rate 250 g/ha | | | Rate 125 g/ha | | | Rate 62 g/ha | | | | | |
| Blackgrass (2) | 60 | 70 | 50 | 10 | 40 | 50 | 50 | 10 | 30 | 10 | 10 | 10 | 5 | 5 | 5 |
| Chickweed | 100 | 100 | 100 | 80 | 70 | 100 | 60 | 65 | 80 | 50 | 50 | 50 | 45 | 5 | 5 |
| Downy brome | 30 | 15 | 50 | 20 | 15 | 45 | 5 | 5 | 10 | 5 | 0 | 5 | 5 | 0 | 0 |
| Galium (2) | 90 | 55 | 70 | 65 | 40 | 65 | 50 | 40 | 60 | 50 | 30 | 60 | 40 | 10 | 10 |
| Green foxtail | 100 | 85 | 100 | 80 | 60 | 70 | 40 | 10 | 50 | 10 | 0 | 5 | 5 | 0 | 0 |
| Kochia | 98 | 90 | 85 | 95 | 85 | 85 | 60 | 85 | 80 | 60 | 70 | 80 | 50 | 0 | 0 |
| Lambsquarters | 100 | 100 | 100 | 100 | 100 | 85 | 80 | 50 | 80 | 50 | 40 | 60 | 50 | 0 | 0 |
| Ryegrass | 50 | 10 | 15 | 40 | 10 | 10 | 10 | 5 | 5 | 5 | 0 | 5 | 0 | 0 | 0 |
| Speedwell | 100 | 100 | 100 | 100 | 100 | 100 | 100 | 100 | 100 | 100 | 100 | 100 | 60 | 60 | 40 |
| Wheat (Spring) | 40 | 30 | 40 | 30 | 30 | 30 | 25 | 15 | 30 | 10 | 10 | 15 | 10 | 5 | 0 |
| Wheat (Winter) | 30 | 30 | 30 | 20 | 25 | 10 | 20 | 10 | 10 | 10 | 10 | 5 | 10 | 5 | 5 |
| Wild buckwheat | 100 | 100 | 100 | 98 | 100 | 90 | 70 | 70 | 80 | 5 | 60 | 55 | 5 | 0 | 0 |
| Wild mustard | 100 | 100 | — | 100 | 100 | 100 | 100 | 70 | 60 | 100 | 40 | 55 | 10 | 10 | 5 |
| Wild oat (2) | 50 | 35 | 45 | 40 | 35 | 30 | 20 | 30 | 30 | 10 | 10 | 10 | 10 | 10 | 5 |
| Windgrass | 100 | 80 | 70 | 90 | 60 | 60 | 30 | 10 | 40 | 5 | 10 | 40 | 5 | 5 | 5 |
| Winter Barley | 40 | 30 | 30 | 25 | 15 | 30 | 15 | 10 | 25 | 10 | 10 | 15 | 5 | 5 | 5 |

PREEMERGENCE

| | COMPOUND | | | COMPOUND | | | COMPOUND | | | COMPOUND | | | COMPOUND 1 | COMPOUND 1 | COMPOUND 1 |
|---|---|---|---|---|---|---|---|---|---|---|---|---|---|---|---|
| | 1 | 23 | 25 | 1 | 23 | 25 | 1 | 23 | 25 | 1 | 23 | 25 | Rate 31 g/ha | Rate 16 g/ha | Rate 8 g/ha |
| | Rate 500 g/ha | | | Rate 250 g/ha | | | Rate 125 g/ha | | | Rate 62 g/ha | | | | | |
| Blackgrass (2) | 100 | 100 | 100 | 70 | 60 | 40 | 60 | 50 | 10 | 40 | 5 | 5 | 5 | 0 | 0 |
| Chickweed | 100 | 100 | 100 | 100 | 100 | 100 | 100 | 55 | 100 | 50 | 30 | 70 | 0 | 0 | 0 |
| Downy brome | 100 | 100 | — | 100 | 100 | 100 | 50 | 5 | 60 | 5 | 0 | 20 | 0 | 0 | 0 |
| Galium (2) | 100 | 100 | 100 | 100 | 50 | 100 | — | 50 | 50 | 100 | — | 50 | 0 | 0 | 0 |
| Green foxtail | 100 | 100 | 100 | 100 | 100 | 100 | 100 | 100 | 100 | 100 | 100 | 100 | 100 | 100 | 50 |
| Kochia | 98 | 90 | 90 | 98 | 90 | 90 | 95 | 90 | 90 | 85 | 90 | 90 | 80 | 0 | 0 |
| Lambsquarters | 90 | 95 | 95 | 90 | 95 | 95 | 90 | 80 | 90 | 90 | 0 | 70 | 0 | 0 | 0 |
| Ryegrass | 100 | 80 | 100 | 100 | 80 | 10 | 60 | 10 | 5 | 50 | 0 | 0 | 5 | 0 | 0 |
| Speedwell | 100 | 100 | 100 | 100 | 100 | 100 | 100 | 100 | 100 | 100 | 70 | 100 | 70 | 70 | 55 |
| Wheat (Spring) | 60 | 40 | 50 | 40 | 25 | 50 | 35 | 5 | 20 | 10 | 5 | 5 | 5 | 0 | 0 |
| Wheat (Winter) | 60 | 40 | 45 | 55 | 20 | 20 | 50 | 5 | 5 | 40 | 0 | 0 | 0 | 0 | 0 |
| Wild buckwheat | 100 | 100 | 100 | 100 | 100 | 95 | 100 | 80 | 90 | 70 | 50 | 70 | 0 | 0 | 0 |
| Wild mustard | 100 | 100 | 100 | 100 | 100 | 100 | 100 | 100 | 90 | 100 | 40 | 40 | 60 | 5 | 0 |
| Wild oat (2) | 100 | 100 | 100 | 100 | 100 | 100 | 80 | 80 | 80 | 80 | 40 | 55 | 10 | 5 | 0 |
| Windgrass | 100 | 100 | 100 | 100 | 100 | 100 | 100 | 100 | 100 | 100 | 100 | 100 | — | — | 70 |
| Winter Barley | 45 | 20 | 15 | 45 | 10 | 5 | 30 | 5 | 0 | 10 | 5 | 0 | 0 | 0 | 0 |

I claim:

1. A compound of Formula I:

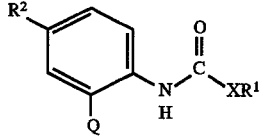

I wherein Q is

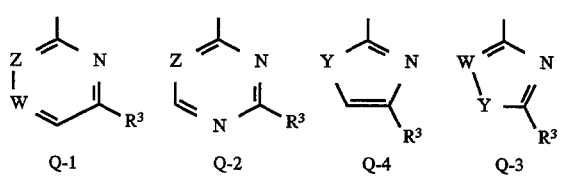

-continued

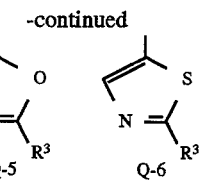

X is a single bond; O, S; or $NR^4$;

Y is O; S; or $NCH_3$;

Z is CH or N;

W is CH or N;

$R^1$ is $C_1$-$C_5$ alkyl optionally substituted with $C_1$-$C_2$ alkoxy, OH, 1–3 halogens, or $C_1$-$C_2$ alkylthio; $CH_2(C_3$-$C_4$ cycloalkyl); $C_3$-$C_4$ cycloalkyl optionally substituted with 1–3 methyl groups; $C_2$-$C_4$ alkenyl; $C_2$-$C_4$ haloalkenyl; or phenyl;

$R^2$ is H; chlorine: bromine; $C_1$-$C_2$ alkyl; $C_1$-$C_2$ alkoxy; $C_1$-$C_2$ alkylthio; $C_2$-$C_3$ alkoxyalkyl; $C_2$-$C_3$ alkylthioalkyl; cyano; nitro; $NH(C_1$-$C_2$ alkyl); or $N(C_1$-$C_2$ alkyl)$_2$;

$R^3$ is $C_1$-$C_4$ haloalkyl; $C_1$-$C_4$ haloalkoxy; $C_1$-$C_4$ haloalkylthio; halogen; cyano; nitro; or methylthio;

$R^4$ is H; $CH_3$ or $OCH_3$; and agriculturally suitable salts thereof.

2. A compound of claim 1 wherein:

$R^1$ is $C_1$-$C_4$ alkyl optionally substituted with methoxy or 1–3 halogens; $C_2$-$C_4$ alkenyl; or $C_2$-$C_4$ haloalkenyl;

$R^2$ is chlorine; bromine; $C_1$-$C_2$ alkyl; $C_1$-$C_2$ alkoxy; cyano; nitro; NH($C_1$-$C_2$ alkyl); or N($C_1$-$C_2$alkyl)$_2$.

3. A compound of claim 2 wherein:

X is a single bond;

$R^3$ is $C_1$-$C_2$ haloalkyl; $C_1$-$C_2$ haloalkoxy; $C_1$-$C_2$ haloalkylthio; chlorine or bromine.

4. A compound of claim 3 wherein:

Q is Q-1 or Q-2.

5. A compound according to claim 4 which is:

2-methyl-N-[4-methyl-2-[6-(trifluoromethyl)-2-pyridinyl]phenyl]-propanamide; or 2-methyl-N-[4-methyl-2-[2-(trifluoromethylthio)-4-pyrimidinyl]-phenyl]propanamide.

6. A composition for controlling growth of undesired vegetation comprising an effective amount of a compound of claim 1 and at least one of a surfactant, solid or liquid diluent.

7. A composition for controlling growth of undesired vegetation comprising an effective amount of a compound of claim 2 and at least one of a surfactant, solid or liquid diluent.

8. A composition for controlling growth of undesired vegetation comprising an effective amount of a compound of claim 4 and at least one of a surfactant, solid or liquid diluent.

9. A composition for controlling growth of undesired vegetation comprising an effective amount of a compound of claim 5 and at least one of a surfactant, solid or liquid diluent.

10. A method for controlling growth of undesired vegetation comprising applying to the locus to be protected an effective amount of the composition of claim 6.

* * * * *